US008715985B2

(12) United States Patent
Bertuzzi et al.

(10) Patent No.: US 8,715,985 B2
(45) Date of Patent: May 6, 2014

(54) CLOSTRIDIUM HISTOLYTICUM RECOMBINANT COLLAGENASES AND METHOD FOR THE MANUFACTURE THEREOF

(75) Inventors: Federico Bertuzzi, Milan (IT); Angela Cuttitta, Palermo (IT); Giulio Ghersi, Palermo (IT); Salvatore Mazzola, Palermo (IT); Monica Salamone, Palermo (IT); Gregorio Seidita, Palermo (IT)

(73) Assignee: Abiel S.R.L., Campobello (IT)

( * ) Notice: Subject to any disclaimer, the term of this patent is extended or adjusted under 35 U.S.C. 154(b) by 68 days.

(21) Appl. No.: 13/515,203

(22) PCT Filed: Dec. 15, 2010

(86) PCT No.: PCT/IB2010/055840
§ 371 (c)(1), (2), (4) Date: Jun. 11, 2012

(87) PCT Pub. No.: WO2011/073925
PCT Pub. Date: Jun. 23, 2011

(65) Prior Publication Data
US 2012/0252092 A1    Oct. 4, 2012

(30) Foreign Application Priority Data
Dec. 15, 2009   (IT) .............................. RM2009A0661

(51) Int. Cl.
*C12N 9/00*    (2006.01)
*C12N 9/48*    (2006.01)

(52) U.S. Cl.
USPC .......................................... 435/183; 435/212

(58) Field of Classification Search
None
See application file for complete search history.

(56) References Cited

U.S. PATENT DOCUMENTS

2008/0233614 A1    9/2008   Cranenburgh et al.

FOREIGN PATENT DOCUMENTS

| WO | 94/00580 | 1/1994 |
| WO | 2008/100833 | 8/2008 |

OTHER PUBLICATIONS

International Search Report for PCT/IB2010/055840, three pages, mailed Jun. 16, 2011.
Written Opinion of ISA for PCT/IB2010/055840, six pages, mailed Jun. 16, 2011.
Ducka et al. "A universal strategy for high-yield production of soluble and functional clostridial collagenases in *E. coli*" *Applied Microbiology and Biotechnology*, vol. 83, No. 6, pp. 1055-1065, Jul. 2009.
Matsushita et al. "Gene duplication and multiplicity of collagenases in *Clostridium histolyticum*" *Journal of Bacteriology*, vol. 181, No. 3, pp. 923-933, Feb. 1999.

*Primary Examiner* — Suzanne M Noakes
*Assistant Examiner* — Jae W Lee
(74) *Attorney, Agent, or Firm* — Nixon & Vanderhye PC

(57) ABSTRACT

The present invention relates to the production of recombinant collagenases, and in particular describes a method for the production of recombinant *Clostridium histolyticum* collagenases ColI characterized by a yield higher than approximately 140 mg/l of culture of said collagenases in soluble and biologically active form, collagenases produced by this method, compositions comprising these collagenases and the use thereof.

22 Claims, 15 Drawing Sheets

Figure 1:
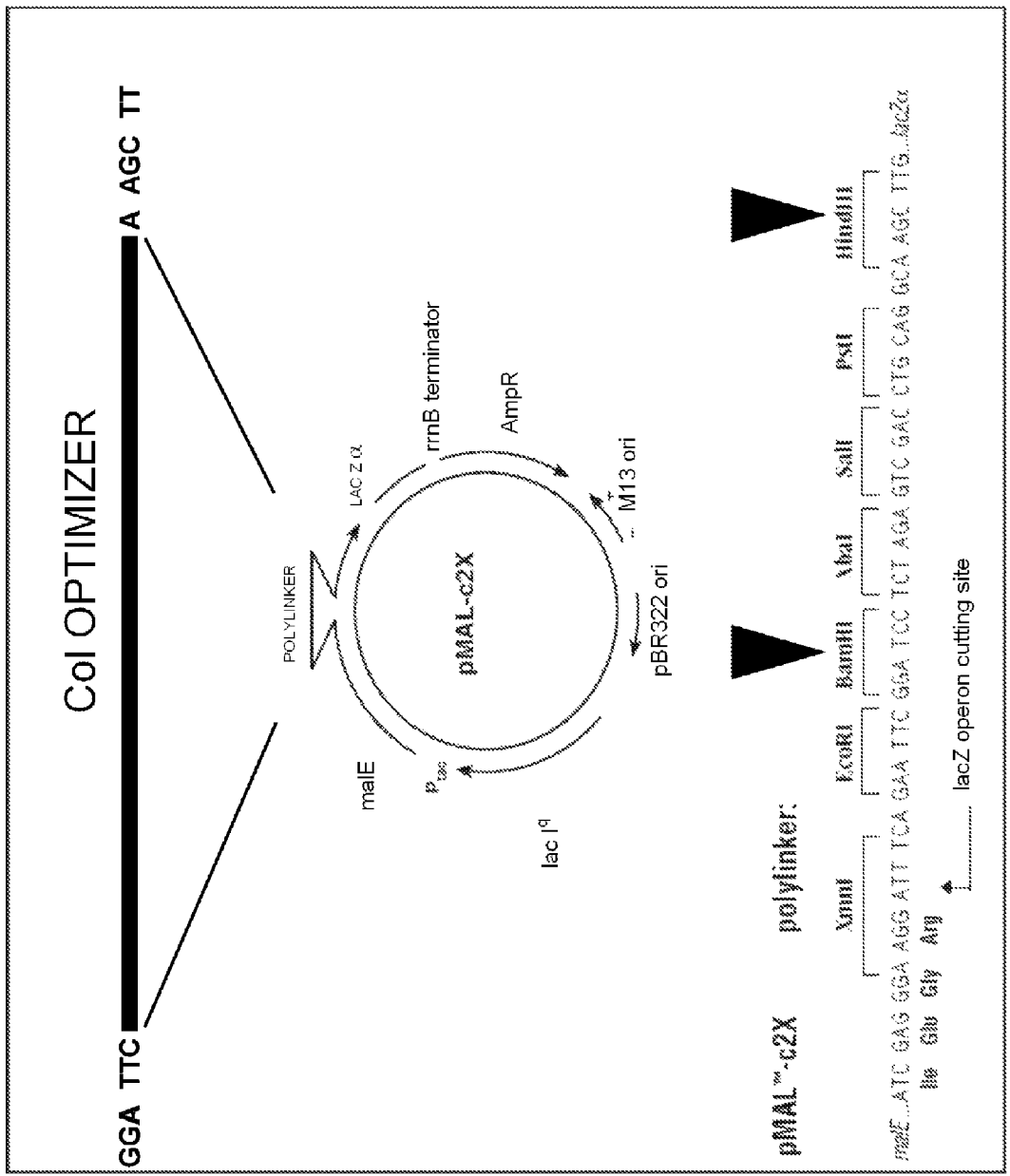

SEQUENCE LISTING

<160> NUMBER OF SEQ ID NOS: 5

<210> SEQ ID NO 1
<211> LENGTH: 3030
<212> TYPE: DNA
<213> ORGANISM: Artificial Sequence
<220> FEATURE:
<223> OTHER INFORMATION: sequence generated by optimization of the
      Clostridium histolyticum gene ColG for codon usage of genes highly
      expressed in Escherichia coli K12
<220> FEATURE:
<221> NAME/KEY: CDS
<222> LOCATION: (1)..(3030)

<400> SEQUENCE: 1

```
atg atc gcg aac acc aat agt gag aaa tac gac ttt gaa tac ttg aac       48
Met Ile Ala Asn Thr Asn Ser Glu Lys Tyr Asp Phe Glu Tyr Leu Asn
1               5                   10                  15 ggt ctg agc tac acg gaa ctg act aac ctg atc aaa aac att aag tgg       96
Gly Leu Ser Tyr Thr Glu Leu Thr Asn Leu Ile Lys Asn Ile Lys Trp
            20                  25                  30 aac cag atc aac ggc ctg ttc aat tat tct act ggc tct cag aaa ttc      144
Asn Gln Ile Asn Gly Leu Phe Asn Tyr Ser Thr Gly Ser Gln Lys Phe
        35                  40                  45 ttc ggt gac aaa aac cgt gta cag gcg att atc aac gcc ctg cag gaa      192
Phe Gly Asp Lys Asn Arg Val Gln Ala Ile Ile Asn Ala Leu Gln Glu
    50                  55                  60
```

```
tct ggc cgc act tat acc gct aac gac atg aaa ggc atc gag acc ttc        240
Ser Gly Arg Thr Tyr Thr Ala Asn Asp Met Lys Gly Ile Glu Thr Phe
65              70                  75                  80 act gaa gtt ctg cgt gcg ggt ttt tat ctg ggc tac tac aac gac ggt        288
Thr Glu Val Leu Arg Ala Gly Phe Tyr Leu Gly Tyr Tyr Asn Asp Gly
            85                  90                  95 ctg agc tat ctg aac gat cgc aat ttc cag gac aaa tgt atc ccg gcc        336
Leu Ser Tyr Leu Asn Asp Arg Asn Phe Gln Asp Lys Cys Ile Pro Ala
        100                 105                 110 atg atc gct att cag aaa aac ccg aac ttt aaa ctg ggc act gca gtg        384
Met Ile Ala Ile Gln Lys Asn Pro Asn Phe Lys Leu Gly Thr Ala Val
    115                 120                 125 cag gac gaa gtt att acc tct ctg ggc aaa ctg atc ggc aac gct tct        432
Gln Asp Glu Val Ile Thr Ser Leu Gly Lys Leu Ile Gly Asn Ala Ser
130                 135                 140 gcc aac gcc gaa gtt gtg aac aac tgc gtg ccg gtg ctt aag cag ttt        480
Ala Asn Ala Glu Val Val Asn Asn Cys Val Pro Val Leu Lys Gln Phe
145                 150                 155                 160 cgc gaa aac ctg aac cag tac gcc ccg gat tat gtt aag ggt acc gcc        528
Arg Glu Asn Leu Asn Gln Tyr Ala Pro Asp Tyr Val Lys Gly Thr Ala
                165                 170                 175 gta aat gaa ctg atc aaa ggc atc gaa ttt gac ttt tct ggt gct gcg        576
Val Asn Glu Leu Ile Lys Gly Ile Glu Phe Asp Phe Ser Gly Ala Ala
            180                 185                 190 tac gaa aag gat gtg aag acc atg ccg tgg tat ggt aaa atc gac ccg        624
Tyr Glu Lys Asp Val Lys Thr Met Pro Trp Tyr Gly Lys Ile Asp Pro
        195                 200                 205 ttc atc aac gaa ctg aaa gcc ctg ggc tta tat ggc aac att aca agc        672
Phe Ile Asn Glu Leu Lys Ala Leu Gly Leu Tyr Gly Asn Ile Thr Ser
    210                 215                 220 gcg acc gaa tgg gcg tca gat gtt ggt atc tat tac ttg agt aaa ttc        720
Ala Thr Glu Trp Ala Ser Asp Val Gly Ile Tyr Tyr Leu Ser Lys Phe
225                 230                 235                 240 ggc tta tat tcc acc aac cgt aac gac atc gtt caa agc ctg gag aaa        768
Gly Leu Tyr Ser Thr Asn Arg Asn Asp Ile Val Gln Ser Leu Glu Lys
                245                 250                 255 gcg gtt gat atg tac aaa tac ggg aaa atc gca ttt gta gcg atg gaa        816
Ala Val Asp Met Tyr Lys Tyr Gly Lys Ile Ala Phe Val Ala Met Glu
            260                 265                 270 cgc att acc tgg gac tac gac ggc atc ggc tca aat ggc aaa aaa gtc        864
Arg Ile Thr Trp Asp Tyr Asp Gly Ile Gly Ser Asn Gly Lys Lys Val
        275                 280                 285 gac cac gat aaa ttc ctg gat gac gca gag aaa cac tac ctg cct aaa        912
Asp His Asp Lys Phe Leu Asp Asp Ala Glu Lys His Tyr Leu Pro Lys
    290                 295                 300 acc tac acc ttc gac aac ggc aca ttc atc att cgt gct ggc gac aaa        960
Thr Tyr Thr Phe Asp Asn Gly Thr Phe Ile Ile Arg Ala Gly Asp Lys
305                 310                 315                 320 gta agc gaa gaa aaa atc aaa aga ctc tac tgg gcg agc cgt gaa gtc       1008
Val Ser Glu Glu Lys Ile Lys Arg Leu Tyr Trp Ala Ser Arg Glu Val
                325                 330                 335 aaa agc cag ttt cat cgc gtt gtt ggt aat gac aaa gcg ctg gaa gtt       1056
Lys Ser Gln Phe His Arg Val Val Gly Asn Asp Lys Ala Leu Glu Val
            340                 345                 350 ggt aac gca gat gac gtt tta aca atg aaa atc ttc aat agc ccc gag       1104
Gly Asn Ala Asp Asp Val Leu Thr Met Lys Ile Phe Asn Ser Pro Glu
        355                 360                 365 gag tat aag ttt aac act aac att aac gga gta agc acc gac aac ggt       1152
Glu Tyr Lys Phe Asn Thr Asn Ile Asn Gly Val Ser Thr Asp Asn Gly
    370                 375                 380
```

-continued

```
ggt ctg tat atc gaa cct cgc ggc act ttc tat act tat gaa cgc act       1200
Gly Leu Tyr Ile Glu Pro Arg Gly Thr Phe Tyr Thr Tyr Glu Arg Thr
385                 390                 395                 400 ccg cag cag tct att ttc tcc ctg gaa gaa ctc ttt cgc cac gaa tat       1248
Pro Gln Gln Ser Ile Phe Ser Leu Glu Glu Leu Phe Arg His Glu Tyr
                405                 410                 415 acc cat tat ctg caa gcg cgt tat ctg gtc gat ggc tgg ggc cag           1296
Thr His Tyr Leu Gln Ala Arg Tyr Leu Val Asp Gly Leu Trp Gly Gln
            420                 425                 430 ggt cct ttc tat gaa aag aac cgt ctg acc tgg ttc gat gaa ggt acc       1344
Gly Pro Phe Tyr Glu Lys Asn Arg Leu Thr Trp Phe Asp Glu Gly Thr
        435                 440                 445 gca gaa ttc ttc gct ggc agc act cgt acc agc ggt gta ctg ccg cgc       1392
Ala Glu Phe Phe Ala Gly Ser Thr Arg Thr Ser Gly Val Leu Pro Arg
    450                 455                 460 aaa agc atc ctg ggc tat ctg gca aaa gac aaa gtg gat cac cgt tac       1440
Lys Ser Ile Leu Gly Tyr Leu Ala Lys Asp Lys Val Asp His Arg Tyr
465                 470                 475                 480 agc ctg aaa aaa acc ctg aat tct gga tac gat gac tcc gat tgg atg       1488
Ser Leu Lys Lys Thr Leu Asn Ser Gly Tyr Asp Asp Ser Asp Trp Met
                485                 490                 495 ttt tac aac tac ggt ttt gcc gtg gcg cac tac ctg tac gag aaa gat       1536
Phe Tyr Asn Tyr Gly Phe Ala Val Ala His Tyr Leu Tyr Glu Lys Asp
            500                 505                 510 atg cct acg ttc atc aag atg aac aag gcg att ctg aat act gac gtt       1584
Met Pro Thr Phe Ile Lys Met Asn Lys Ala Ile Leu Asn Thr Asp Val
        515                 520                 525 aaa agc tat gat gag atc att aag aaa ctg tcc gac gac gca aac aaa       1632
Lys Ser Tyr Asp Glu Ile Ile Lys Lys Leu Ser Asp Asp Ala Asn Lys
    530                 535                 540 aac aca gaa tac cag aac cat atc cag gaa tta gca gat aaa tac cag       1680
Asn Thr Glu Tyr Gln Asn His Ile Gln Glu Leu Ala Asp Lys Tyr Gln
545                 550                 555                 560 ggt gcg ggt atc ccg ctg gtt tcc gat gac tat ctt aaa gat cac ggt       1728
Gly Ala Gly Ile Pro Leu Val Ser Asp Asp Tyr Leu Lys Asp His Gly
                565                 570                 575 tat aaa aaa gcg tcc gaa gta tac tcc gaa att agc aaa gcg gca tcc       1776
Tyr Lys Lys Ala Ser Glu Val Tyr Ser Glu Ile Ser Lys Ala Ala Ser
            580                 585                 590 ctg acc aac acg tct gtt acc gcc gaa aaa tcc cag tac ttt aac acg       1824
Leu Thr Asn Thr Ser Val Thr Ala Glu Lys Ser Gln Tyr Phe Asn Thr
        595                 600                 605 ttc acg ctg cgt ggt acc tat acg ggt gaa acg tct aaa ggc gaa ttc       1872
Phe Thr Leu Arg Gly Thr Tyr Thr Gly Glu Thr Ser Lys Gly Glu Phe
    610                 615                 620 aaa gac tgg gat gag atg tcc aag aaa ctg gat ggt act ctg gaa agc       1920
Lys Asp Trp Asp Glu Met Ser Lys Lys Leu Asp Gly Thr Leu Glu Ser
625                 630                 635                 640 ctg gcg aaa aat tct tgg tct ggt tac aag acc ctg acc gct tat ttc       1968
Leu Ala Lys Asn Ser Trp Ser Gly Tyr Lys Thr Leu Thr Ala Tyr Phe
                645                 650                 655 acc aac tac cgt gtc acc tcc gac aac aag gta cag tac gac gtt gtc       2016
Thr Asn Tyr Arg Val Thr Ser Asp Asn Lys Val Gln Tyr Asp Val Val
            660                 665                 670 ttc cac ggc gtg ctg acc gat aac gca gac atc tct aac aac aag gcc       2064
Phe His Gly Val Leu Thr Asp Asn Ala Asp Ile Ser Asn Asn Lys Ala
        675                 680                 685 ccg atc gcg aaa gtt acc ggt ccg tcc acc ggt gct gtt ggt cgt aac       2112
Pro Ile Ala Lys Val Thr Gly Pro Ser Thr Gly Ala Val Gly Arg Asn
    690                 695                 700
```

```
atc gaa ttc tcc ggc aaa gac tcc aaa gat gaa gac ggc aaa att gtg    2160
Ile Glu Phe Ser Gly Lys Asp Ser Lys Asp Glu Asp Gly Lys Ile Val
705                 710                 715                 720 tct tat gat tgg gac ttc ggt gac ggt gct acg tcc cgt ggc aaa aac    2208
Ser Tyr Asp Trp Asp Phe Gly Asp Gly Ala Thr Ser Arg Gly Lys Asn
                725                 730                 735 agc gtg cac gca tac aaa aaa gcg ggt acc tac aac gtt aca ttg aaa    2256
Ser Val His Ala Tyr Lys Lys Ala Gly Thr Tyr Asn Val Thr Leu Lys
            740                 745                 750 gtg act gac gat aaa ggc gct acc gcg act gaa tct ttc act atc gaa    2304
Val Thr Asp Asp Lys Gly Ala Thr Ala Thr Glu Ser Phe Thr Ile Glu
        755                 760                 765 att aaa aac gaa gac act acc acc ccg att acc aag gaa atg gaa cca    2352
Ile Lys Asn Glu Asp Thr Thr Thr Pro Ile Thr Lys Glu Met Glu Pro
    770                 775                 780 aat gac gac atc aaa gaa gct aac ggc ccg atc gtc gaa ggt gtg acc    2400
Asn Asp Asp Ile Lys Glu Ala Asn Gly Pro Ile Val Glu Gly Val Thr
785                 790                 795                 800 gta aaa ggt gac ctg aat ggt tcg gat gac gca gac acc ttc tac ttc    2448
Val Lys Gly Asp Leu Asn Gly Ser Asp Asp Ala Asp Thr Phe Tyr Phe
                805                 810                 815 gac gtt aaa gaa gac ggc gac gta acc att gag ctg ccg tac agc ggt    2496
Asp Val Lys Glu Asp Gly Asp Val Thr Ile Glu Leu Pro Tyr Ser Gly
            820                 825                 830 tcc tcc aac ttc acc tgg ttg gta tac aaa gaa ggt gac gac cag aac    2544
Ser Ser Asn Phe Thr Trp Leu Val Tyr Lys Glu Gly Asp Asp Gln Asn
        835                 840                 845 cac att gca tcg ggc att gat aaa aac aac agc aaa gtg ggc acc ttc    2592
His Ile Ala Ser Gly Ile Asp Lys Asn Asn Ser Lys Val Gly Thr Phe
    850                 855                 860 aaa tcc acc aaa ggt cgc cac tac gtc ttc att tac aaa cat gat tct    2640
Lys Ser Thr Lys Gly Arg His Tyr Val Phe Ile Tyr Lys His Asp Ser
865                 870                 875                 880 gcc tcg aac att agc tat tca ctc aac atc aaa ggt ctg ggt aac gaa    2688
Ala Ser Asn Ile Ser Tyr Ser Leu Asn Ile Lys Gly Leu Gly Asn Glu
                885                 890                 895 aag ctg aaa gaa aag gaa aat aac gat tct tcc gat aaa gca acc gtg    2736
Lys Leu Lys Glu Lys Glu Asn Asn Asp Ser Ser Asp Lys Ala Thr Val
            900                 905                 910 att ccg aac ttt aac acc act atg cag ggg tcg ctg ctg ggt gac gat    2784
Ile Pro Asn Phe Asn Thr Thr Met Gln Gly Ser Leu Leu Gly Asp Asp
        915                 920                 925 tcc cgc gat tat tac tcc ttc gaa gta aaa gaa gag ggc gaa gtg aac    2832
Ser Arg Asp Tyr Tyr Ser Phe Glu Val Lys Glu Glu Gly Glu Val Asn
    930                 935                 940 atc gaa ctg gat aaa aaa gac gaa ttt ggt gtt acc tgg acg ctg cac    2880
Ile Glu Leu Asp Lys Lys Asp Glu Phe Gly Val Thr Trp Thr Leu His
945                 950                 955                 960 ccg gaa tct aac atc aac gac cgt atc acc tat ggc cag gtg gac ggt    2928
Pro Glu Ser Asn Ile Asn Asp Arg Ile Thr Tyr Gly Gln Val Asp Gly
                965                 970                 975 aac aaa gtt tcc aac aag gtc aaa ctt cgc ccg ggc aaa tat tat ctg    2976
Asn Lys Val Ser Asn Lys Val Lys Leu Arg Pro Gly Lys Tyr Tyr Leu
            980                 985                 990 ctg gtc tac aag tat tct gga tct ggt aat tac gaa ctg cgt gtt aac    3024
Leu Val Tyr Lys Tyr Ser Gly Ser Gly Asn Tyr Glu Leu Arg Val Asn
        995                 1000                1005 aag taa                                                            3030
Lys
```

-continued

```
<210> SEQ ID NO 2
<211> LENGTH: 1009
<212> TYPE: PRT
<213> ORGANISM: Artificial Sequence
<220> FEATURE:
<223> OTHER INFORMATION: amino acid sequence coded by the sequence
      optimized for Escherichia coli K12, which is identical to the
      wild-type C. histolyticum ColG protein

<400> SEQUENCE: 2

Met Ile Ala Asn Thr Asn Ser Glu Lys Tyr Asp Phe Glu Tyr Leu Asn
1               5                   10                  15

Gly Leu Ser Tyr Thr Glu Leu Thr Asn Leu Ile Lys Asn Ile Lys Trp
            20                  25                  30

Asn Gln Ile Asn Gly Leu Phe Asn Tyr Ser Thr Gly Ser Gln Lys Phe
        35                  40                  45

Phe Gly Asp Lys Asn Arg Val Gln Ala Ile Ile Asn Ala Leu Gln Glu
    50                  55                  60

Ser Gly Arg Thr Tyr Thr Ala Asn Asp Met Lys Gly Ile Glu Thr Phe
65                  70                  75                  80

Thr Glu Val Leu Arg Ala Gly Phe Tyr Leu Gly Tyr Tyr Asn Asp Gly
                85                  90                  95

Leu Ser Tyr Leu Asn Asp Arg Asn Phe Gln Asp Lys Cys Ile Pro Ala
            100                 105                 110

Met Ile Ala Ile Gln Lys Asn Pro Asn Phe Lys Leu Gly Thr Ala Val
        115                 120                 125

Gln Asp Glu Val Ile Thr Ser Leu Gly Lys Leu Ile Gly Asn Ala Ser
    130                 135                 140

Ala Asn Ala Glu Val Val Asn Asn Cys Val Pro Val Leu Lys Gln Phe
145                 150                 155                 160

Arg Glu Asn Leu Asn Gln Tyr Ala Pro Asp Tyr Val Lys Gly Thr Ala
                165                 170                 175

Val Asn Glu Leu Ile Lys Gly Ile Glu Phe Asp Phe Ser Gly Ala Ala
            180                 185                 190

Tyr Glu Lys Asp Val Lys Thr Met Pro Trp Tyr Gly Lys Ile Asp Pro
        195                 200                 205

Phe Ile Asn Glu Leu Lys Ala Leu Gly Leu Tyr Gly Asn Ile Thr Ser
    210                 215                 220

Ala Thr Glu Trp Ala Ser Asp Val Gly Ile Tyr Tyr Leu Ser Lys Phe
225                 230                 235                 240

Gly Leu Tyr Ser Thr Asn Arg Asn Asp Ile Val Gln Ser Leu Glu Lys
                245                 250                 255

Ala Val Asp Met Tyr Lys Tyr Gly Lys Ile Ala Phe Val Ala Met Glu
            260                 265                 270

Arg Ile Thr Trp Asp Tyr Asp Gly Ile Gly Ser Asn Gly Lys Lys Val
        275                 280                 285

Asp His Asp Lys Phe Leu Asp Ala Glu Lys His Tyr Leu Pro Lys
    290                 295                 300

Thr Tyr Thr Phe Asp Asn Gly Thr Phe Ile Ile Arg Ala Gly Asp Lys
305                 310                 315                 320

Val Ser Glu Glu Lys Ile Lys Arg Leu Tyr Trp Ala Ser Arg Glu Val
                325                 330                 335

Lys Ser Gln Phe His Arg Val Val Gly Asn Asp Lys Ala Leu Glu Val
            340                 345                 350

Gly Asn Ala Asp Asp Val Leu Thr Met Lys Ile Phe Asn Ser Pro Glu
        355                 360                 365
```

-continued

Glu Tyr Lys Phe Asn Thr Asn Ile Asn Gly Val Ser Thr Asp Asn Gly
370                 375                 380

Gly Leu Tyr Ile Glu Pro Arg Gly Thr Phe Tyr Thr Tyr Glu Arg Thr
385                 390                 395                 400

Pro Gln Gln Ser Ile Phe Ser Leu Glu Glu Leu Phe Arg His Glu Tyr
            405                 410                 415

Thr His Tyr Leu Gln Ala Arg Tyr Leu Val Asp Gly Leu Trp Gly Gln
            420                 425                 430

Gly Pro Phe Tyr Glu Lys Asn Arg Leu Thr Trp Phe Asp Glu Gly Thr
            435                 440                 445

Ala Glu Phe Phe Ala Gly Ser Thr Arg Thr Ser Gly Val Leu Pro Arg
450                 455                 460

Lys Ser Ile Leu Gly Tyr Leu Ala Lys Asp Lys Val Asp His Arg Tyr
465                 470                 475                 480

Ser Leu Lys Lys Thr Leu Asn Ser Gly Tyr Asp Asp Ser Asp Trp Met
            485                 490                 495

Phe Tyr Asn Tyr Gly Phe Ala Val Ala His Tyr Leu Tyr Glu Lys Asp
            500                 505                 510

Met Pro Thr Phe Ile Lys Met Asn Lys Ala Ile Leu Asn Thr Asp Val
            515                 520                 525

Lys Ser Tyr Asp Glu Ile Ile Lys Lys Leu Ser Asp Asp Ala Asn Lys
530                 535                 540

Asn Thr Glu Tyr Gln Asn His Ile Gln Glu Leu Ala Asp Lys Tyr Gln
545                 550                 555                 560

Gly Ala Gly Ile Pro Leu Val Ser Asp Asp Tyr Leu Lys Asp His Gly
            565                 570                 575

Tyr Lys Lys Ala Ser Glu Val Tyr Ser Glu Ile Ser Lys Ala Ala Ser
            580                 585                 590

Leu Thr Asn Thr Ser Val Thr Ala Glu Lys Ser Gln Tyr Phe Asn Thr
            595                 600                 605

Phe Thr Leu Arg Gly Thr Tyr Thr Gly Glu Thr Ser Lys Gly Glu Phe
610                 615                 620

Lys Asp Trp Asp Glu Met Ser Lys Lys Leu Asp Gly Thr Leu Glu Ser
625                 630                 635                 640

Leu Ala Lys Asn Ser Trp Ser Gly Tyr Lys Thr Leu Thr Ala Tyr Phe
            645                 650                 655

Thr Asn Tyr Arg Val Thr Ser Asp Asn Lys Val Gln Tyr Asp Val Val
            660                 665                 670

Phe His Gly Val Leu Thr Asp Asn Ala Asp Ile Ser Asn Asn Lys Ala
            675                 680                 685

Pro Ile Ala Lys Val Thr Gly Pro Ser Thr Gly Ala Val Gly Arg Asn
690                 695                 700

Ile Glu Phe Ser Gly Lys Asp Ser Lys Asp Glu Asp Gly Lys Ile Val
705                 710                 715                 720

Ser Tyr Asp Trp Asp Phe Gly Asp Gly Ala Thr Ser Arg Gly Lys Asn
            725                 730                 735

Ser Val His Ala Tyr Lys Lys Ala Gly Thr Tyr Asn Val Thr Leu Lys
            740                 745                 750

Val Thr Asp Asp Lys Gly Ala Thr Ala Thr Glu Ser Phe Thr Ile Glu
            755                 760                 765

Ile Lys Asn Glu Asp Thr Thr Thr Pro Ile Thr Lys Glu Met Glu Pro
770                 775                 780

Asn Asp Asp Ile Lys Glu Ala Asn Gly Pro Ile Val Glu Gly Val Thr

-continued

```
785                 790                 795                 800

Val Lys Gly Asp Leu Asn Gly Ser Asp Asp Ala Asp Thr Phe Tyr Phe
                805                 810                 815

Asp Val Lys Glu Asp Gly Asp Val Thr Ile Glu Leu Pro Tyr Ser Gly
            820                 825                 830

Ser Ser Asn Phe Thr Trp Leu Val Tyr Lys Glu Gly Asp Asp Gln Asn
        835                 840                 845

His Ile Ala Ser Gly Ile Asp Lys Asn Asn Ser Lys Val Gly Thr Phe
    850                 855                 860

Lys Ser Thr Lys Gly Arg His Tyr Val Phe Ile Tyr Lys His Asp Ser
865                 870                 875                 880

Ala Ser Asn Ile Ser Tyr Ser Leu Asn Ile Lys Gly Leu Gly Asn Glu
                885                 890                 895

Lys Leu Lys Glu Lys Glu Asn Asn Asp Ser Ser Asp Lys Ala Thr Val
            900                 905                 910

Ile Pro Asn Phe Asn Thr Thr Met Gln Gly Ser Leu Leu Gly Asp Asp
        915                 920                 925

Ser Arg Asp Tyr Tyr Ser Phe Glu Val Lys Glu Glu Gly Glu Val Asn
    930                 935                 940

Ile Glu Leu Asp Lys Lys Asp Glu Phe Gly Val Thr Trp Thr Leu His
945                 950                 955                 960

Pro Glu Ser Asn Ile Asn Asp Arg Ile Thr Tyr Gly Gln Val Asp Gly
                965                 970                 975

Asn Lys Val Ser Asn Lys Val Lys Leu Arg Pro Gly Lys Tyr Tyr Leu
            980                 985                 990

Leu Val Tyr Lys Tyr Ser Gly Ser  Gly Asn Tyr Glu Leu  Arg Val Asn
        995                 1000                1005

Lys

<210> SEQ ID NO 3
<211> LENGTH: 2952
<212> TYPE: DNA
<213> ORGANISM: Artificial Sequence
<220> FEATURE:
<223> OTHER INFORMATION: sequence generated by optimization of the
      Clostridium histolyticum gene ColH for codon usage of genes highly
      expressed in Escherichia coli K12
<220> FEATURE:
<221> NAME/KEY: CDS
<222> LOCATION: (1)..(2952)

<400> SEQUENCE: 3 acc atg gtt caa aac gaa agc aaa cgt tac acc gtg agc tat ctg aag       48
Thr Met Val Gln Asn Glu Ser Lys Arg Tyr Thr Val Ser Tyr Leu Lys
1               5                   10                  15 acc ctg aat tac tac gac ctg gta gat ctg ctg gtc aag acg gaa atc       96
Thr Leu Asn Tyr Tyr Asp Leu Val Asp Leu Leu Val Lys Thr Glu Ile
            20                  25                  30 gag aac ctg ccg gac ctg ttc cag tat agt agc gat gcc aaa gag ttt      144
Glu Asn Leu Pro Asp Leu Phe Gln Tyr Ser Ser Asp Ala Lys Glu Phe
        35                  40                  45 tac ggg aac aaa acg cgc atg tcg ttc att atg gat gaa atc ggt cgc      192
Tyr Gly Asn Lys Thr Arg Met Ser Phe Ile Met Asp Glu Ile Gly Arg
    50                  55                  60 cgt gcc ccg cag tat acg gaa atc gat cat aaa ggg att cct act ctg      240
Arg Ala Pro Gln Tyr Thr Glu Ile Asp His Lys Gly Ile Pro Thr Leu
65                  70                  75                  80 gta gaa gtg gtc cgc gct ggg ttt tat ctg ggg ttt cac aat aaa gaa      288
Val Glu Val Val Arg Ala Gly Phe Tyr Leu Gly Phe His Asn Lys Glu
```

```
                    85                  90                  95
ctg aat gaa att aac aag cgt agt ttt aag gag cgc gtg att cca agc      336
Leu Asn Glu Ile Asn Lys Arg Ser Phe Lys Glu Arg Val Ile Pro Ser
            100                 105                 110 atc ctg gca atc cag aag aat ccg aac ttc aag ctg ggg acc gag gtg      384
Ile Leu Ala Ile Gln Lys Asn Pro Asn Phe Lys Leu Gly Thr Glu Val
        115                 120                 125 caa gat aaa atc gtc agt gcc act ggc ctg ctg gct ggc aat gag act      432
Gln Asp Lys Ile Val Ser Ala Thr Gly Leu Leu Ala Gly Asn Glu Thr
    130                 135                 140 gcc cca ccg gaa gtg gtc aat aac ttt acc ccg atc ctg caa gac tgc      480
Ala Pro Pro Glu Val Val Asn Asn Phe Thr Pro Ile Leu Gln Asp Cys
145                 150                 155                 160 att aaa aat att gat cgt tac gca ctg gat gat ctg aaa agc aaa gca      528
Ile Lys Asn Ile Asp Arg Tyr Ala Leu Asp Asp Leu Lys Ser Lys Ala
                165                 170                 175 ctg ttc aac gta ctg gct gca cct act tac gac att act gaa tat ctg      576
Leu Phe Asn Val Leu Ala Ala Pro Thr Tyr Asp Ile Thr Glu Tyr Leu
            180                 185                 190 cgc gct act aaa gaa aaa cca gaa aac acg cct tgg tat ggt aaa att      624
Arg Ala Thr Lys Glu Lys Pro Glu Asn Thr Pro Trp Tyr Gly Lys Ile
        195                 200                 205 gac ggt ttc att aat gaa ctg aag aag ctg gcc ctg tat ggg aaa atc      672
Asp Gly Phe Ile Asn Glu Leu Lys Lys Leu Ala Leu Tyr Gly Lys Ile
    210                 215                 220 aat gac aat aat agc tgg att atc gac aat ggg att tat cat atc gcg      720
Asn Asp Asn Asn Ser Trp Ile Ile Asp Asn Gly Ile Tyr His Ile Ala
225                 230                 235                 240 cct ctg ggg aaa ctg cat agc aac aat aag atc ggc att gag acc ctg      768
Pro Leu Gly Lys Leu His Ser Asn Asn Lys Ile Gly Ile Glu Thr Leu
                245                 250                 255 act gag gta atg aaa gta tac cca tat ctg tcg atg cag cat ctg caa      816
Thr Glu Val Met Lys Val Tyr Pro Tyr Leu Ser Met Gln His Leu Gln
            260                 265                 270 agc gca gat caa att aag cgc cat tat gac tcg aaa gat gct gaa ggt      864
Ser Ala Asp Gln Ile Lys Arg His Tyr Asp Ser Lys Asp Ala Glu Gly
        275                 280                 285 aat aag att ccg ctg gac aag ttc aaa aaa gag ggc aaa gaa aaa tat      912
Asn Lys Ile Pro Leu Asp Lys Phe Lys Lys Glu Gly Lys Glu Lys Tyr
    290                 295                 300 tgt ccg aag acc tat acg ttt gac gat ggt aaa gtg att att aaa gct      960
Cys Pro Lys Thr Tyr Thr Phe Asp Asp Gly Lys Val Ile Ile Lys Ala
305                 310                 315                 320 ggt gct cgc gtt gaa gaa gaa aaa gtc aaa cgt ctg tat tgg gct agc     1008
Gly Ala Arg Val Glu Glu Glu Lys Val Lys Arg Leu Tyr Trp Ala Ser
                325                 330                 335 aaa gaa gtg aat agc caa ttt ttt cgc gtc tat ggc att gat aaa cca     1056
Lys Glu Val Asn Ser Gln Phe Phe Arg Val Tyr Gly Ile Asp Lys Pro
            340                 345                 350 ctg gag gag ggt aat cca gat gat atc ctg acg atg gtc atc tat aat     1104
Leu Glu Glu Gly Asn Pro Asp Asp Ile Leu Thr Met Val Ile Tyr Asn
        355                 360                 365 agc ccg gaa gaa tat aaa ctg aac tcg gtc ctg tat ggt tac gac acg     1152
Ser Pro Glu Glu Tyr Lys Leu Asn Ser Val Leu Tyr Gly Tyr Asp Thr
    370                 375                 380 aac aac ggt ggc atg tat att gaa ccg gag ggc acg ttc ttt acg tac     1200
Asn Asn Gly Gly Met Tyr Ile Glu Pro Glu Gly Thr Phe Phe Thr Tyr
385                 390                 395                 400 gag cgt gaa gcc caa gag agc acg tat act ctg gaa gaa ctg ttc cgt     1248
Glu Arg Glu Ala Gln Glu Ser Thr Tyr Thr Leu Glu Glu Leu Phe Arg
```

```
                         405                      410                      415
cat gaa tat acg cac tac ctg caa ggg cgc tac gcg gtt cca ggt cag       1296
His Glu Tyr Thr His Tyr Leu Gln Gly Arg Tyr Ala Val Pro Gly Gln
                420                      425                      430 tgg ggc cgt acg aag ctg tac gat aac gac cgt ctg acc tgg tac gag       1344
Trp Gly Arg Thr Lys Leu Tyr Asp Asn Asp Arg Leu Thr Trp Tyr Glu
            435                      440                      445 gaa ggg ggc gct gaa ctg ttt gct ggt tcg acc cgt act agc ggt att       1392
Glu Gly Gly Ala Glu Leu Phe Ala Gly Ser Thr Arg Thr Ser Gly Ile
        450                      455                      460 ctg ccg cgc aaa agc att gta agc aac atc cac aac act acg cgc aac       1440
Leu Pro Arg Lys Ser Ile Val Ser Asn Ile His Asn Thr Thr Arg Asn
465                      470                      475                      480 aac cgt tat aaa ctg agc gat acc gtg cat agc aag tat ggc gcg tcg       1488
Asn Arg Tyr Lys Leu Ser Asp Thr Val His Ser Lys Tyr Gly Ala Ser
                485                      490                      495 ttt gag ttt tat aat tac gcg tgc atg ttc atg gac tat atg tac aac       1536
Phe Glu Phe Tyr Asn Tyr Ala Cys Met Phe Met Asp Tyr Met Tyr Asn
            500                      505                      510 aaa gac atg ggc att ctg aat aaa ctg aat gac ctg gcg aaa aat aac       1584
Lys Asp Met Gly Ile Leu Asn Lys Leu Asn Asp Leu Ala Lys Asn Asn
        515                      520                      525 gat gtt gac ggc tat gac aat tac atc cgc gat ctg agc agc aac tat       1632
Asp Val Asp Gly Tyr Asp Asn Tyr Ile Arg Asp Leu Ser Ser Asn Tyr
530                      535                      540 gca ctg aac gac aag tat cag gat cac atg caa gag cgc att gac aac       1680
Ala Leu Asn Asp Lys Tyr Gln Asp His Met Gln Glu Arg Ile Asp Asn
545                      550                      555                      560 tac gag aat ctg acg gtt ccg ttt gtt gcg gat gac tat ctg gtc cgc       1728
Tyr Glu Asn Leu Thr Val Pro Phe Val Ala Asp Asp Tyr Leu Val Arg
                565                      570                      575 cac gcg tat aaa aac cct aat gaa att tat agc gag att agc gag gtt       1776
His Ala Tyr Lys Asn Pro Asn Glu Ile Tyr Ser Glu Ile Ser Glu Val
            580                      585                      590 gcg aag ctg aaa gat gct aaa agc gaa gtc aag aaa agc cag tac ttc       1824
Ala Lys Leu Lys Asp Ala Lys Ser Glu Val Lys Lys Ser Gln Tyr Phe
        595                      600                      605 agt acg ttc act ctg cgt ggt agc tac acg ggc ggc gcg agc aaa ggc       1872
Ser Thr Phe Thr Leu Arg Gly Ser Tyr Thr Gly Gly Ala Ser Lys Gly
    610                      615                      620 aaa ctg gag gac cag aaa gcc atg aat aaa ttt att gat gac agc ctg       1920
Lys Leu Glu Asp Gln Lys Ala Met Asn Lys Phe Ile Asp Asp Ser Leu
625                      630                      635                      640 aag aag ctg gac acg tac agt tgg agc ggg tat aaa acg ctg act gct       1968
Lys Lys Leu Asp Thr Tyr Ser Trp Ser Gly Tyr Lys Thr Leu Thr Ala
                645                      650                      655 tat ttt acc aac tac aaa gta gat agc agc aac cgt gtt acc tat gat       2016
Tyr Phe Thr Asn Tyr Lys Val Asp Ser Ser Asn Arg Val Thr Tyr Asp
            660                      665                      670 gtt gtg ttc cac ggt tac ctg ccg aac gag ggt gat tcg aaa aat tcg       2064
Val Val Phe His Gly Tyr Leu Pro Asn Glu Gly Asp Ser Lys Asn Ser
        675                      680                      685 ctg cct tat ggc aaa att aac ggt acc tac aag ggc acg gag aaa gaa       2112
Leu Pro Tyr Gly Lys Ile Asn Gly Thr Tyr Lys Gly Thr Glu Lys Glu
    690                      695                      700 aag atc aaa ttt agc agc gaa ggc agc ttt gac ccg gat ggt aag att       2160
Lys Ile Lys Phe Ser Ser Glu Gly Ser Phe Asp Pro Asp Gly Lys Ile
705                      710                      715                      720 gtc agc tac gaa tgg gat ttt ggc gac ggt aac aaa agc aac gaa gaa       2208
Val Ser Tyr Glu Trp Asp Phe Gly Asp Gly Asn Lys Ser Asn Glu Glu
```

```
                   725                 730                 735
aac cca gaa cat agc tac gac aaa gtt ggc acc tat acc gtt aag ctg    2256
Asn Pro Glu His Ser Tyr Asp Lys Val Gly Thr Tyr Thr Val Lys Leu
            740                 745                 750 aaa gtg acc gat gac aag ggc gaa agc agt gtt agt acc acc acg gcg    2304
Lys Val Thr Asp Asp Lys Gly Glu Ser Ser Val Ser Thr Thr Thr Ala
            755                 760                 765 gag atc aag gat ctg agc gaa aac aaa ctg ccg gtg atc tat atg cac    2352
Glu Ile Lys Asp Leu Ser Glu Asn Lys Leu Pro Val Ile Tyr Met His
            770                 775                 780 gta ccg aaa tcg ggt gcg ctg aac cag aaa gtg gtg ttt tac ggc aag    2400
Val Pro Lys Ser Gly Ala Leu Asn Gln Lys Val Val Phe Tyr Gly Lys
785                 790                 795                 800 ggc act tac gat ccg gat ggt tcg att gca ggc tat cag tgg gat ttt    2448
Gly Thr Tyr Asp Pro Asp Gly Ser Ile Ala Gly Tyr Gln Trp Asp Phe
                805                 810                 815 ggc gat ggc agc gat ttc agt agc gag cag aat ccg tcg cac gtc tat    2496
Gly Asp Gly Ser Asp Phe Ser Ser Glu Gln Asn Pro Ser His Val Tyr
            820                 825                 830 acc aaa aaa ggc gaa tat acc gtt acc ctg cgc gtg atg gac tcg tcg    2544
Thr Lys Lys Gly Glu Tyr Thr Val Thr Leu Arg Val Met Asp Ser Ser
            835                 840                 845 ggc cag atg agt gag aaa act atg aag att aaa atc acc gac ccg gtt    2592
Gly Gln Met Ser Glu Lys Thr Met Lys Ile Lys Ile Thr Asp Pro Val
850                 855                 860 tac ccg att ggc acc gaa aaa gaa ccg aac aac agc aag gag acg gct    2640
Tyr Pro Ile Gly Thr Glu Lys Glu Pro Asn Asn Ser Lys Glu Thr Ala
865                 870                 875                 880 agc ggt ccg atc gtt ccg ggc atc ccg gtt agt ggc acc att gaa aat    2688
Ser Gly Pro Ile Val Pro Gly Ile Pro Val Ser Gly Thr Ile Glu Asn
                885                 890                 895 acc agc gac cag gac tat ttt tat ttt gat gtt att acc cca ggt gag    2736
Thr Ser Asp Gln Asp Tyr Phe Tyr Phe Asp Val Ile Thr Pro Gly Glu
            900                 905                 910 gtt aaa att gac att aac aaa ctg ggc tac ggc ggc gcc acc tgg gtc    2784
Val Lys Ile Asp Ile Asn Lys Leu Gly Tyr Gly Gly Ala Thr Trp Val
            915                 920                 925 gtg tat gat gaa aat aat aac gcg gtg agc tac gcg acc gat gac ggg    2832
Val Tyr Asp Glu Asn Asn Asn Ala Val Ser Tyr Ala Thr Asp Asp Gly
            930                 935                 940 cag aac ctg agc ggc aaa ttc aag gcc gat aaa ccg ggc cgc tac tat    2880
Gln Asn Leu Ser Gly Lys Phe Lys Ala Asp Lys Pro Gly Arg Tyr Tyr
945                 950                 955                 960 att cat ctg tat atg ttt aac ggc agc tat atg ccg tat cgc atc aat    2928
Ile His Leu Tyr Met Phe Asn Gly Ser Tyr Met Pro Tyr Arg Ile Asn
                965                 970                 975 atc gaa ggc agc gtg ggc cgc taa                                    2952
Ile Glu Gly Ser Val Gly Arg
            980

<210> SEQ ID NO 4
<211> LENGTH: 983
<212> TYPE: PRT
<213> ORGANISM: Artificial Sequence
<220> FEATURE:
<223> OTHER INFORMATION: amino acid sequence coded by the sequence
      optimized for Escherichia coli K12, which is identical to the
      wild-type C. histolyticum ColH protein

<400> SEQUENCE: 4

Thr Met Val Gln Asn Glu Ser Lys Arg Tyr Thr Val Ser Tyr Leu Lys
1               5                   10                  15
```

Thr Leu Asn Tyr Tyr Asp Leu Val Asp Leu Val Lys Thr Glu Ile
                20                  25                  30

Glu Asn Leu Pro Asp Leu Phe Gln Tyr Ser Ser Asp Ala Lys Glu Phe
            35                  40                  45

Tyr Gly Asn Lys Thr Arg Met Ser Phe Ile Met Asp Glu Ile Gly Arg
 50                  55                  60

Arg Ala Pro Gln Tyr Thr Glu Ile Asp His Lys Gly Ile Pro Thr Leu
 65                  70                  75                  80

Val Glu Val Val Arg Ala Gly Phe Tyr Leu Gly Phe His Asn Lys Glu
                85                  90                  95

Leu Asn Glu Ile Asn Lys Arg Ser Phe Lys Glu Arg Val Ile Pro Ser
            100                 105                 110

Ile Leu Ala Ile Gln Lys Asn Pro Asn Phe Lys Leu Gly Thr Glu Val
        115                 120                 125

Gln Asp Lys Ile Val Ser Ala Thr Gly Leu Leu Ala Gly Asn Glu Thr
130                 135                 140

Ala Pro Pro Glu Val Val Asn Asn Phe Thr Pro Ile Leu Gln Asp Cys
145                 150                 155                 160

Ile Lys Asn Ile Asp Arg Tyr Ala Leu Asp Leu Lys Ser Lys Ala
                165                 170                 175

Leu Phe Asn Val Leu Ala Ala Pro Thr Tyr Asp Ile Thr Glu Tyr Leu
            180                 185                 190

Arg Ala Thr Lys Glu Lys Pro Glu Asn Thr Pro Trp Tyr Gly Lys Ile
        195                 200                 205

Asp Gly Phe Ile Asn Glu Leu Lys Lys Leu Ala Leu Tyr Gly Lys Ile
210                 215                 220

Asn Asp Asn Asn Ser Trp Ile Ile Asp Asn Gly Ile Tyr His Ile Ala
225                 230                 235                 240

Pro Leu Gly Lys Leu His Ser Asn Asn Lys Ile Gly Ile Glu Thr Leu
                245                 250                 255

Thr Glu Val Met Lys Val Tyr Pro Tyr Leu Ser Met Gln His Leu Gln
            260                 265                 270

Ser Ala Asp Gln Ile Lys Arg His Tyr Asp Ser Lys Asp Ala Glu Gly
        275                 280                 285

Asn Lys Ile Pro Leu Asp Lys Phe Lys Lys Glu Gly Lys Glu Lys Tyr
290                 295                 300

Cys Pro Lys Thr Tyr Thr Phe Asp Asp Gly Lys Val Ile Ile Lys Ala
305                 310                 315                 320

Gly Ala Arg Val Glu Glu Lys Val Lys Arg Leu Tyr Trp Ala Ser
                325                 330                 335

Lys Glu Val Asn Ser Gln Phe Phe Arg Val Tyr Gly Ile Asp Lys Pro
            340                 345                 350

Leu Glu Glu Gly Asn Pro Asp Asp Ile Leu Thr Met Val Ile Tyr Asn
        355                 360                 365

Ser Pro Glu Glu Tyr Lys Leu Asn Ser Val Leu Tyr Gly Tyr Asp Thr
370                 375                 380

Asn Asn Gly Gly Met Tyr Ile Glu Pro Glu Gly Thr Phe Phe Thr Tyr
385                 390                 395                 400

Glu Arg Glu Ala Gln Glu Ser Thr Tyr Thr Leu Glu Glu Leu Phe Arg
                405                 410                 415

His Glu Tyr Thr His Tyr Leu Gln Gly Arg Tyr Ala Val Pro Gly Gln
            420                 425                 430

Trp Gly Arg Thr Lys Leu Tyr Asp Asn Asp Arg Leu Thr Trp Tyr Glu

```
                435                 440                 445
Glu Gly Gly Ala Glu Leu Phe Ala Gly Ser Thr Arg Thr Ser Gly Ile
450                 455                 460

Leu Pro Arg Lys Ser Ile Val Ser Asn Ile His Asn Thr Thr Arg Asn
465                 470                 475                 480

Asn Arg Tyr Lys Leu Ser Asp Thr Val His Ser Lys Tyr Gly Ala Ser
                485                 490                 495

Phe Glu Phe Tyr Asn Tyr Ala Cys Met Phe Met Asp Tyr Met Tyr Asn
                500                 505                 510

Lys Asp Met Gly Ile Leu Asn Lys Leu Asn Asp Leu Ala Lys Asn Asn
            515                 520                 525

Asp Val Asp Gly Tyr Asp Asn Tyr Ile Arg Asp Leu Ser Ser Asn Tyr
530                 535                 540

Ala Leu Asn Asp Lys Tyr Gln Asp His Met Gln Glu Arg Ile Asp Asn
545                 550                 555                 560

Tyr Glu Asn Leu Thr Val Pro Phe Val Ala Asp Asp Tyr Leu Val Arg
                565                 570                 575

His Ala Tyr Lys Asn Pro Asn Glu Ile Tyr Ser Glu Ile Ser Glu Val
                580                 585                 590

Ala Lys Leu Lys Asp Ala Lys Ser Glu Val Lys Lys Ser Gln Tyr Phe
            595                 600                 605

Ser Thr Phe Thr Leu Arg Gly Ser Tyr Thr Gly Gly Ala Ser Lys Gly
610                 615                 620

Lys Leu Glu Asp Gln Lys Ala Met Asn Lys Phe Ile Asp Asp Ser Leu
625                 630                 635                 640

Lys Lys Leu Asp Thr Tyr Ser Trp Ser Gly Tyr Lys Thr Leu Thr Ala
                645                 650                 655

Tyr Phe Thr Asn Tyr Lys Val Asp Ser Ser Asn Arg Val Thr Tyr Asp
                660                 665                 670

Val Val Phe His Gly Tyr Leu Pro Asn Glu Gly Asp Ser Lys Asn Ser
            675                 680                 685

Leu Pro Tyr Gly Lys Ile Asn Gly Thr Tyr Lys Gly Thr Glu Lys Glu
690                 695                 700

Lys Ile Lys Phe Ser Ser Glu Gly Ser Phe Asp Pro Asp Gly Lys Ile
705                 710                 715                 720

Val Ser Tyr Glu Trp Asp Phe Gly Asp Gly Asn Lys Ser Asn Glu Glu
                725                 730                 735

Asn Pro Glu His Ser Tyr Asp Lys Val Gly Thr Tyr Thr Val Lys Leu
                740                 745                 750

Lys Val Thr Asp Asp Lys Gly Glu Ser Ser Val Ser Thr Thr Thr Ala
            755                 760                 765

Glu Ile Lys Asp Leu Ser Glu Asn Lys Leu Pro Val Ile Tyr Met His
770                 775                 780

Val Pro Lys Ser Gly Ala Leu Asn Gln Lys Val Val Phe Tyr Gly Lys
785                 790                 795                 800

Gly Thr Tyr Asp Pro Asp Gly Ser Ile Ala Gly Tyr Gln Trp Asp Phe
                805                 810                 815

Gly Asp Gly Ser Asp Phe Ser Ser Glu Gln Asn Pro Ser His Val Tyr
                820                 825                 830

Thr Lys Lys Gly Glu Tyr Thr Val Thr Leu Arg Val Met Asp Ser Ser
            835                 840                 845

Gly Gln Met Ser Glu Lys Thr Met Lys Ile Lys Ile Thr Asp Pro Val
850                 855                 860
```

```
Tyr Pro Ile Gly Thr Glu Lys Glu Pro Asn Asn Ser Lys Glu Thr Ala
865                 870                 875                 880

Ser Gly Pro Ile Val Pro Gly Ile Pro Val Ser Gly Thr Ile Glu Asn
                885                 890                 895

Thr Ser Asp Gln Asp Tyr Phe Tyr Phe Asp Val Ile Thr Pro Gly Glu
            900                 905                 910

Val Lys Ile Asp Ile Asn Lys Leu Gly Tyr Gly Gly Ala Thr Trp Val
        915                 920                 925

Val Tyr Asp Glu Asn Asn Asn Ala Val Ser Tyr Ala Thr Asp Asp Gly
    930                 935                 940

Gln Asn Leu Ser Gly Lys Phe Lys Ala Asp Lys Pro Gly Arg Tyr Tyr
945                 950                 955                 960

Ile His Leu Tyr Met Phe Asn Gly Ser Tyr Met Pro Tyr Arg Ile Asn
                965                 970                 975

Ile Glu Gly Ser Val Gly Arg
                980

<210> SEQ ID NO 5
<211> LENGTH: 6
<212> TYPE: PRT
<213> ORGANISM: Artificial sequence
<220> FEATURE:
<223> OTHER INFORMATION: collagenase cutting site between Xaa and Gly
<220> FEATURE:
<221> NAME/KEY: misc_feature
<222> LOCATION: (1)..(1)
<223> OTHER INFORMATION: Xaa can be any natural amino acid
<220> FEATURE:
<221> NAME/KEY: misc_feature
<222> LOCATION: (3)..(3)
<223> OTHER INFORMATION: Xaa can be any natural amino acid
<220> FEATURE:
<221> NAME/KEY: misc_feature
<222> LOCATION: (6)..(6)
<223> OTHER INFORMATION: Xaa can be any natural amino acid

<400> SEQUENCE: 5

Xaa Pro Xaa Gly Pro Xaa
1               5
```

CLOSTRIDIUM HISTOLYTICUM RECOMBINANT COLLAGENASES AND METHOD FOR THE MANUFACTURE THEREOF

This application is the U.S. national phase of International Application No. PCT/IB2010/055840, filed 15 Dec. 2010, which designated the U.S. and claims priority to IT RM2009A000661 filed 15 Dec. 2009; the entire contents of each of which are hereby incorporated by reference.

The present invention relates to the production of recombinant collagenases, and in particular describes a method for the production of recombinant *clostridium histolyticum* collagenases Col characterized by a yield higher than approximately 140 mg/l of culture of said collagenases in soluble, biologically active form, collagenases produced by this method, compositions comprising these collagenases and the use thereof.

PRIOR ART

*Clostridium histolyticum* collagenases are enzymes which are able to digest collagen fibres and are used widely within the field of medicine as a result of their ability to disaggregate connective tissue and to enable the isolation of cells of interest from various tissues. In particular, collagenases produced from the bacteria *C. histolyticum* are preferred since they are able to hydrolyze practically all collagen isoforms, even in native form. Their success is also linked to the present production method based on the culture of the productive bacteria *C. histolyticum* which is characterized by very high yields. The procedures currently used for the production of collagenases for medical use are based on the culture of *C. histolyticum* and the subsequent purification thereof from all the bacterial proteins produced.

The biochemical features of the collagenase preparations which are currently commercially available have been fully analyzed, above all in light of the various problems found during their use.

In particular, the biological and enzymatic properties of crude *C. histolyticum* collagenase have been assessed, highlighting the presence of at least six main collagenolytic isoforms. Based on the specificity for the substrate and on the amino acid sequence, the various isoforms are grouped into class I collagenases ($\alpha$, $\beta$, $\gamma$) and class II collagenases ($\delta$, $\epsilon$, $\zeta$). Class I and class II collagenases are known in *C. histolyticum* and are known also by the name of collagenases ColG and collagenases ColH, and are coded respectively by the colG and colH genes. The $\beta$ collagenase is the isoform of higher molecular weight within class I and it is believed that the other isoforms of lower molecular weight, i.e. the $\alpha$ collagenases and $\gamma$ collagenases, are derived from the $\beta$ collagenase truncated at the C-terminal region. Similarly, the $\zeta$ collagenase is the isoform of higher molecular weight among those of class II, and the $\delta$ and $\epsilon$ collagenases are derived from the $\zeta$ collagenases truncated at the C-terminal. In particular, in the literature the expression 'crude collagenase' therefore means a mixture of at least 12 different components, among which the collagenases represent the main constituents in terms of activity and quantity. Apart from all collagenases in the strict sense, at least 10 other active components such as: clostripin, trypsin, neutral protease, elastase, $\beta$-D-galactosidase, $\beta$-N-acetyl-D-glucosaminidase, a-L-fucosidase, phospholipase, neuroaminidase and hyaluronidase can be found in crude collagenase.

These contaminating components are not only harmful to the cells isolated by the use of crude collagenase, but it is believed that they are also responsible for the deterioration of crude collagenase during storage (Johnson et al., 1996). It follows from the above that both the composition and activity of crude collagenase preparations vary widely from batch to batch. This variability is currently considered to be the major obstacle for effective isolation of cells and, in particular, of human pancreatic islets (Kin et al., 2007). The problem regarding the variability of batches seems to be closely linked to the method of production of crude collagenase, based (as already indicated above) on the culture *C. histolyticum*. In fact, this method does not allow effective control, in terms of composition, of the various mixtures obtained with a consequent presence in various batches, in addition to contaminants, of non-uniform percentage ratios between the various collagenase classes, which therefore hinders standardization of the extraction protocols of cells from the tissues with the consequent drawbacks evident in the prior art (protocol has to be calibrated from batch to batch, experimental yield cannot be standardized, possible loss of precious biological material).

In addition to the above, even the minimal hydration accompanying the freezing-thawing cycles of the lyophilized product between different cellular isolation procedures, may cause deterioration of the collagenase function. In fact, hydration determines activation of the proteases within the crude collagenase and these proteases cause degradation of collagenases of high molecular weight.

Given the objective problems illustrated above, a new enzyme mixture called Liberase HI (Roche Applied Science, Indianapolis, Ind.) aimed at eliminating the problem of variability and enzyme efficiency from batch to batch has been introduced onto the market. This new product is still a mixture of enzymes obtained by culturing the *C. histolyticum* bacteria, but in this instance the enzymes are highly purified and therefore it contains class I and class II collagenases with a low content of bacterial endotoxins.

The use of this product has brought about improvements in terms of the yield of extractable cells in animal and human models. It can be deduced from recent literature that, with regard to the clinical isolation of pancreatic islets, Liberase HI is the most widely used commercially available enzyme mixture (Kin et al., 2007). However, it does not solve the problem of batch variability. In fact, Kin et al have demonstrated that the success rate for the isolation of cells of interest fluctuates between 0% and 75% and is extremely dependent on the enzyme batch (Kin et al., 2007).

In addition, recent studies have shown that Liberase HI is not more effective compared to crude collagenase in experiments on the pancreas of new-born rats and pig foetuses and that it induces functional damage both to rat and human islets (Vargas et al., 2001; Balamurugan et al., 2005). Furthermore, the production of Liberase HI using *C. histolyticum* culture requires the use, in growth media, of bovine heart and brain homogenates which have been proven to be associated with the risk of transmission of prion disease (Kin et al., 2008).

The need to obtain pure collagenase compositions devoid of toxic contaminants and at the same time capable of ensuring reproducible results using different batches has led researchers to develop alternative strategies compared to those described above.

Patent application US 2008/0233614 describes a method for maximizing the expression levels of collagenases and, in particular, of *C. histolyticum* collagenase ColG and collagenase ColH in *E. coli* bacteria. Such a method consists in the optimization of the nucleotide sequences of the *C. histolyticum* ColG and ColH genes by the substitution of a small number of codons. As is known from scientific literature each organism uses, in its cell translation machinery, preferential codons for the expression of each amino acid. This preference of use forms the basis of the optimization process which consists in the substitution of one or more codons coding for specific amino acids and present in the wild gene sequence but rarely used by said microorganism. The authors specify a collagenase expression of approximately 140 mg/l of bacterial culture but there is actually no indication as to what fraction (only the soluble fraction? soluble and insoluble fractions?) of this 140 mg/l of culture is in the active form. As reported, it is understood that there are problems regarding the attainment of soluble forms of the recombinant proteins produced. In particular, it is indicated that the soluble fraction produces only approximately 75% of expressed ColH and therefore, assuming that the 140 mg/l of culture refer merely to the soluble fraction, approximately 105 mg/l of expressed ColH, and therefore approximately 35% of expressed ColG (corresponding to approximately 49 mg/l assuming that the 140 mg/l of culture refer merely to the soluble fraction) without providing, furthermore, any information relating to the biological activity of the expressed recombinant proteins. Lastly, this document teaches that the maximum expression of collagenase is obtained with bacterial cultures carried out at a temperature of 37° C. rather than at 30° C.

Patent application WO 94/00580 describes the expression in *E. coli* of native and non-native collagenases, the characterization and purification of which is not explained in the specification, and describes an amino acid sequence of recombinant collagenases devoid of the signal peptide and of 73 amino acids which map in the prodomain of collagenase 1 of *C. histolyticum* available in the literature.

Ducka and colleagues (Ducka et al., 2009) illustrate in their work, following comparative tests carried out by them on various parameters (for example *E. coli* strain, inducer concentration, temperature of the bacterial culture), an optimal strategy for obtaining soluble forms of *E. coli* collagenase. The authors identify precisely that the optimal conditions for the expression of the wild ColG and ColH genes are the use of the BL21 strain as a host, a concentration of inducer (IPTG) of approximately 0.1 mM and a temperature of 25° C. According to data reported by the same authors, this optimal expression is evidenced by a yield of approximately 10 mg of recombinant protein per 1 L of bacterial culture.

As evidenced above, there are thus various objective problems in the production of *C. histolyticum*, more specifically problems of purification which render the preparations inhomogeneous for technical, medical and scientific use, and problems of production linked to the amount of enzyme produced and to the possible presence of contaminants in the culture which are potentially very harmful to human and animal health, as discussed above.

In particular, it emerges from the prior art that, for an increased production of enzyme, it is necessary to cultivate *C. histolyticum* (therefore problems of contamination), whereas with recombinant expression systems and hosts purer enzymes are obtained which are devoid of dangerous contaminants but are produced in doses at least seven times lower than those obtained with *C. histolyticum* culture.

It is clear that improvements in the yield, safety and reliability of *C. histolyticum* collagenase are highly desirable given the extremely beneficial medical use of these enzymes (for example transplant of islets of pancreatic cells for the treatment of diabetes).

SUMMARY OF THE INVENTION

As detailed above, the prior art basically describes two methods for the production of *C. histolyticum* collagenase consisting, respectively, in a method of productive bacteria culture and a method based on recombinant DNA technology. The method for production of collagenase using *C. histolyticum* culture is characterized by a good yield, but leads to an unreliable product which is potentially harmful to human and animal health owing to the presence of contaminants such as prion proteins. The methods for production of recombinant collagenases documented in the known prior art ensure greater safety of the product, but are characterized by a limited productive yield and/or limited collagenolytic activity.

The present description relates to the production of recombinant collagenases and describes a method for the production of recombinant *Clostridium histolyticum* collagenases (Col) characterized by a yield higher than approximately 140 mg/l of culture of said collagenases in soluble, enzimatically active form, recombinant collagenases characterized in that the cells extracted thereby maintain the differentiated phenotype, and in that they can be produced using said method, the use thereof and compositions comprising at least one of said collagenases.

The present description provides a method for the production of recombinant collagenases, in which product safety (absence of animal contaminants), product quality (absence of protease contaminants) and a yield of active collagenase greater than that described previously (prior art, maximum production calculated with the best hypotheses, as indicated above, as 140 mg/l of culture, active ColH (soluble) 75%, that is to say approximately 105 mg/l of culture and active ColG (soluble) 35%, that is to say approximately 49 mg/l) are obtained.

This description discloses, for the first time, a method for the production of *C. histolyticum* recombinant collagenase in biologically active, soluble form with a yield higher than approximately 140 mg/l of culture.

The present description therefore relates to:

a method for the production of biologically active *C. histolyticum* recombinant collagenase comprising the steps of:

a) designing a nucleotide sequence optimized for the expression of said collagenase of *C. histolyticum;* b) introducing, in an inducible expression vector, an oligonucleotide sequence coding for a fusion protein, wherein said oligonucleotide sequence consists in said optimized sequence fused, via a binding sequence coding for at least one enzyme cut site, to a nucleotide sequence coding for a soluble polypeptide and wherein said oligonucleotide sequence is operatively linked to an inducible promoter sequence, a transcription start sequence and a termination sequence;

c) transforming a bacterial strain defective in the expression of endogenous proteases with said expression vector;

d) culturing said transformed bacterial strain at a temperature comprised in a range of 28-32° C., extremes included;

e) inducing the expression of said fusion protein by adding a suitable inducer in said bacterial strain;

f) extracting the fusion protein obtained at point e), and g) purifying said fusion protein;

wherein said method provides a yield higher than approximately 140 mg/l of culture of said collagenase in soluble and enzymatically active form.

*C. histolyticum* recombinant collagenases wherein cells extracted with said collagenases can maintain the differentiated phenotype;

*C. histolyticum* recombinant collagenases wherein cells extracted with said collagenases obtainable by said method can maintain the differentiated phenotype;

compositions comprising said *C. histolyticum* recombinant collagenases in enzymatically active form obtainable by said method;

use of said *C. histolyticum* collagenases in procedures for the extraction of stem and/or somatic living cells from tissues.

GLOSSARY

Transformed bacteria. For the purposes of the present description, 'transformed bacteria' means bacteria in which exogenous genetic material inherited by the offspring is introduced by methods known to the person skilled in the art.

Enzymatically or biologically active. In the present description 'biologically active' means a protein exhibiting enzymatic collagenase activity, more specifically consisting in the ability to recognize and digest various collagen isoforms.

Recombinant collagenase. For the purposes of the present description, 'recombinant collagenase' means endogenous proteins of *Clostridium histolyticum*, produced in a host cell which is different to the *Clostridium histolyticum* bacteria, which hydrolyze collagens, in particular proteins that hydrolyze the Xaa-Gly bond in the SEQ ID 5 sequence: Xaa-Pro-Xaa-Gly-Pro-Xaa in which Xaa is any amino acid.

Normal phenotype. In the present description 'normal phenotype' means a phenotype relative to the extracted cells which is characterized by the ability of said cells to form stable cell-cell contacts so as to form a differentiated pseudo-epithelium.

Control sequence means a signal sequence of which the purpose consists in controlling processes such as: transcription and translation of a nucleotide sequence, generally coding for a protein of interest, within a host cell for example: promoter, enhancer, polyadenylation signal, transcription termination signal, transcription start signal, operator sequence; a binding site for the ribosome, a sequence coding for a repressor, an origin of replication and all the sequences known in the literature.

Binding sequence. In the present description 'binding sequence' means a DNA sequence containing at least one cut site for a restriction enzyme and of which the purpose consists in joining together, in the correct reading frame, two nucleotide sequences having specific coding functions.

Optimized nucleotide sequence. For the purposes of the present invention 'optimized nucleotide sequence' means a nucleotide sequence obtained by substituting one or more codons coding for specific amino acids, present in the corresponding wild sequence, with a nucleotide codon coding for the same amino acid that is used most frequently by the organism in which it is desired to express the optimized sequence.

Fusion protein. In this instance 'fusion protein' means a recombinant protein given by the expression of a chimeric DNA sequence coding, in the correct reading frame ('in frame'), for a protein of interest bound together with another protein or peptide (having a function useful to the researcher, for example facilitating purification of the protein of interest or the like).

pMAL-ColG—pMAL-ColH or MBP-ColG—MBP-ColH when referring to proteins they are used as synonyms and denote recombinant ColG or ColH proteins of *C. histolyticum* fused at their N terminal with the maltose binding protein (MBP). In the present description, pMAL-ColG and pMAL-ColH are also used with reference to the structure in the pMAL vector.

Purification tag. In the present description, as in the scientific literature, the expression 'purification tag' refers to an amino acid sequence coding for a peptide or a protein which, fused to a desired protein, enables simple purification, for example by the use of resins with a specific affinity for the purification tag. Numerous purification tags are known in the literature.

Operatively bound. For the purposes of the present description, the expression 'operatively bound' with regard to a sequence means a nucleotide sequence, generally coding for a protein of interest, arranged in functional relation to control nucleotide sequences in such a way that said nucleotide sequence of interest can be transcribed and translated, when trans-spliced, in a host cell.

Inducible expression vector. The expression 'inducible expression vector' means a vector which, apart from enabling the expression of a desired protein within a host cell, makes it possible to control the duration and levels of said expression by using suitable inducers.

In vitro cellular extraction assay. In the present description the method called 'in vitro cellular extraction assay' means the assay carried out as described hereinafter: 50 µl of a type-I collagen solution are stratified in each well of a 96-well plate in 0.02 N of $CH_3COOH$ diluted 1:1 with culture medium containing 10% foetal bovine serum, 50 mM of $H_2CO_3$ at pH 7.4, antibiotics and glutamine; this is then incubated at 37° C. for 30 minutes so as to promote polymerization. A second gel is stratified on this first gel, always with a final volume of 50 µl and of the same composition, but in which the epithelial cells ECV304 have been dissolved at a concentration of $1 \times 10^6$ ml; in this case also the gel is made to polymerase at 37° C. for 30 minutes. Once polymerization has occurred, 200 µl of culture medium containing 10% foetal bovine serum, antibiotics and glutamine are added and the cells are grown and differentiated in structures similar to blood vessels for 48 hours in incubators at 37° C., 5% $CO_2$. At this point the culture medium is substituted with a fresh one which does not contain foetal bovine serum, which will contain the enzymes of which the extraction efficiency is sought to be assessed. If the enzymes to be assayed are recombinant collagenase G and recombinant collagenase H produced by the method described herein, the New Liberase (Roche) and collagenase P (Roche), then these enzymes are added to the culture medium at a concentration of 0.5 mg/ml. Digestion is maintained for 2 hours at 37° C.; and therefore blocked by the removal of the medium culture and the positioning of the plate on a 'gel bed': the undigested gel portions are then removed by washing with PBS containing $Ca^{++}$ and $Mg^{++}$ and the cells adhered to the base of the well are counted.

The cells are then assayed for vitality by dyeing with SYTO 13/Et-Br.

DETAILED DESCRIPTION OF THE FIGURES

FIG. 1: shows a map of the inducible expression vector pMAL-c2X. The Col optimizer can code indifferently for the *C. histolyticum* collagenase ColG of *C. histolyticum* collagenase ColH.

Figure 2:
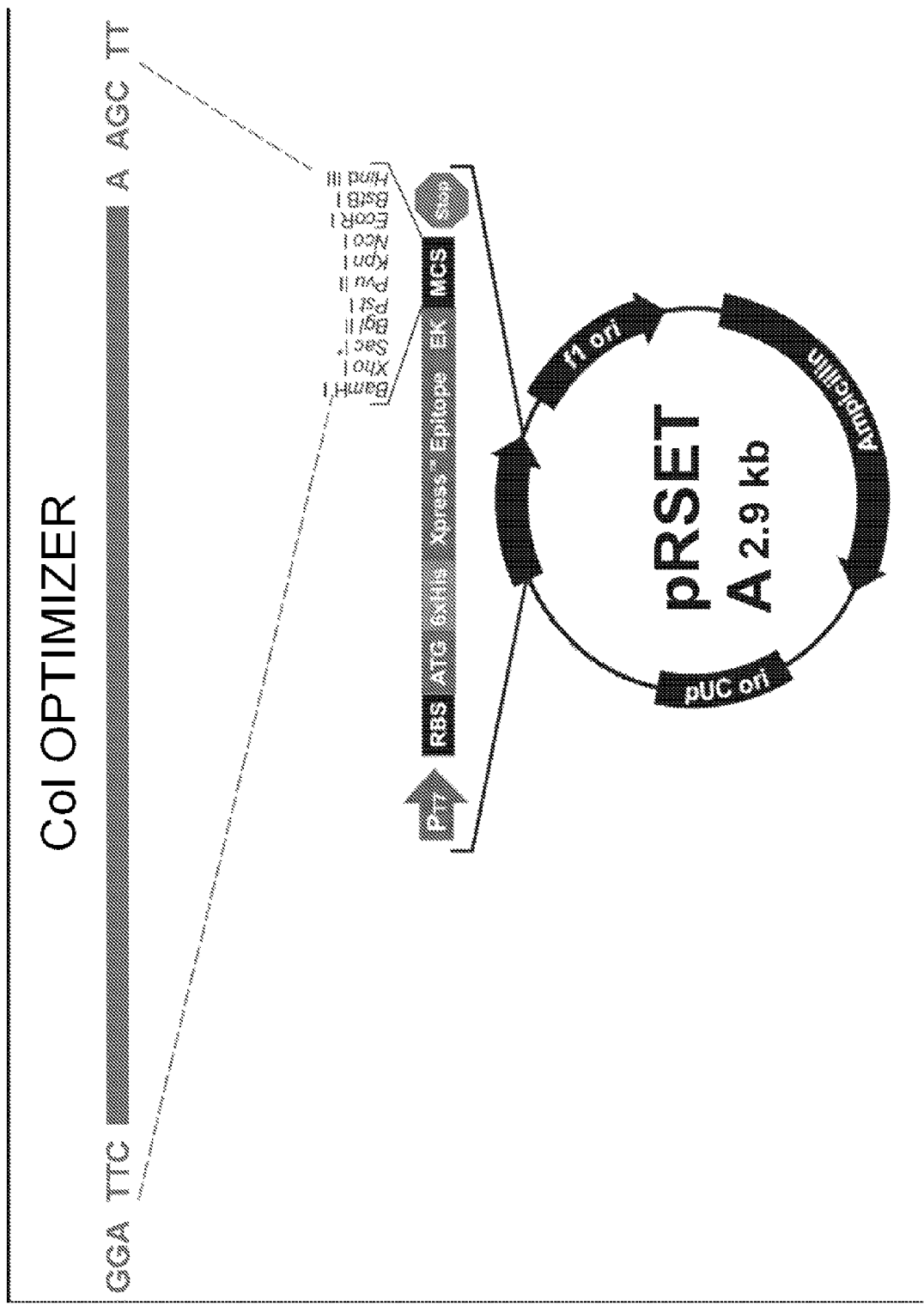

FIG. 2: shows a map of the inducible expression vector pRSET-A. The Col optimizer can code indifferently for the *C. histolyticum* collagenase ColG or *C. histolyticum* collagenase ColH.

Figure 3:
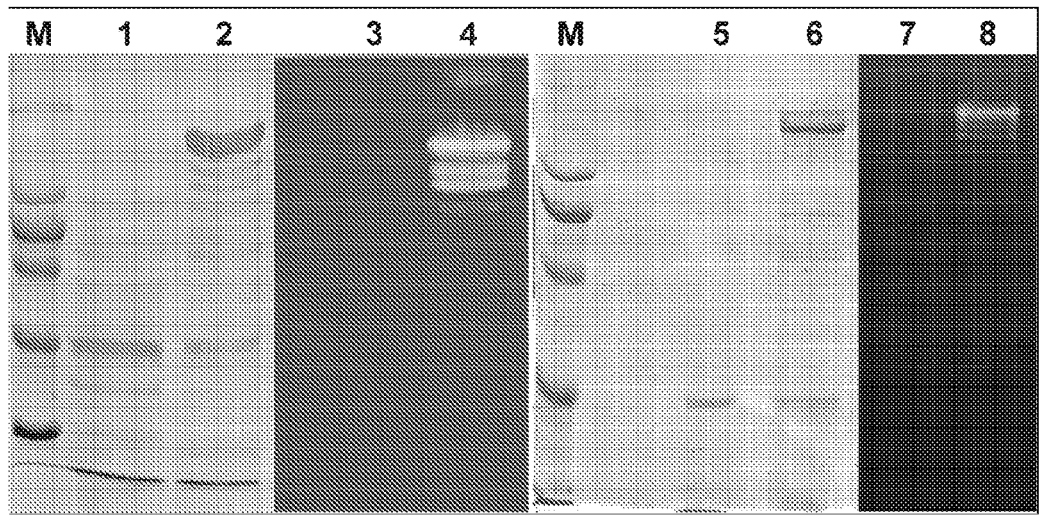

FIG. 3: Analyses using SDS-PAGE 7.5% and gelatine zymography 7.5% of the pMAL-col G and pMAL-col H induced proteins, i.e. the proteins formed in the pMAL vector which then create the MPB-Col H or MBP-Col G fusion proteins.

The figure shows the electrophoretic and zymographic profiles of the bacterial extracts obtained from bacteria transspliced with the only plasmids not containing the structures (line 1 and line 5, SDS-PAGE analyses; line 3 and line 7, analyses by zymography); and those containing the pMAL-col G and pMAL-col H fusion proteins (line 2 and line 6, SDS-PAGE analysis of pMAL-col G and pMAL-col H respectively; line 4 and line 8, analysis of pMAL-col G and pMAL-col H respectively by gelatine zymography). Markers of known molecular weight are present in line M (from top to bottom; 205-116-97.4-66-54-45 kDA respectively)

Figure 4:
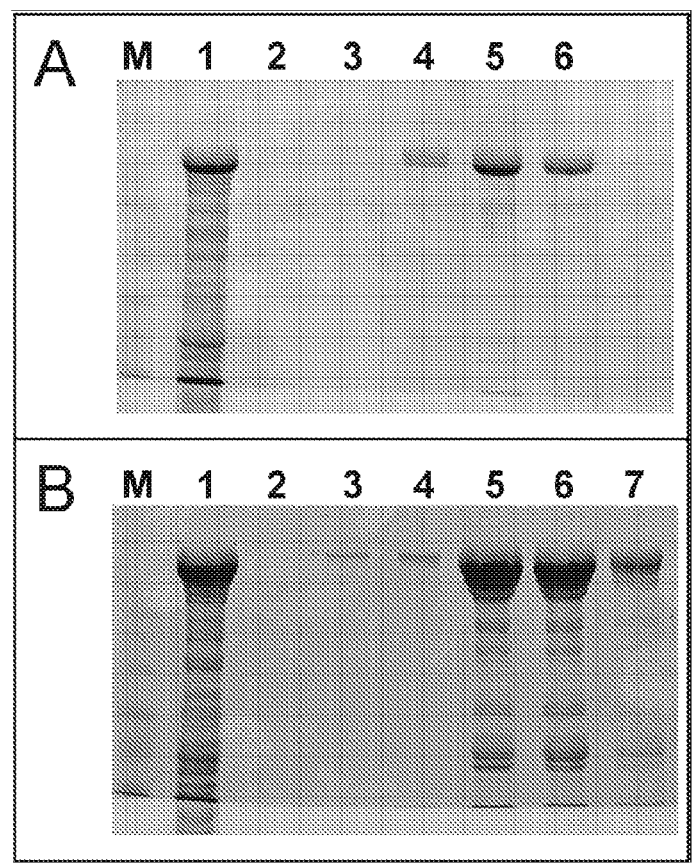

FIG. 4: Purification of pMAL-col G and pMAL-col H, that is to say of the proteins produced in the pMAL vector which then create the MPB-col H or MBP-Col G fusion proteins by amylose resin affinity chromatography (Biolabs).

The bacterial extracts producing pMAL-col G and pMAL-col H were pre-absorbed on an amylose resin and then eluted with a 10 mM maltose solution, various fractions were collected and analyzed using SDS-PAGE 7.5%.

In image A: pMAL-col G purification; in image B: pMAL-col H purification.

In lines 1A and 1B total extracts of those induced; from line 2 onwards fractions eluted using treatment with a buffer containing 10 mM maltose.

Markers of known molecular weight are present in line M (from top to bottom; 205-116-97.4 66-54-45 kDa respectively).

Figure 5:
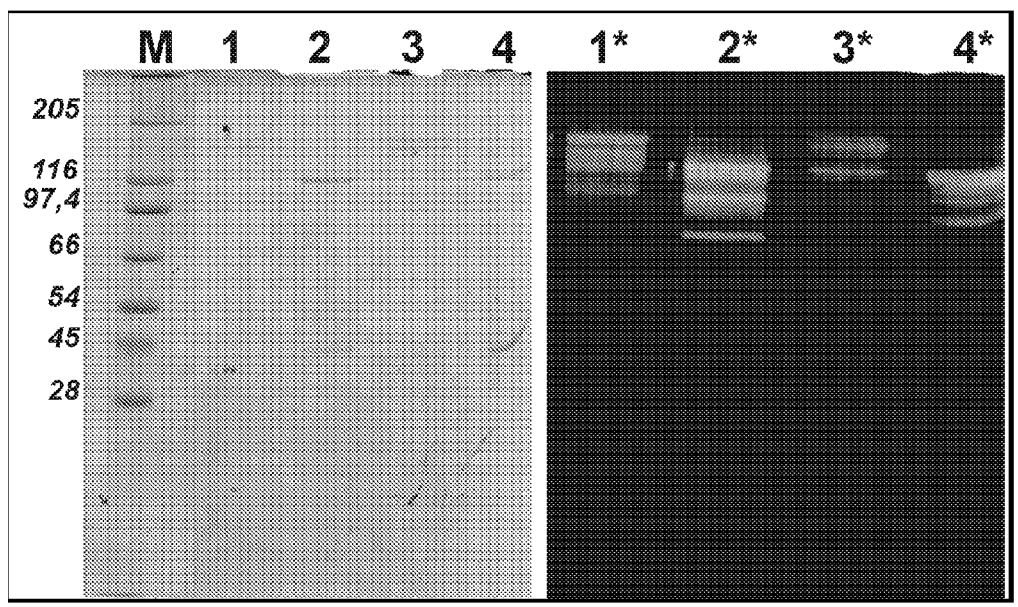

FIG. 5: Analyses using SDS-PAGE 7.5% and zymography of pMAL-colG and pMAL-colH, i.e. the proteins formed in the pMAL vector which then create the MPB-ColH or MBP-ColG fusion proteins and colG and Col H from which the 'maltose binding protein (MBP)' has been removed enzymatically. In lines 1 and 3 pMAL-col G and pMAL-col H have been loaded respectively after amylose column purification; the corresponding gelatine zymography can be seen in 1* and 3*. In lines 2 and 4 col G and col H obtained by digestion with Factor Xa have been loaded respectively; the corresponding gelatine zymography of each sample can be seen in 2* and 4*.

The molecular weights of markers (M), expressed in kDa, are shown to the left thereof.

Figure 6:
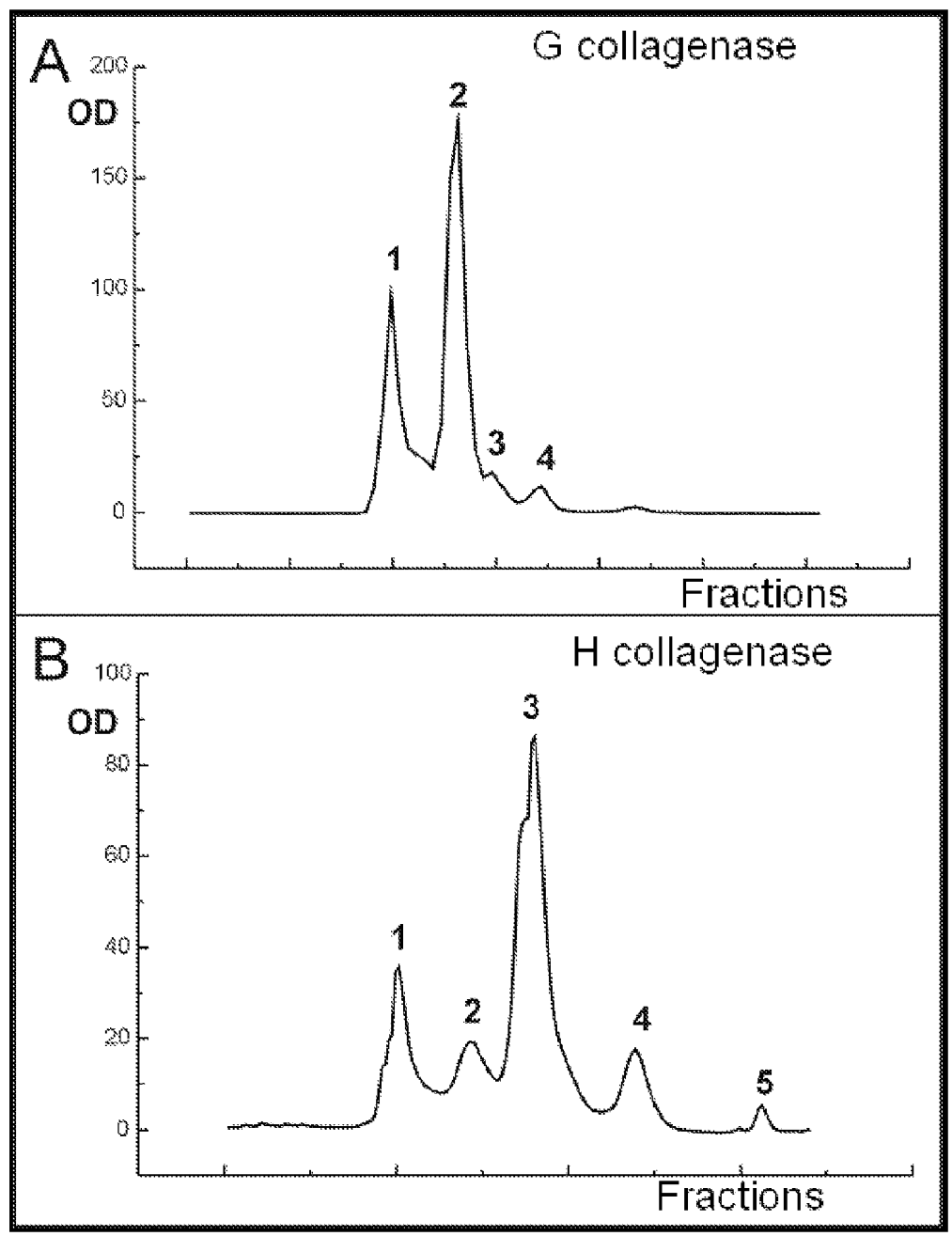

FIG. 6: Elution profiles of pMAL-colG and pMAL-colH, i.e. the proteins formed in the pMAL vector which then create the MPB-ColH or MBP-ColG fusion proteins, by size exclusion chromatography with Superdex 200 FPLC.

In A—elution profile of pMAL-col G. Peak 1 corresponds to the aggregation of various pMAL-colG molecules as a result of weak aspecific interactions caused by the high concentration of the sample. In fact, this band is not present when the sample is loaded on electrophoretic gel after having been boiled. Peak 2 corresponds to monomeric pMAL-colG; whereas peaks 3 and 4 are two truncated shapes as a result of premature termination of the synthesis process, or else have shapes indicating a lack of part of the terminal COOH sequence I.

In B—elution profile of pMAL-colH. In this case also peaks 1 and 2 correspond to the aggregation of various pMAL-colH molecules as a result of weak aspecific interactions caused by the high concentration of the sample, whereas peak 3 corresponds to pMAL-col H. It is presumed that peaks 4 and 5 are products of premature termination of the synthesis, or else have shapes indicative of col H lacking the terminal COOH; as also appears to occur physiologically in vivo.

Figure 7:
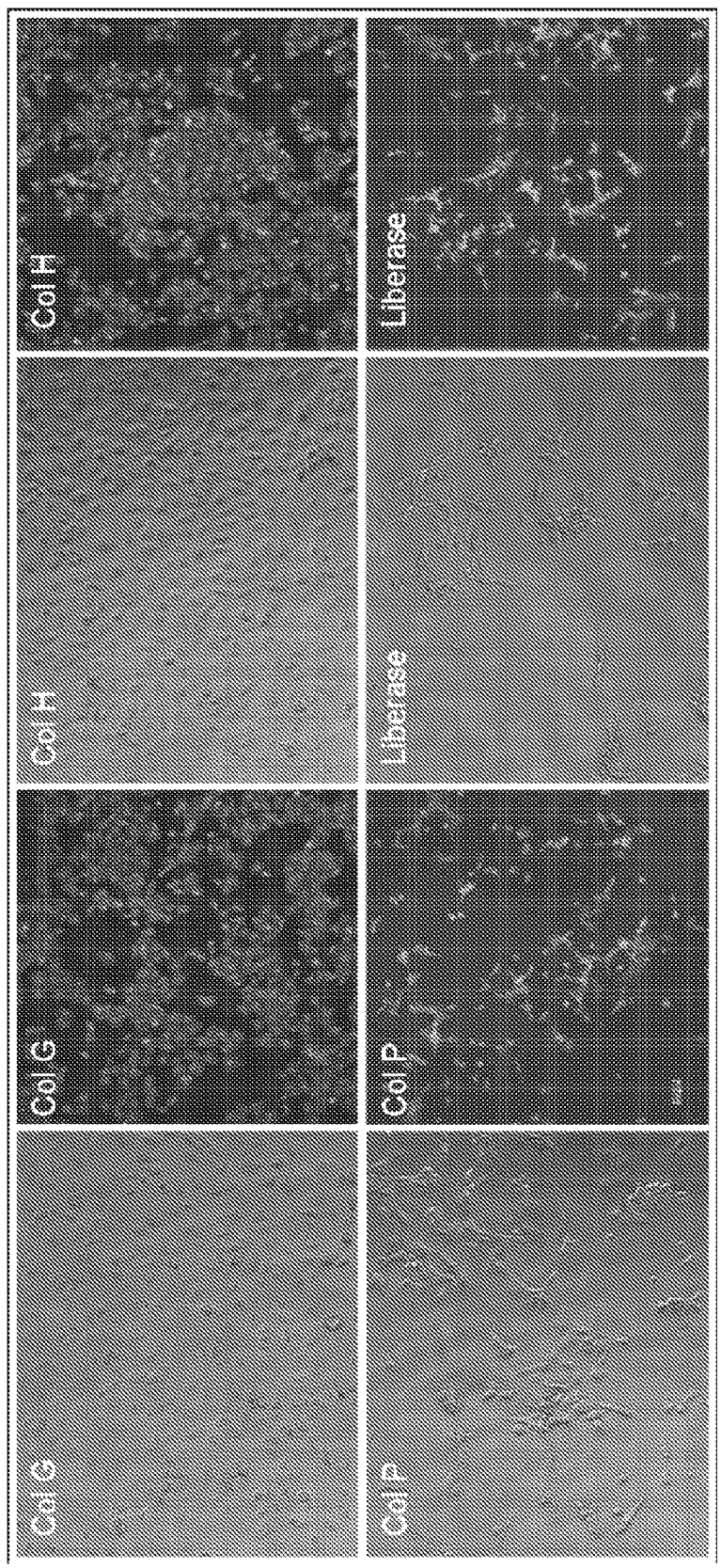

FIG. 7: Extraction of $ECV_{304}$ cells from a three-dimensional type-I collagen matrix.

$ECV_{304}$ cells cultivated within a three-dimensional type-I collagen gel were treated with 0.5 mg/ml of the enzymes produced as disclosed in the present description (pMAL-col G and pMAL-col H, i.e. the proteins produced in the pMAL vector which then create the MPB-colH or MPB-colG fusion proteins) or the commercial collagenases Col P and Liberase (Roche) for two hours at 37° C. in 5% $CO_2$. After this treatment, the gels were digested completely and the cells were scattered over the bottom of the wells, the enzymes were removed and after 14 hours the cells were fixed and observed under a microscope or phase contrasted or stained with phalloidin conjugated with fluorescein (phalloidin$^{-FITC}$) and observed by epifluorescence microscopy.

As can be seen in the figure, once released from the gel the cells treated with pMAL-col G and p-MAL-col H exhibit a differentiated epithelioid phenotype with clear cell-cell contacts; whereas treatment with ColP and Liberase led to the release of cells with a more mesenchymal phenotype without clear cell-cell contacts; it is as if the cells released from treatment with these enzymes are incapable of differentiation.

Figure 8:
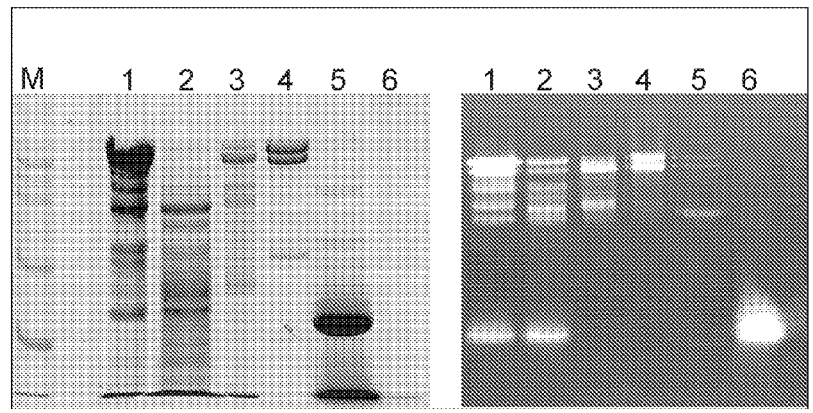

FIG. 8: Protein profile using SDS-PAGE 7.5% and proteolytic profiles using gelatine zymography of commercial proteolytic enzymes used for the extraction of islets of Langerhans.

The left-hand side of the figure shows electrophoretic analysis of the protein components present in the commercial lyophilized forms of the following lytic enzymes used for the extraction of cells from various tissues/organs; whereas the right-hand side shows gelatine zymography thereof. The various samples have been loaded as follows: line 1—Liberase (Roche); 2—New Liberase (Roche); 3—collagenase P (Roche); 4—collagenase NB1 (Serva); 5—neutral protease (Serva); 6—thermolysin (Roche).

Markers of known molecular weight are present in line M (from top to bottom; 205-116-97.4-66-54-45 kDa respectively).

Figure 9:
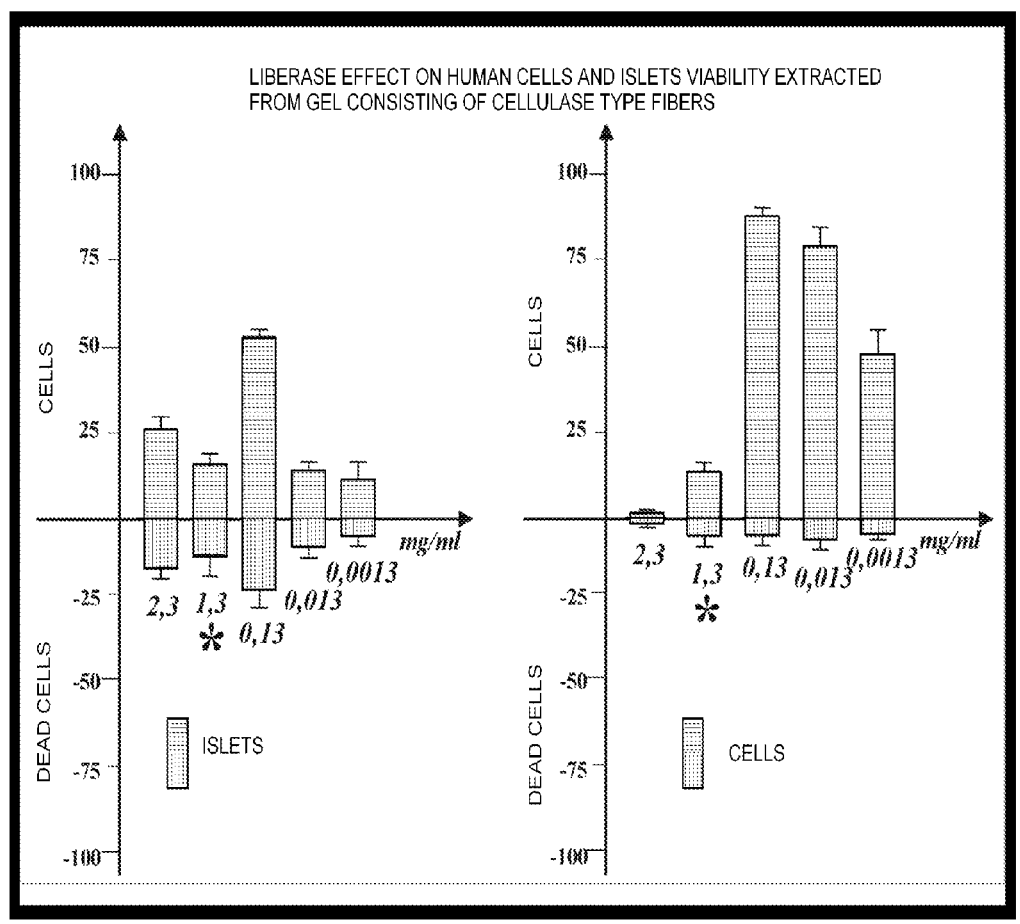

FIG. 9: Extraction activity of Liberase (Roche) on islets of Langerhans and $ECV_{304}$ cells contained in type-I collagen gel.

Liberase (Roche) was used at the concentration normally used to purify islets of Langerhans from the pancreas of donors (*) at double concentration and at concentrations of $1/10$-$1/100$ and $1/1000$ of that normally used. Specific dyes were used to quantify the living and dead cells obtained after extraction both of islets of Langerhans and of $ECV_{304}$ cells.

Figure 10:
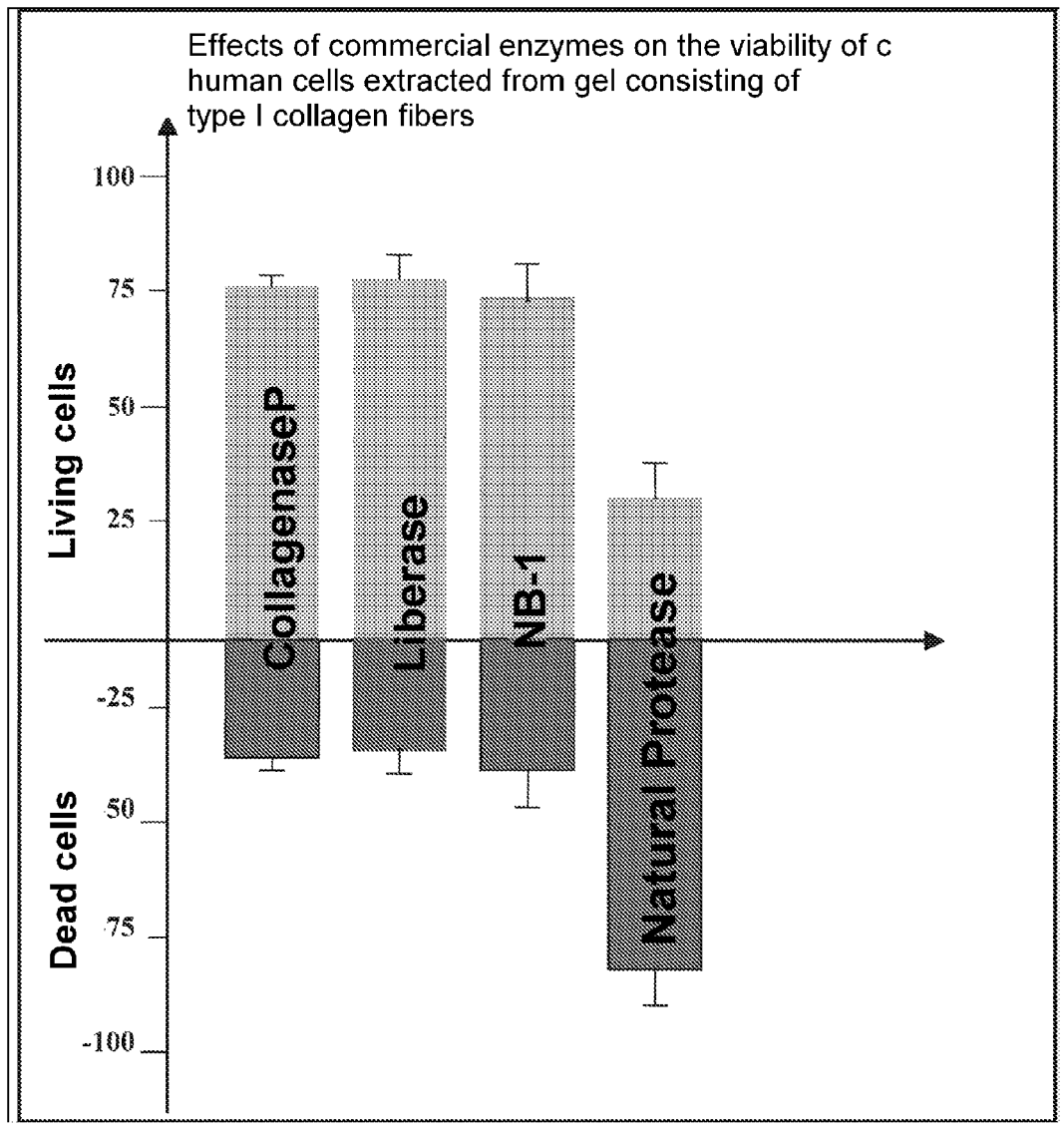

FIG. 10: Effect of commercial enzymes on the extraction of $ECV_{304}$ cells from type-I collagen gel and on cell vitality.

$ECV_{304}$ cells were treated with the concentrations normally used to extract islets of Langerhans to be transplanted in patients suffering from type 1 diabetes and the number of living and dead cells was assessed after two hours of treatment. The assayed enzymes were collagenase P and Liberase from Roche and NB-1 and neutral protease from Serva.

Figure 11:
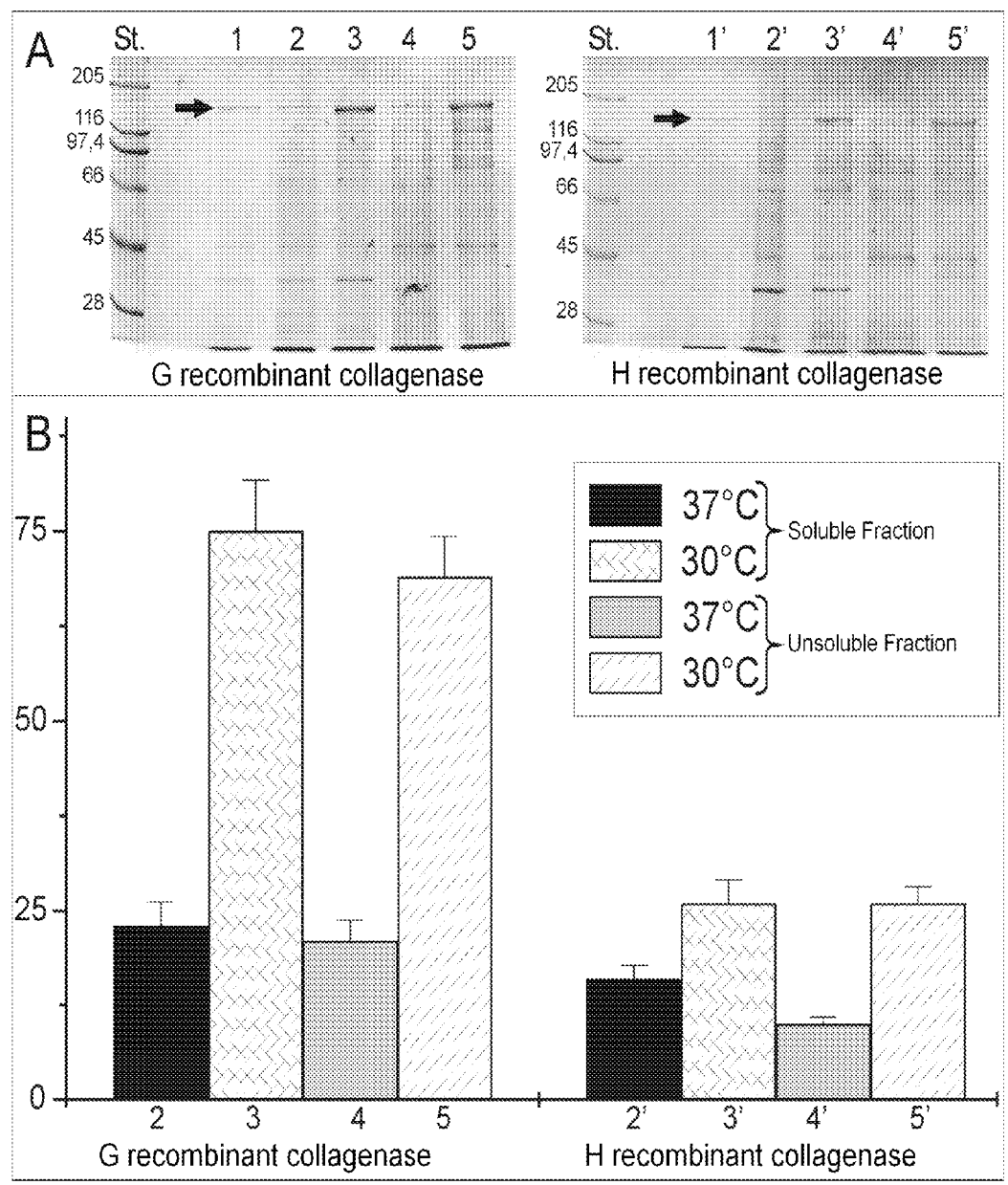

FIG. 11: Evaluation of the effect of growth and induction temperature in the synthesis of recombinant ColG and ColH.

The images in (A) show electrophoresis (SDS-PAGE) of the protein extract obtained from bacteria containing pMAL-colG and pMAL-colH plasmids. Lines 1 and 1' show a total extract of growth bacteria at 30° C.; lines 2 and 2' show the insoluble fractions obtained from growth cultures at 37° C.; lines 3 and 3' show the insoluble fractions obtained at 30° C.; lastly, lines 4 and 4' and 5 and 5' respectively show the insoluble fractions derived from bacterial growth cultures at 37 and 30 degrees respectively. St. indicates the standard of known molecular weight expressed in kDa. The arrows indicate the ColG and H proteins induced respectively to the left and right in (A).

(B) shows the densitometric analyses of the insoluble and soluble fractions of the components induced respectively at 37° C. and 30° C.

It can be seen from the densitometric analyses that there is an increase of approximately 3/3.2 times in the expression of pMAL-col G at 30° C. compared to 37° C.; and of approximately 1.65/2.6 times in pMAL-colH at 30° C. compared to 37° C. The numbers along the x-axis refer to corresponding gel samples in (A).

Figure 12:
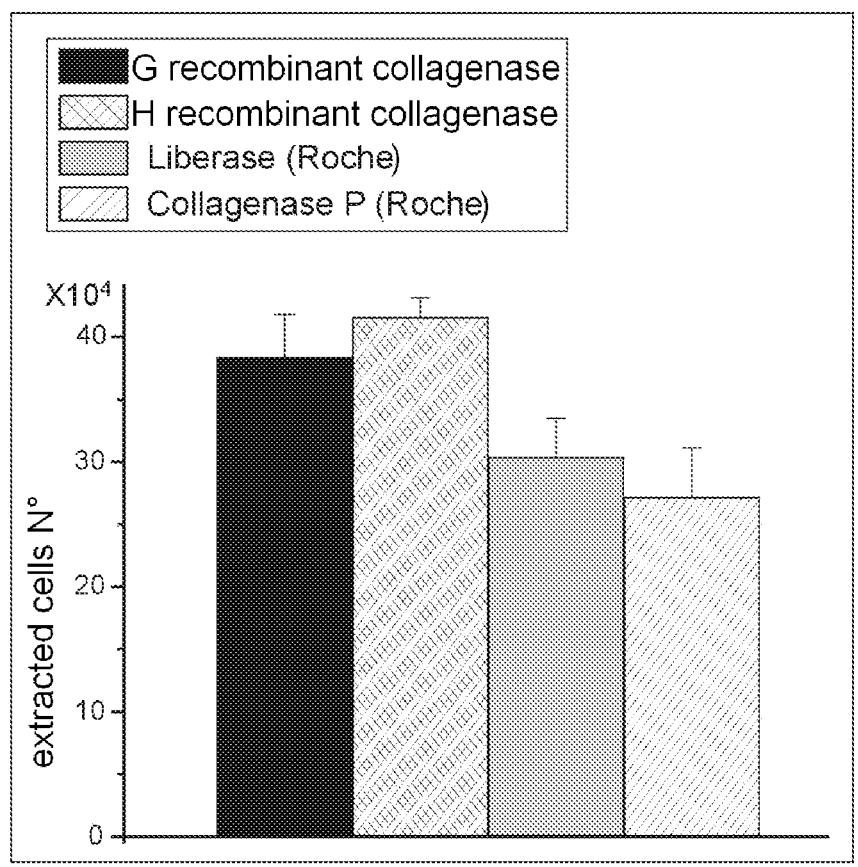

FIG. 12: Extraction capacity of pMAL-col G and pMAL-col H, i.e. of the proteins produced in the pMAL vector which then create the MPB-col H or MBP-col G fusion proteins.

The figure shows the mean values of the number of cells extracted with the various collagenases indicated in the key and obtained from the count of 20 different photographic areas, generated at random. For the collagenases obtained by us using recombinant technology the figure shows an extraction capacity, caused by greater cell vitality, which is higher by approximately 28/36% than the two commercial enzymes shown, when used at the same protein concentration.

Figure 13:
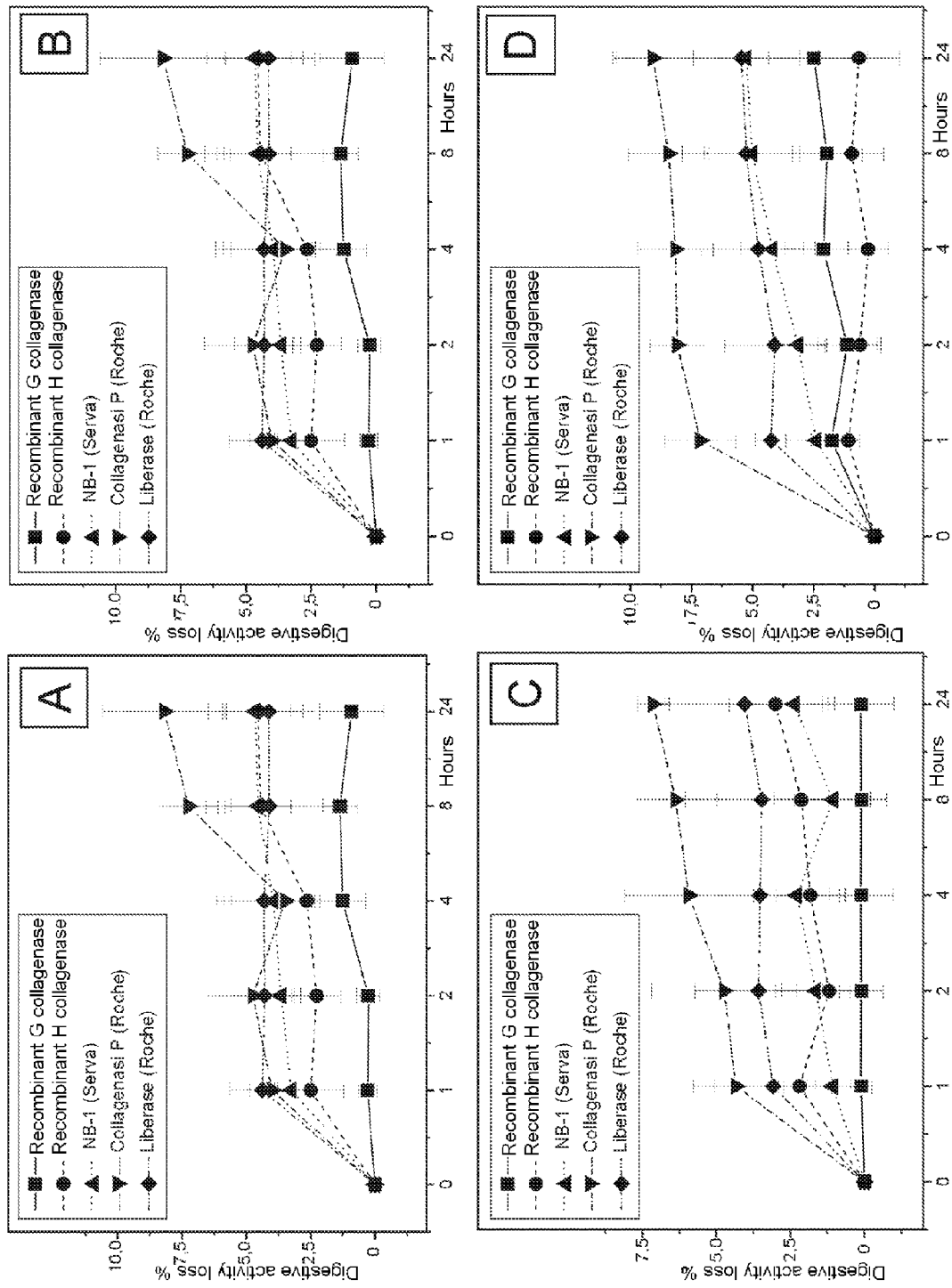

FIG. 13: Variation in lytic activity when the enzymes are used at different temperatures.

The figure shows representations of the profiles for loss of digestive activity on the part of the enzymes of the invention (recombinant collagenase G and recombinant collagenase H) compared to commercial enzymes (NB-1 from Serva, Liberase and collagenase P from Roche). The digestions were carried out for various duration, as indicated along the x-axis and at different temperatures A-25° C., B-30° C., C-37° C. and D-42° C. It can be seen from the values obtained that greater stability of the molecules is obtained by recombinant technology compared to commercial molecules obtained by extractive technology. In any case there is no considerable variation in function of the various molecules analyzed during the 24 hours of use.

Figure 14:
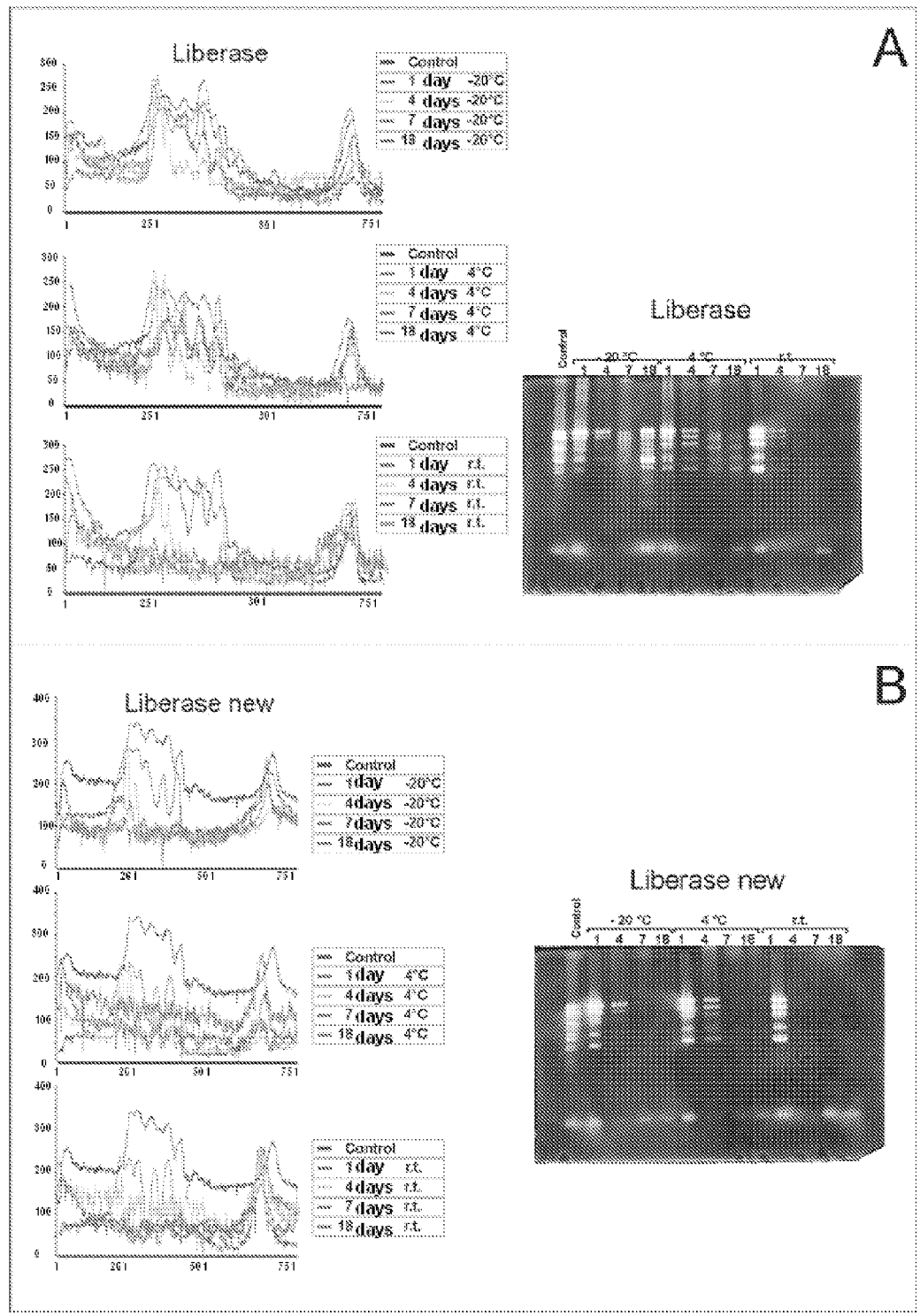
Figure 14:
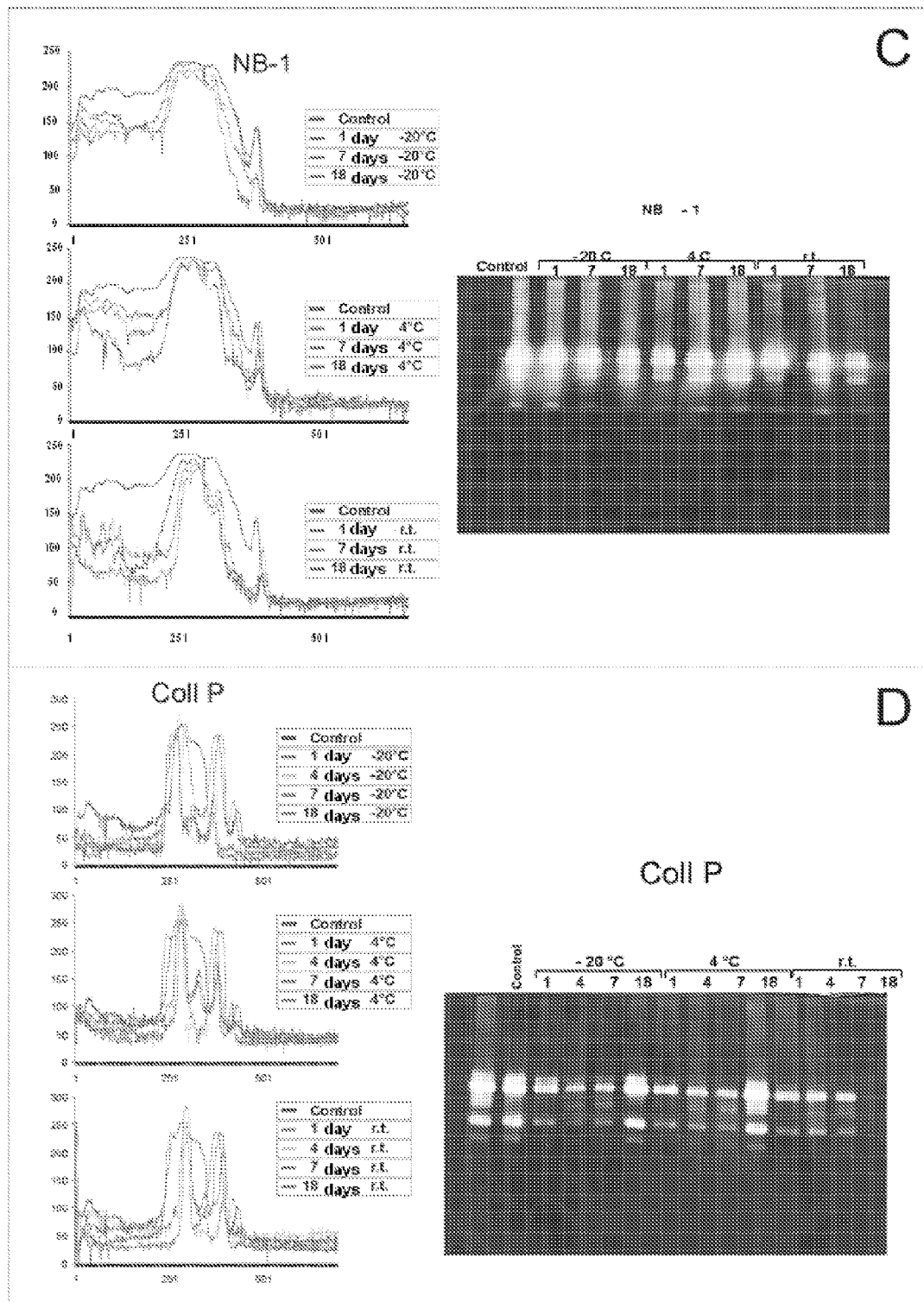
Figure 14:
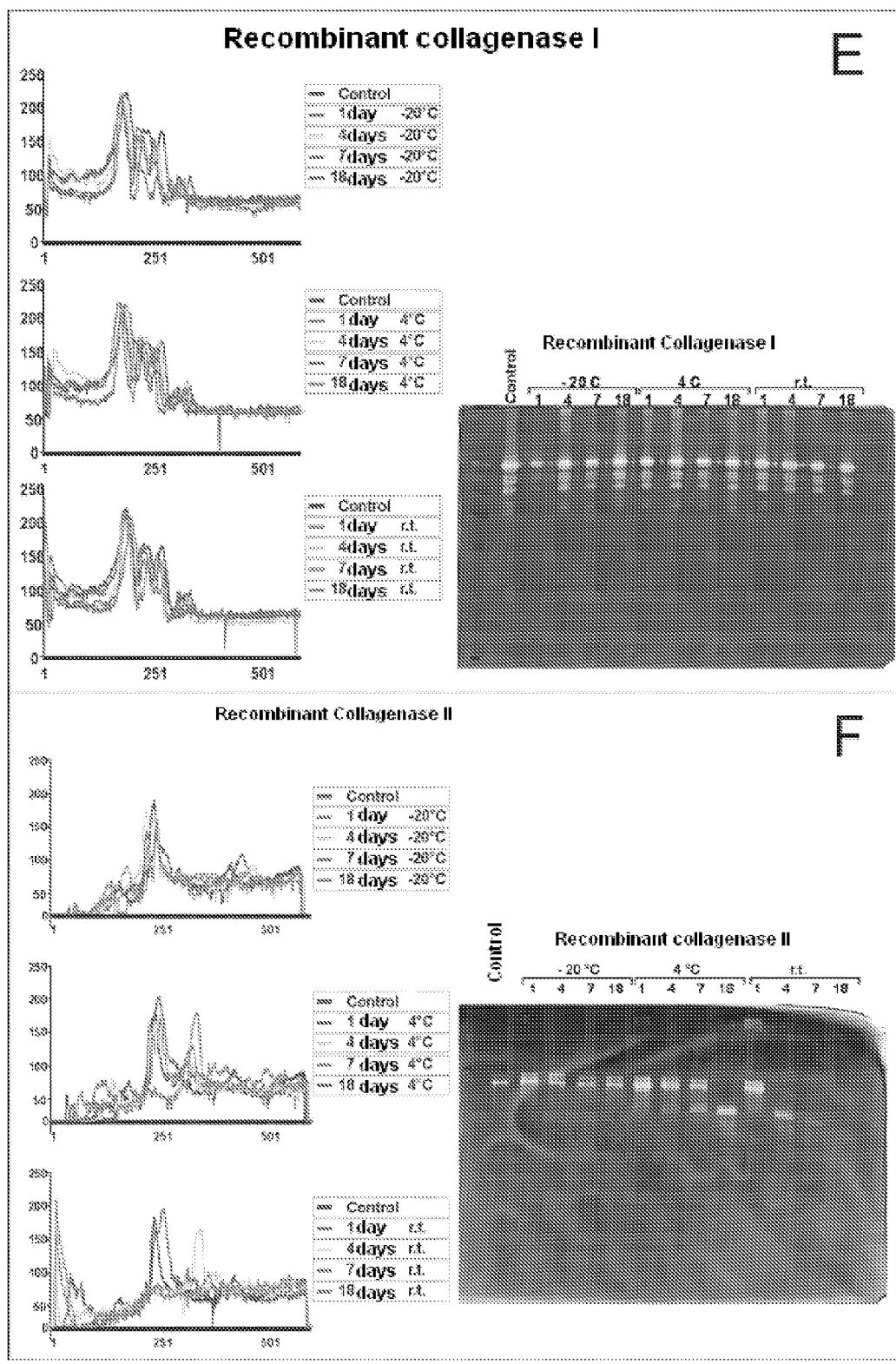

FIG. 14: Densitometric profiles of the gelatinolytic activity identified using zymography of *clostridium histolyticum* collagenases G and H obtained by extractive processes (Roche and Serva) and of the collagenases obtained by the method described herein.

FIGS. 14 A and B show the zymographs and densitometric profiles of two different Liberase batches (Roche): in FIG. 14 a batch of liberase obtained from cultures of *Clostridium histolyticum* was used in which the bacteria were grown in a medium containing pig brain homogenates; FIG. 14 B shows the new preparation of liberase produced by Roche. In FIG. 14 C the product from Serva is analyzed. In FIG. 14 D collagenase P (Roche) is tested, obtained by extraction from *Clostridium histolyticum* but less purified. FIGS. 14 E and F respectively show the zymographs and profiles of collagenases G and H produced by the method described herein.

Figure 15:
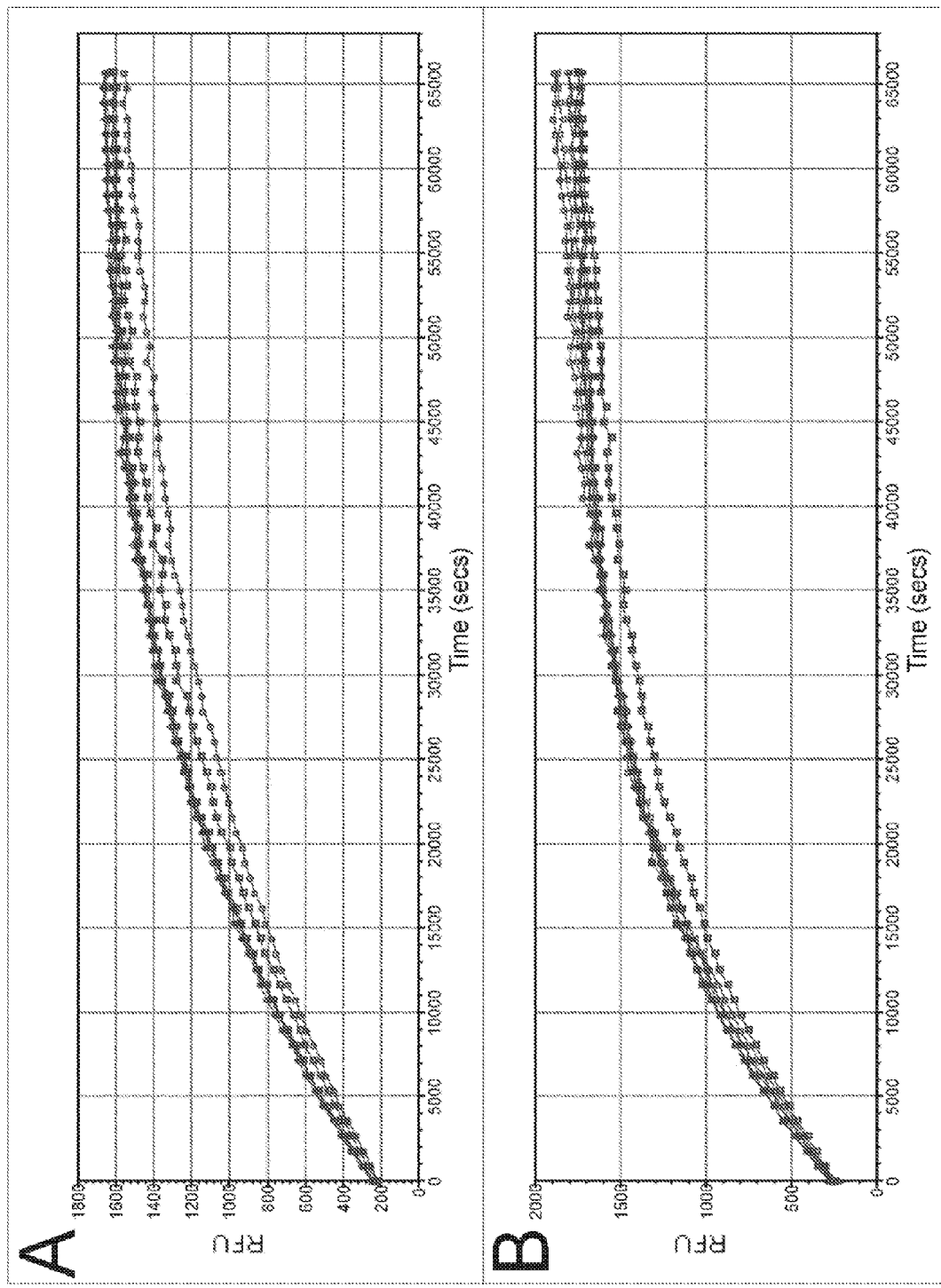

FIG. 15: Kinetics of ColI G and ColI H

FIG. 15 A shows the digestion curves of the synthetic substrate Suc-Gly-Pro-Leu-Gly-Pro-AMC in the presence of the recombinant collagenase G produced by us.

FIG. 15 B shows the digestion curves of the synthetic substrate Suc-Gly-Pro-Leu-Gly-Pro-AMC in the presence of the recombinant collagenase H produced by us.

The analysis was carried out by reading the substrate every 15 minutes for 20 hours, seven (graduated) concentrations of the substrate Suc-Gly-Pro-Leu-Gly-Pro-AMC were used; the following values of maximum velocity in the unit of substrate per second were obtained for ColI G for each concentration 0.056-0.059-0.059-0.065-0.064-0.072-0.068 with a mean Vmax of 0.073-0.068-0.080-0.083-0.078-0.088-0.091 with a mean Vmax of 0.080 units×sec.

DETAILED DESCRIPTION OF THE SEQUENCES

SEQ ID NO 1 nucleotide sequence optimized for expression in *E. coli* coding for *C. histolyticum* Col G SEQ ID NO 2 amino acid sequence coded by SEQ ID NO 1 corresponding to the wild protein sequence of *C. histolyticum* ColG SEQ ID NO 3 nucleotide sequence optimized for expression in *E. coli* coding for *C. histolyticum* Col H SEQ ID NO 4 amino acid sequence coded by SEQ ID NO 3 corresponding to the wild protein sequence of *C. histolyticum* ColH SEQ ID NO 5 cut site for the collagenases Wild nucleotide sequence coding for *C. histolyticum* ColG code Gen Bank D87215.1

Wild nucleotide sequence coding for *C. histolyticum* ColH code GenBank D29981.1

SEQ ID NO 1

```
sequence generated for optimization of the Clostridium histolyticum ColG
gene with the usage codon for genes highly expressive of Escherichia
coli K12
        atg atc gcg aac acc aat agt gag aaa tac gac ttt gaa tac ttg aac ggt ctg agc tac acg gaa ctg act aac ctg atc aaa aac att aag tgg aac cag atc aac ggc ctg ttc aat tat tct act ggc tct cag aaa ttc ttc ggt gac aaa aac cgt gta cag gcg att atc aac gcc ctg cag gaa tct ggc cgc act tat acc gct aac gac atg aaa ggc atc gag acc ttc act gaa gtt ctg cgt gcg ggt ttt tat ctg ggc tac tac aac gac ggt ctg agc tat ctg aac gat cgc aat ttc cag gac aaa tgt atc ccg gcc atg atc gct att cag aaa aac ccg aac ttt aaa ctg ggc act gca gtg cag gac gaa gtt att acc tct ctg ggc aaa ctg atc ggc aac gct tct gcc aac gcc gaa gtt gtg aac aac tgc gtg ccg gtg ctt aag cag ttt cgc gaa aac ctg aac cag tac gcc ccg gat tat gtt aag ggt acc gcc gta aat gaa ctg atc aaa gcc atc gaa ttt gac ttt tct ggt gct gcg tac gaa aag gat gtg aag acc atg ccg tgg tat ggt aaa atc gac ccg ttc atc aac gaa ctg aaa gcc ctg ggc tta tat ggc aac att aca agc gcg acc gaa tgg gcg tca gat gtt ggt atc tat tac ttg
```

-continued agt aaa ttc ggc tta tat tcc acc aac cgt aac gac atc gtt caa agc ctg gag aaa gcg gtt gat atg tac aaa tac ggg aaa atc gca ttt gta gcg atg aac gc att acc tgg gac tac gac ggc atc ggc tca aat ggc aaa aaa gtc gac cac gat aaa ttc ctg gat gac gca gag aaa cac tac ctg cct aaa acc tac acc ttc gac aac ggc aca ttc atc att cgt gct ggc gac aaa gta agc gaa gaa aaa atc aaa aga ctc tac tgg gcg agc cgt gaa gtc aaa agc cag ttt cat cgc gtt gtt ggt aat gac aaa gcg ctg gaa gtt ggt aac gca gat gac gtt tta aca atg aaa atc ttc aat agc ccc gag gag tat aag ttt aac act aac att aac gga gta agc acc gac aac ggt ggt ctg tat atc gaa cct cgc ggc act ttc tat act tat gaa cgc act ccg cag cag tct att ttc tcc ctg gaa gaa ctc ttt cgc cac gaa tat acc cat tat ctg caa gcg cgt tat ctg gtc gat ggc ctg tgg ggc cag ggt cct ttc tat gaa aag aac cgt ctg acc tgg ttc gat gaa ggt acc gca gaa ttc ttc gct ggc agc act cgt acc agc ggt gta ctg ccg cgc aaa agc atc ctg ggc tat ctg gca aaa gac aaa gtg gat cac cgt tac agc ctg aaa aaa acc ctg aat tct gga tac gat gac tcc gat tgg atg ttt tac aac tac ggt ttt gcc gtg gcg cac tac ctg tac gag aaa gat atg cct acg ttc atc aag atg aac aag gcg att ctg aat act gac gtt aaa agc tat gat gag atc att aag aaa ctg tcc gac gac gca aac aaa aac aca gaa tac cag aac cat atc cag gaa tta gca gat aaa tac cag ggt gcg ggt atc ccg ctg gtt tcc gat gac tat ctt aaa gat cac ggt tat aaa aaa gcg tcc gaa gta tac tcc gaa att agc aaa gcg gca tcc ctg acc aac acg tct gtt acc gcc gaa aaa tcc cag tac ttt aac acg ttc acg ctg cgt ggt acc tat acg ggt gaa acg tct aaa ggc gaa ttc aaa gac tgg gat gag atg tcc aag aaa ctg gat ggt act ctg gaa agc ctg gcg aaa aat tct tgg tct ggt tac aag acc ctg acc gct tat ttc acc aac tac cgt gtc acc tcc gac aac aag gta cag tac gac gtt gtc ttc cac ggc gtg ctg acc gat aac gca gac atc tct aac aac aag gcc ccg atc gcg aaa gtt acc ggt ccg tcc acc ggt gct gtt ggt cgt aac atc gaa ttc tcc ggc aaa gac tcc aaa gat gaa gac ggc aaa att gtg tct tat gat tgg gac ttc ggt gac ggt gct acg tcc cgt ggc aaa aac agc gtg cac gca tac aaa aaa gcg ggt acc tac aac gtt aca ttg aaa gtg act gac gat aaa ggc gct acc gcg act gaa tct ttc act atc gaa att aaa aac gaa gac act acc acc ccg att acc aag gaa atg gaa cca aat gac gac atc aaa gaa gct aac ggc ccg atc gtc gaa ggt gtg acc gta aaa ggt gac ctg aat ggt tcg atg ac gca gac acc ttc tac ttc gac gtt aaa gaa gac ggc gac gta acc att gag ctg ccg tac agc ggt tcc tcc aac ttc acc tgg ttg gta tac aaa gaa ggt gac gac cag aac cac att gca tcg ggc att gat aaa aac aac agc aaa gtg ggc acc ttc aaa tcc acc aaa ggt cgc cac tac gtc ttc att tac aaa cat gat tct gcc tcg aac att agc tat tca ctc aac atc aaa ggt ctg ggt aac gaa aag ctg aaa gaa aag gaa aat aac gat tct tcc gat aaa gca acc gtg att ccg aac ttt aac acc act atg cag ggg tcg ctg ctg ggt gac gat tcc cgc gat tat tac tcc ttc gaa gta aaa gaa gag ggc gaa gtg aac atc gaa ctg gat aaa aaa gac gaa ttt ggt gtt acc tgg acg ctg cac ccg gaa tct aac atc aac gac cgt atc acc tat ggc cag gtg gac ggt aac aaa gtt tcc aac aag gtc aaa ctt cgc ccg ggc aaa tat tat ctg ctg gtc tac aag tat tct gga tct ggt aat tac gaa ctg cgt gtt aac aag taa -continued

SEQ ID NO 2 coded amino acid sequence generated for optimization of the *Clostridium histolyticum* ColG gene with the usage codon for genes highly expressive of *Escherichia coli* K12 equal to the wild amino acid sequence Met Ile Ala Asn Thr Asn Ser Glu Lys Tyr Asp Phe Glu Tyr Leu Asn Gly Leu
Ser Tyr Thr Glu Leu Thr Asn Leu Ile Lys Asn Ile Lys Trp Asn Gln Ile Asn Gly Leu
Phe Asn Tyr Ser Thr Gly Ser Gln Lys Phe Phe Gly Asp Lys Asn Arg Val Gln Ala Ile
Ile Asn Ala Leu Gln Glu Ser Gly Arg Thr Tyr Thr Ala Asn Asp Met Lys Gly Ile Glu Thr
Phe Thr Glu Val Leu Arg Ala Gly Phe Tyr Leu Gly Tyr Tyr Asn Asp Gly Leu Ser Tyr
Leu Asn Asp Arg Asn Phe Gln Asp Lys Cys Ile Pro Ala Met Ile Ala Ile Gln Lys Asn
Pro Asn Phe Lys Leu Gly Thr Ala Val Gln Asp Glu Val Ile Thr Ser Leu Gly Lys Leu
Ile Gly Asn Ala Ser Ala Asn Ala Glu Val Val Asn Asn Cys Val Pro Val Leu Lys Gln
Phe Arg Glu Asn Leu Asn Gln Tyr Ala Pro Asp Tyr Val Lys Gly Thr Ala Val Asn Glu
Leu Ile Lys Gly Ile Glu Phe Asp Phe Ser Gly Ala Ala Tyr Glu Lys Asp Val Lys Thr
Met Pro Trp Tyr Gly Lys Ile Asp Pro Phe Ile Asn Glu Leu Lys Ala Leu Gly Leu Tyr
Gly Asn Ile Thr Ser Ala Thr Glu Trp Ala Ser Asp Val Gly Ile Tyr Tyr Leu Ser Lys Phe
Gly Leu Tyr Ser Thr Asn Arg Asn Asp Ile Val Gln Ser Leu Glu Lys Ala Val Asp Met
Tyr Lys Tyr Gly Lys Ile Ala Phe Val Ala Met Glu Arg Ile Thr Trp Asp Tyr Asp Gly Ile
Gly Ser Asn Gly Lys Lys Val Asp His Asp Lys Phe Leu Asp Asp Ala Glu Lys His Tyr
Leu Pro Lys Thr Tyr Thr Phe Asp Asn Gly Thr Phe Ile Ile Arg Ala Gly Asp Lys Val
Ser Glu Glu Lys Ile Lys Arg Leu Tyr Trp Ala Ser Arg Glu Val Lys Ser Gln Phe His
Arg Val Val Gly Asn Asp Lys Ala Leu Glu Val Gly Asn Ala Asp Asp Val Leu Thr Met
Lys Ile Phe Asn Ser Pro Glu Glu Tyr Lys Phe Asn Thr Asn Ile Asn Gly Val Ser Thr
Asp Asn Gly Gly Leu Tyr Ile Glu Pro Arg Gly Thr Phe Tyr Thr Tyr Glu Arg Thr Pro
Gln Gln Ser Ile Phe Ser Leu Glu Glu Leu Phe Arg His Glu Tyr Thr His Tyr Leu Gln
Ala Arg Tyr Leu Val Asp Gly Leu Trp Gly Gln Gly Pro Phe Tyr Glu Lys Asn Arg Leu
Thr Trp Phe Asp Glu Gly Thr Ala Glu Phe Phe Ala Gly Ser Thr Arg Thr Ser Gly Val
Leu Pro Arg Lys Ser Ile Leu Gly Tyr Leu Ala Lys Asp Lys Val Asp His Arg Tyr Ser
Leu Lys Lys Thr Leu Asn Ser Gly Tyr Asp Asp Ser Asp Trp Met Phe Tyr Asn Tyr Gly
Phe Ala Val Ala His Tyr Leu Tyr Glu Lys Asp Met Pro Thr Phe Ile Lys Met Asn Lys
Ala Ile Leu Asn Thr Asp Val Lys Ser Tyr Asp Glu Ile Ile Lys Lys Leu Ser Asp Asp Ala
Asn Lys Asn Thr Glu Tyr Gln Asn His Ile Gln Glu Leu Ala Asp Lys Tyr Gln Gly Ala
Gly Ile Pro Leu Val Ser Asp Asp Tyr Leu Lys Asp His Gly Tyr Lys Lys Ala Ser Glu
Val Tyr Ser Glu Ile Ser Lys Ala Ala Ser Leu Thr Asn Thr Ser Val Thr Ala Glu Lys Ser
Gln Tyr Phe Asn Thr Phe Thr Leu Arg Gly Thr Tyr Thr Gly Glu Thr Ser Lys Gly Glu
Phe Lys Asp Trp Asp Glu Met Ser Lys Lys Leu Asp Gly Thr Leu Glu Ser Leu Ala Lys
Asn Ser Trp Ser Gly Tyr Lys Thr Leu Thr Ala Tyr Phe Thr Asn Tyr Arg Val Thr Ser
Asp Asn Lys Val Gln Tyr Asp Val Val Phe His Gly Val Leu Thr Asp Asn Ala Asp Ile
Ser Asn Asn Lys Ala Pro Ile Ala Lys Val Thr Gly Pro Ser Thr Gly Ala Val Gly Arg
Asn Ile Glu Phe Ser Gly Lys Asp Ser Lys Asp Glu Asp Gly Lys Ile Val Ser Tyr Asp
Trp Asp Phe Gly Asp Gly Ala Thr Ser Arg Gly Lys Asn Ser Val His Ala Tyr Lys Lys
Ala Gly Thr Tyr Asn Val Thr Leu Lys Val Thr Asp Asp Lys Gly Ala Thr Ala Thr Glu
Ser Phe Thr Ile Glu Ile Lys Asn Glu Asp Thr Thr Thr Pro Ile Thr Lys Glu Met Glu Pro -continued

```
Asn Asp Asp Ile Lys Glu Ala Asn Gly Pro Ile Val Glu Gly Val Thr Val Lys Gly Asp
Leu Asn Gly Ser Asp Asp Ala Asp Thr Phe Tyr Phe Asp Val Lys Glu Asp Gly Asp
Val Thr Ile Glu Leu Pro Tyr Ser Gly Ser Ser Asn Phe Thr Trp Leu Val Tyr Lys Glu
Gly Asp Asp Gln Asn His Ile Ala Ser Gly Ile Asp Lys Asn Asn Ser Lys Val Gly Thr
Phe Lys Ser Thr Lys Gly Arg His Tyr Val Phe Ile Tyr Lys His Asp Ser Ala Ser Asn Ile
Ser Tyr Ser Leu Asn Ile Lys Gly Leu Gly Asn Glu Lys Leu Lys Glu Lys Glu Asn Asn
Asp Ser Ser Asp Lys Ala Thr Val Ile Pro Asn Phe Asn Thr Thr Met Gln Gly Ser Leu
Leu Gly Asp Asp Ser Arg Asp Tyr Tyr Ser Phe Glu Val Lys Glu Glu Gly Glu Val Asn
Ile Glu Leu Asp Lys Lys Asp Glu Phe Gly Val Thr Trp Thr Leu His Pro Glu Ser Asn
Ile Asn Asp Arg Ile Thr Tyr Gly Gln Val Asp Gly Asn Lys Val Ser Asn Lys Val Lys
Leu Arg Pro Gly Lys Tyr Tyr Leu Leu Val Tyr Lys Tyr Ser Gly Ser Gly Asn Tyr Glu
Leu Arg Val Asn Lys
```

SEQ ID No 3 sequence generated for optimization of the *Clostridium histolyticum* ColH gene with the usage codon for genes largely expressive of *E. coli* K12

```
       acc atg gtt caa aac gaa agc aaa cgt tac acc gtg agc tat ctg aag acc ctg aat
tac tac gac ctg gta gat ctg ctg gtc aag acg gaa atc gag aac ctg ccg gac ctg ttc cag
tat agt agc gat gcc aaa gag ttt tac ggg aac aaa acg cgc atg tcg ttc att atg gat gaa atc
ggt cgc cgt gcc ccg cag tat acg gaa atc gat cat aaa ggg att cct act ctg gta gaa gtg
gtc cgc gct ggg ttt tat ctg ggg ttt cac aat aaa gaa ctg aat gaa att aac aag cgt agt ttt
aag gag cgc gtg att cca agc atc ctg gca atc cag aag aat ccg aac ttc aag ctg ggg acc
gag gtg caa gat aaa atc gtc agt gcc act ggc ctg ctg gct ggc aat gag act gcc cca ccg
gaa gtg gtc aat aac ttt acc ccg atc ctg caa gac tgc att aaa aat att gat cgt tac gca ctg
gat gat ctg aaa agc aaa gca ctg ttc aac gta ctg gct gca cct act tac gac att act gaa tat
ctg cgc gct act aaa gaa aaa cca gaa aac acg cct tgg tat ggt aaa att gac ggt ttc att aat
gaa ctg aag aag ctg gcc ctg tat ggg aaa atc aat gac aat aat agc tgg att atc gac aat
ggg att tat cat atc gcg cct ctg ggg aaa ctg cat agc aac aat aag atc ggc att gag acc
ctg act gag gta atg aaa gta tac cca tat ctg tcg atg cag cat ctg caa agc gca gat caa att
aag cgc cat tat gac tcg aaa gat gct gaa ggt aat aag att ccg ctg gac aag ttc aaa aaa
gag ggc aaa gaa aaa tat tgt ccg aag acc tat acg ttt gac gat ggt aaa gtg att att aaa gct
ggt gct cgc gtt gaa gaa gaa aaa gtc aaa cgt ctg tat tgg gct agc aaa gaa gtg aat agc
caa ttt ttt cgc gtc tat ggc att gat aaa cca ctg gag gag ggt aat cca gat gat atc ctg acg
atg gtc atc tat aat agc ccg gaa gaa tat aaa ctg aac tcg gtc ctg tat ggt tac gac acg aac
aac ggt ggc atg tat att gaa ccg gag ggc acg ttc ttt acg tac gag cgt gaa gcc caa gag
agc acg tat act ctg gaa gaa ctg ttc cgt cat gaa tat acg cac tac ctg caa ggg cgc tac
gcg gtt cca ggt cag tgg ggc cgt acg aag ctg tac gat aac gac cgt ctg acc tgg tac gag
gaa ggg ggc gct gaa ctg ttt gct ggt tcg acc cgt act agc ggt att ctg ccg cgc aaa agc att
gta agc aac atc cac aac act acg cgc aac aac cgt tat aaa ctg agc gat acc gtg cat agc
aag tat ggc gcg tcg ttt gag ttt tat aat tac gcg tgc atg ttc atg gac tat atg tac aac aaa
gac atg ggc att ctg aat aaa ctg aat gac ctg gcg aaa aat aac gat gtt gac ggc tat gac
aat tac atc cgc gat ctg agc agc aac tat gca ctg aac gac aag tat cag gat cac atg caa
```

```
gag cgc att gac aac tac gag aat ctg acg gtt ccg ttt gtt gcg gat gac tat ctg gtc cgc cac gcg tat aaa aac cct aat gaa att tat agc gag att agc gag gtt gcg aag ctg aaa gat gct aaa agc gaa gtc aag aaa agc cag tac ttc agt acg ttc act ctg cgt ggt agc tac acg ggc ggc gcg agc aaa ggc aaa ctg gag gac cag aaa gcc atg aat aaa ttt att gat gac agc ctg aag aag ctg gac acg tac agt tgg agc ggg tat aaa acg ctg act gct tat ttt acc aac tac aaa gta gat agc agc aac cgt gtt acc tat gat gtt gtg ttc cac ggt tac ctg ccg aac gag ggt gat tcg aaa aat tcg ctg cct tat ggc aaa att aac ggt acc tac aag ggc acg gag aaa gaa aag atc aaa ttt agc agc gaa ggc agc ttt gac ccg gat ggt aag att gtc agc tac gaa tgg gat ttt ggc gac ggt aac aaa agc aac gaa gaa aac cca gaa cat agc tac gac aaa gtt ggc acc tat acc gtt aag ctg aaa gtg acc gat gac aag ggc gaa agc agt gtt agt acc acc acg gcg gag atc aag gat ctg agc gaa aac aaa ctg ccg gtg atc tat atg cac gta ccg aaa tcg ggt gcg ctg aac cag aaa gtg gtg ttt tac ggc aag ggc act tac gat ccg gat ggt tcg att gca ggc tat cag tgg gat ttt ggc gat ggc agc gat ttc agt agc gag cag aat ccg tcg cac gtc tat acc aaa aaa ggc gaa tat acc gtt acc ctg cgc gtg atg gac tcg tcg ggc cag atg agt gag aaa act atg aag att aaa atc acc gac ccg gtt tac ccg att ggc acc gaa aaa gaa ccg aac aac agc aag gag acg gct agc ggt ccg atc gtt ccg ggc atc ccg gtt agt ggc acc att gaa aat acc agc gac cag gac tat ttt tat ttt gat gtt att acc cca ggt gag gtt aaa att gac att aac aaa ctg ggc tac ggc ggc gcc acc tgg gtc gtg tat gat gaa aat aat aac gcg gtg agc tac gcg acc gat gac ggg cag aac ctg agc ggc aaa ttc aag gcc gat aaa ccg ggc cgc tac tat att cat ctg tat atg ttt aac ggc agc tat atg ccg tat cgc atc aat atc gaa ggc agc gtg ggc cgc taa                                                                    SEQ ID No 4
``` coded amino acid sequence generated for optimization of the *Clostridium histolyticum* ColH gene with the usage codon for genes highly expressive of *Escherichia coli* K12 equal to the wild amino acid sequence

```
    Thr Met Val Gln Asn Glu Ser Lys Arg Tyr Thr Val Ser Tyr Leu Lys Thr Leu

Asn Tyr Tyr Asp Leu Val Asp Leu Leu Val Lys Thr Glu Ile Glu Asn Leu Pro Asp Leu

Phe Gln Tyr Ser Ser Asp Ala Lys Glu Phe Tyr Gly Asn Lys Thr Arg Met Ser Phe Ile

Met Asp Glu Ile Gly Arg Arg Ala Pro Gln Tyr Thr Glu Ile Asp His Lys Gly Ile Pro Thr

Leu Val Glu Val Val Arg Ala Gly Phe Tyr Leu Gly Phe His Asn Lys Glu Leu Asn Glu

Ile Asn Lys Arg Ser Phe Lys Glu Arg Val Ile Pro Ser Ile Leu Ala Ile Gln Lys Asn Pro

Asn Phe Lys Leu Gly Thr Glu Val Gln Asp Lys Ile Val Ser Ala Thr Gly Leu Leu Ala

Gly Asn Glu Thr Ala Pro Pro Glu Val Val Asn Asn Phe Thr Pro Ile Leu Gln Asp Cys

Ile Lys Asn Ile Asp Arg Tyr Ala Leu Asp Asp Leu Lys Ser Lys Ala Leu Phe Asn Val

Leu Ala Ala Pro Thr Tyr Asp Ile Thr Glu Tyr Leu Arg Ala Thr Lys Glu Lys Pro Glu

Asn Thr Pro Trp Tyr Gly Lys Ile Asp Gly Phe Ile Asn Glu Leu Lys Lys Leu Ala Leu

Tyr Gly Lys Ile Asn Asp Asn Asn Ser Trp Ile Ile Asp Asn Gly Ile Tyr His Ile Ala Pro

Leu Gly Lys Leu His Ser Asn Asn Lys Ile Gly Ile Glu Thr Leu Thr Glu Val Met Lys

Val Tyr Pro Tyr Leu Ser Met Gln His Leu Gln Ser Ala Asp Gln Ile Lys Arg His Tyr

Asp Ser Lys Asp Ala Glu Gly Asn Lys Ile Pro Leu Asp Lys Phe Lys Lys Glu Gly Lys

Glu Lys Tyr Cys Pro Lys Thr Tyr Thr Phe Asp Asp Gly Lys Val Ile Ile Lys Ala Gly Ala

Arg Val Glu Glu Glu Lys Val Lys Arg Leu Tyr Trp Ala Ser Lys Glu Val Asn Ser Gln

Phe Phe Arg Val Tyr Gly Ile Asp Lys Pro Leu Glu Glu Gly Asn Pro Asp Asp Ile Leu
```

-continued

Thr Met Val Ile Tyr Asn Ser Pro Glu Glu Tyr Lys Leu Asn Ser Val Leu Tyr Gly Tyr

Asp Thr Asn Asn Gly Gly Met Tyr Ile Glu Pro Glu Gly Thr Phe Phe Thr Tyr Glu Arg

Glu Ala Gln Glu Ser Thr Tyr Thr Leu Glu Glu Leu Phe Arg His Glu Tyr Thr His Tyr

Leu Gln Gly Arg Tyr Ala Val Pro Gly Gln Trp Gly Arg Thr Lys Leu Tyr Asp Asn Asp

Arg Leu Thr Trp Tyr Glu Glu Gly Gly Ala Glu Leu Phe Ala Gly Ser Thr Arg Thr Ser

Gly Ile Leu Pro Arg Lys Ser Ile Val Ser Asn Ile His Asn Thr Thr Arg Asn Asn Arg Tyr

Lys Leu Ser Asp Thr Val His Ser Lys Tyr Gly Ala Ser Phe Glu Phe Tyr Asn Tyr Ala

Cys Met Phe Met Asp Tyr Met Tyr Asn Lys Asp Met Gly Ile Leu Asn Lys Leu Asn

Asp Leu Ala Lys Asn Asn Asp Val Asp Gly Tyr Asp Asn Tyr Ile Arg Asp Leu Ser Ser

Asn Tyr Ala Leu Asn Asp Lys Tyr Gln Asp His Met Gln Glu Arg Ile Asp Asn Tyr Glu

Asn Leu Thr Val Pro Phe Val Ala Asp Asp Tyr Leu Val Arg His Ala Tyr Lys Asn Pro

Asn Glu Ile Tyr Ser Glu Ile Ser Glu Val Ala Lys Leu Lys Asp Ala Lys Ser Glu Val Lys

Lys Ser Gln Tyr Phe Ser Thr Phe Thr Leu Arg Gly Ser Tyr Thr Gly Gly Ala Ser Lys

Gly Lys Leu Glu Asp Gln Lys Ala Met Asn Lys Phe Ile Asp Asp Ser Leu Lys Lys Leu

Asp Thr Tyr Ser Trp Ser Gly Tyr Lys Thr Leu Thr Ala Tyr Phe Thr Asn Tyr Lys Val

Asp Ser Ser Asn Arg Val Thr Tyr Asp Val Val Phe His Gly Tyr Leu Pro Asn Glu Gly

Asp Ser Lys Asn Ser Leu Pro Tyr Gly Lys Ile Asn Gly Thr Tyr Lys Gly Thr Glu Lys

Glu Lys Ile Lys Phe Ser Ser Glu Gly Ser Phe Asp Pro Asp Gly Lys Ile Val Ser Tyr

Glu Trp Asp Phe Gly Asp Gly Asn Lys Ser Asn Glu Glu Asn Pro Glu His Ser Tyr Asp

Lys Val Gly Thr Tyr Thr Val Lys Leu Lys Val Thr Asp Asp Lys Gly Glu Ser Ser Val

Ser Thr Thr Thr Ala Glu Ile Lys Asp Leu Ser Glu Asn Lys Leu Pro Val Ile Tyr Met His

Val Pro Lys Ser Gly Ala Leu Asn Gln Lys Val Val Phe Tyr Gly Lys Gly Thr Tyr Asp

Pro Asp Gly Ser Ile Ala Gly Tyr Gln Trp Asp Phe Gly Asp Gly Ser Asp Phe Ser Ser

Glu Gln Asn Pro Ser His Val Tyr Thr Lys Lys Gly Glu Tyr Thr Val Thr Leu Arg Val

Met Asp Ser Ser Gly Gln Met Ser Glu Lys Thr Met Lys Ile Lys Ile Thr Asp Pro Val

Tyr Pro Ile Gly Thr Glu Lys Glu Pro Asn Asn Ser Lys Glu Thr Ala Ser Gly Pro Ile Val

Pro Gly Ile Pro Val Ser Gly Thr Ile Glu Asn Thr Ser Asp Gln Asp Tyr Phe Tyr Phe

Asp Val Ile Thr Pro Gly Glu Val Lys Ile Asp Ile Asn Lys Leu Gly Tyr Gly Gly Ala Thr

Trp Val Val Tyr Asp Glu Asn Asn Asn Ala Val Ser Tyr Ala Thr Asp Asp Gly Gln Asn

Leu Ser Gly Lys Phe Lys Ala Asp Lys Pro Gly Arg Tyr Tyr Ile His Leu Tyr Met Phe

Asn Gly Ser Tyr Met Pro Tyr Arg Ile Asn Ile Glu Gly Ser Val Gly Arg

SEQ ID 5 collagenase cut site between Xaa and Gly

Xaa can be any natural amino acid

Xaa Pro Xaa Gly Pro Xaa

DETAILED DESCRIPTION OF THE INVENTION

The present description provides, for the first time, a method for the production of *C. histolyticum* recombinant collagenase (Col) in biologically active form, with a yield higher than approximately 140 mg/l of culture of said collagenases in soluble, biologically active form.

The method described herein makes it possible, using recombinant DNA methods, to produce elevated amounts of *C. histolyticum* recombinant collagenase with preservation of its biological activity. In particular, experimental conditions are described which ensure, on the one hand, high levels of heterologous expression of said collagenases in prokaryotes and, on the other, the accumulation thereof in the soluble cellular fraction, thus avoiding retention in the enclosed core. However, said method does not contain any laborious steps necessary for solubilisation of said collagenases which, furthermore, could lead to a reduction in or loss of enzyme activity of the recombinant proteins produced. Consequently, the method disclosed herein makes it possible to obtain recombinant collagenases in soluble and enzymatically active form with a yield higher than 140 mg/l of culture, and therefore with yields that are significantly higher than the methods presented in the known prior art, which is particularly useful in the medical field.

The present invention therefore provides a method for the production of *C. histolyticum* recombinant collagenase in soluble and enzymatically active form, comprising the steps of:

a) designing a nucleotide sequence optimized for the expression of said collagenase of *C. histolyticum*;

b) introducing, in an inducible expression vector, an oligonucleotide sequence coding for a fusion protein, wherein said oligonucleotide sequence consists in said optimized sequence fused to a nucleotide sequence coding for a soluble polypeptide and wherein said oligonucleotide sequence is operatively linked to an inducible promoter sequence, a transcription start sequence and a termination sequence;

c) transforming a bacterial strain defective in the expression of endogenous proteases with said expression vector;

d) culturing said transformed bacterial strain at a temperature comprised in a range of 28-32° C., extremes included;

e) inducing the expression of said fusion protein by adding a suitable inducer in said bacterial strain;

f) extracting the fusion protein obtained at point e), and g) purifying said fusion protein;

wherein said method provides a yield higher than 140 mg/l of culture of said collagenase in soluble and enzymatically active form.

The purpose of the design of a nucleotide sequence optimized for the expression of a protein from its wild nucleotide sequence is to improve the efficiency of heterologous expression of proteins in host bacterial strains since it is based on the selection of codons which are recognized more quickly and efficiently by the expression system of the relevant host cell. In one embodiment of the invention the optimization process consists in the substitution of one or more nucleotide triplets (codons) coding for specific amino acids, present in the wild nucleotide sequence coding for one of the *C. histolyticum* collagenases, with the nucleotide codon coding for the same amino acid used more frequently by the organism in which it is intended to express the collagenase of interest.

Such optimization can be achieved by any method known from the prior art, for example, in accordance with one embodiment, an algorithm can be used to achieve the optimized design of point a) by analyzing any sequence coding for said *C. histolyticum* collagenase.

Given the simplicity of the method, it is clear that any wild or mutant nucleotide sequence coding for *C. histolyticum* collagenase can be optimized for the purposes of the present description. The person skilled in the art therefore can start from the nucleotide sequence coding for the desired collagenase and optimize it as a function of the host organism in which it is intended to express said sequence.

In one embodiment it may be desired to produce a wild collagenase known in the literature from any one of the wild sequences reported in GenBank (code D87215.1 for wild ColG or class I collagenase or code D29981.1 for wild ColH or class II collagenase). The program selected by the person skilled in the art from those known in the prior art will indicate the alternative codons taking, as reference, the codons more frequently found in the highly expressed genes (HEG) of the desired host organism. Obviously, it will be possible to achieve optimization both starting from the amino acid sequences and starting from the nucleotide sequences as is obvious, given that in this instance the knowledge of the amino acid sequence is, per se, sufficient to obtain optimization and the nucleotide sequence indicates, without a doubt, the corresponding amino acid sequence.

The process of optimization therefore generates a new nucleotide sequence from the wild nucleotide sequence coding for one of the *C. histolyticum* collagenases, these sequences both coding for the same amino acid sequence of said specific collagenase. Merely by way of non-limiting example, one of the possible algorithms which can be used for the processes for optimization of the nucleotide sequences coding for one of the *C. histolyticum* collagenases could be the OPTIMIZER algorithm (Puigbò P et al. OPTIMIZER: A web server for optimizing the codon usage of DNA sequences. Nucleic Acids Res. 2007; 35). This algorithm, which is freely available from the website http://genomes.urv.es/OPTIMIZER, makes it possible to optimize the nucleotide or amino acid sequence of the protein of interest in accordance with various parameters including the type of host organism selected for heterologous expression. Examples of servers and algorithms available and known to the person skilled in the art for achieving optimization of sequences of interest include: JCAT (Grote, A et al 2005 JCat: a novel tool to adapt codon usage of a target gene to its potential expression host. Nucleic Acids Res., 33, W526-W531) and UpGene (Gao, W., et al 2004 UpGene: Application of a web-based DNA codon optimization algorithm. Biotechnol. Prog., 20, 443-448).

It is therefore clear that the person skilled in the art does not require further teaching in order to achieve step a) of the method described above since it is sufficient to know the amino acid sequence(s) or the nucleotide sequence(s) desired for reproduction and the main characteristics of the host organism in order to use the programs available freely (or at a cost) to obtain the desired optimized nucleotide sequences.

In one embodiment the desired recombinant collagenases are therefore those coding for the wild nucleotide sequences starting from ColG (code GenBank D87215.1) and ColH (code GenBank D29981.1), and the host organism for optimization will be selected from bacterial strains defective for the production of endogenous proteases. The optimization program therefore will indicate the codons found more frequently in the most expressed genes of bacteria of which there are also bacterial strains defective for the production of endogenous proteases. For example, if it is desired to use a particular *E. coli* strain as a bacterial strain defective for the expression of endogenous proteases, it will be sufficient to use an *E. coli* bacterial strain as a reference for optimization. In the examples described below, which are in no way limiting however, the use of the *E. coli* K12 strain is mentioned by way of example as a 'host' strain for optimization. With *E. coli* denoted as a host organism the optimization process generates two optimized nucleotide sequences referred to in this instance as SEQ ID NO 1 and SEQ ID NO 3.

The expressed SEQ ID NO 1 and SEQ ID NO 3 generate two amino acid sequences—SEQ ID NO 2 and SEQ ID NO 4 respectively which are identical (with the exception of the signal peptide) respectively to those published for *C. histolyticum* collagenases in Genbank by Matusushita (Matsushita O, et al. Gene Duplication and Multiplicity of Collagenases in *Clostridium histolyticum* (Journal of bacteriology, 1999, p. 923-933) and Yoshihara (Yoshihara K et al. Cloning and Nucleotide Sequence Analysis of the colH Gene from *Clostridium histolyticum* Encoding a Collagenase and a Gelatinase. 1994 Journal of bacteriology p. 6489-6496), having the respective codes D87215.1 and D29981.1.

The optimized nucleotide sequence coding for one of the *C. histolyticum* collagenases, obtained as described above, is then expressed within a relevant host cell before insertion of said sequence, as a fusion protein, in an inducible expression vector.

In one embodiment therefore, the *C. histolyticum* recombinant collagenases produced are *C. histolyticum* collagenase ColG and/or *C. histolyticum* collagenase ColH coded, respectively, from the wild nucleotide sequences code GenBank D87215.1 for ColG and code GenBank D29981.1 for ColH and from the optimized nucleotide sequences SEQ ID Nos 1 and 3.

In the present description the expression 'fusion protein' means a chimeric protein of which the amino acid sequence is given by the expression of a DNA sequence coding, in the correct reading frame, for one of the *C. histolyticum* collagenases linked to a protein or peptide having a specific function. 'Specific function' means, for example, localization in a particular cellular compartment of the expressed collagenase, isolation thereof from all the bacterial proteins produced (for example a tag sequence), a sequence which renders the collagenase soluble or more soluble, and more generally any function which makes it possible to improve any step of the method disclosed herein. It will be possible to fuse the sequence coding for the protein or peptide having a specific function to the 5' or 3' of the sequence coding for the collagenase in accordance with the function with which it is desired to associate said collagenase.

Polypeptides or proteins adapted for use in fusion proteins for the purpose of facilitating purification of a desired protein are known in the literature, as are vectors (commercial ones also) able to form fusion proteins with a sequence for purification already inserted in the vector itself and ready to be fused to the protein of interest.

In one embodiment the function of said protein linked to the collagenase consists in increasing solubility and in facilitating the process of purification of the collagenase itself. In the present description the protein (or peptide) to be linked to the collagenase can be known as a 'purification tag'. Purification tags which can be used for the purposes of the present invention can be selected from the group comprising: poly/hexahistidine, glutathione S-transferase (GST), thioredoxin, maltose binding protein (MBP), protein A fragment of *staphylococcus aureus* (ZZ), peptide with affinity for streptavidin (strep-tag), and flag peptide. The his-tag, which leads to precipitation of the fusion proteins produced from the host cells, is not suitable as a purification tag in the present invention.

The fusion protein according to the present description can also be produced by inserting a binding sequence as defined herein between the nucleotide sequence coding for the collagenase and the nucleotide sequence coding for a peptide/protein having specific functions.

In the present description the binding sequence can be a nucleotide sequence coding for at least one cut site for a proteolytic enzyme of which the function consists in making it possible to separate the two amino acid sequences coding, respectively, for a *C. histolyticum* collagenase and a peptide/protein having specific functions. Such functions can be that of purification or identification tags.

As defined herein, the binding sequence can comprise at least one recognition site for an enzyme with proteolytic action. For example, it can have one or more recognition sites for, for example, factor Xa, enterokinase and other specific endopeptidases. Taking into account the common use in laboratory practice of enzymes with proteolytic activity, the person skilled in the art does not require further information and teaching to select the type of enzyme and the corresponding recognition site to be inserted within the binding sequence. It is obvious to any average person skilled in the art that any cut site for a proteolytic site which is present merely in the binding sequence of the fusion protein and therefore does not cut any of the proteins comprised by the fusion protein but only cuts between them is to be considered as suitable.

In a further embodiment the cut site for separating the two components of the fusion protein may be already present in the tag component, as is the case of the MBP protein in the pMAL™ vector (from New England Biolabs). In the case of use of commercial systems for the formation of fusion proteins and any correlated purification systems, the person skilled in the art can simply follow the manufacturer's instructions.

One possible embodiment therefore can provide the MBP protein linked to the recognition site Xa, for example as in the vector pMAL-C2X. Given that the sequence having specific functions can be fused before or after that of the collagenase, accordingly, the binding sequence can be positioned at the 5' or 3' of the nucleotide sequence of the *C. histolyticum* collagenase which it is desired to express. In particular, it is therefore possible to design at least two sequences relative to the fusion protein according to the invention which will be, ordered from 5' to 3', formed by: X-Y-Z or Z-Y-X where X=peptide/protein sequence with a specific function, Y=the binding sequence, Z=*C. histolyticum* collagenase sequence.

In one embodiment of the invention the MBP protein is not separated from the recombinant ColG or ColH produced.

In fact, it has been surprisingly found by the inventors that the fusion proteins MBP-ColG and MBP-ColH described herein not only are produced at a very elevated yield by the method of the invention, but, in comparative tests with ColH and ColG, exhibit comparable collagenase activity which lasts longer, however, compared to unfused proteins.

An inducible expression vector is generally (and in the present description also) understood to mean a vector which expresses one or more relevant proteins under the control of an inducible promoter. This type of vector makes it possible to decide, in an expression system, when to activate and when to terminate the expression of the relevant recombinant protein(s). Apart from ensuring, in the present description, the expression of said fusion protein by the presence of an inducible promoter sequence and of essential control sequences including at least one transcription start sequence and a termination sequence, this vector therefore also makes it possible to control the duration and levels of said expression. The expression of said fusion protein is therefore controlled by the presence of the inducible promoter which, in the absence of the suitable inducer, does not induce expression of the protein under its control and that of the protein(s) to which it is operatively linked. By way of non-limiting example of the present invention, inducible promoters that can be used include: the inducible promoter Ptac under the control of the operon Lac and the promoter of T7 RNA polymerase in which the gene coding for T7 RNA polymerase is inserted in the genome of suitable bacterial strains under the control of the Pbad promoter inducible by the presence of arabinose in the culture medium.

Furthermore, in accordance with the present description the inducible expression vectors may comprise one or more control sequences, operatively linked to said fusion protein. Such control sequences can be selected from, but are not limited to, the group comprising: an untranslated 5' sequence containing a binding site for the ribosome, a sequence coding for a repressor, an operator sequence, a replication origin and a selection marker. Of course, any suitable sequence with a function for controlling the processes of transcription and translation of the fusion protein, known to the person skilled in the art and not described above, is to be considered as an integral part of the present description.

The expression 'operatively linked' means that the nucleotide sequence coding for the fusion protein, as defined in the present description, is arranged in functional relation to said control sequences so as to enable transcription and translation of said nucleotide sequence coding for a fusion protein within a host cell.

In specific embodiments of the invention the inducible expression vectors which can be used are selected from the group of vectors comprising the following classes of vectors: pMAL, pREST, pGEX, pTAC, pFLAG, pET and pT7.

The examples below illustrate exemplary but non-limiting embodiments of the invention such as: the use of the pMAL-C2x vector, belonging to the pMAL class of vectors, with the inducible promoter Ptac and the use of the pRSET-A vector, belonging to the PRSET class of vectors, with the inducible promoter of T7 RNA polymerase. In the MBP-ColG and/or MBP-ColH embodiment the use of the pMAL vectors is clearly advantageous since it makes it possible to obtain directly the desired fusion protein. Given the information provided here, the formation of the structure is clearly within the capability of the average person skilled in the art.

The use of inducible expression vectors, the insertion in their polylinker of relevant sequences and the transformation of host cells are experimental practices taught, step-by-step, in laboratory manuals, in textbooks and also, in the case of commercial vectors and commercial host cells, in manufacturer's instructions and therefore no further details will be provided in this regard in the present description.

In order to induce expression of a relevant protein, for example the fusion protein as described above within a host cell it is necessary, as is known to the person skilled in the art, to insert the nucleotide sequence coding for said relevant protein into the selected inducible expression vector. Such an insertion, by digestion with restriction enzymes of the nucleotide sequence and of the inducible vector, and any addition of sticky ends, is a common procedure within laboratory practice and is fully documented in any molecular biology manual and therefore does not require further explanation in this description.

The expression vector containing the nucleotide sequence coding for the fusion protein operatively linked to the sequences necessary for its expression and present in the vector (and therefore arranged so as to be expressed by said vector in an inducible manner once introduced in a suitable host organism) is subsequently used to transform a bacterial strain defective in the expression of endogenous proteases. The main feature of the strain used for the transformation is the lack of any proteases, which prevents hydrolysis of the expressed protein and therefore the presence in the host cell of multiple isoforms of the fusion protein.

In accordance with the above, bacterial strains defective in the expression of endogenous proteases which can be used for the expression of collagenase can be selected from the group comprising: lysogenic strains of *Escherichia coli* from the D3 series, strains of *Escherichia coli* with the lon and/or ompT and/or dnaJ genotype and BL21, BL21 AI, C600, CJ236, GC5, GM48, HB101, JM83, JM101, JM103, JM105, JM107, JM109, JM110, K802, LE392, MC1061, MM294, NM477, NM522, NM554, NM621, RR1, χ1776, Rosetta(DE3)pLysS, DH5α, DH10B, ER2566, CAG597, CAG629, ER2508, UT5600, CAG626, PR1031, KS1000, ER2507 and TB1 strains of *Escherichia coli* or derivatives thereof.

As mentioned above, the fusion protein according to the present invention codes for one of the *C. histolyticum* collagenases and for a peptide/protein having specific functions. The *C. histolyticum* collagenases are enzymes capable of hydrolyzing virtually all the isoforms of collagens and hydrolyze the Xaa-Gly bond in the SEQ ID NO 5 sequence, in which Xaa is any amino acid.

The method disclosed herein makes it possible to produce biologically active *C. histolyticum* recombinant collagenases, where 'biologically active' means that they exhibit collagenase activity, more specifically are also capable of recognizing in three-dimensional form (in contrast to gelatinases) and of hydrolyzing collagen molecules at the Xaa-Gly bond of SEQ ID NO 5.

In particular, in accordance with one embodiment the method disclosed herein makes it possible to obtain higher molecular weight (and therefore less degraded) isoforms of *C. histolyticum* collagenase ColG and *C. histolyticum* collagenase ColH in soluble, biologically active form and at a concentration of at least approximately 140 mg/l of bacterial culture of said form. Higher molecular weight isoforms are known in the literature and, for *C. histolyticum* collagenase ColG, have a molecular weight of approximately 116 kDa and, for *C. histolyticum* collagenase ColH, have a molecular weight of approximately 116 kDa. In one embodiment in which the *C. histolyticum* collagenases are produced as fusion proteins, the molecular weight is calculated by adding the molecular weight of the linked protein to the molecular weight of the collagenases. In a specific embodiment in which ColG and ColH are to be produced and the linked protein is the maltose binding protein (MBP), the molecular weight of the fusion proteins produced therefore will be approximately 140 KDa for MBP-ColG and approximately 140 KDa for MBP-ColH.

As described above, the host bacterial cell with the inducible expression vector containing the gene coding for the fusion protein can be transformed by any of the transformation methods known to the person skilled in the art, for example the electroporation method and the transformation method with calcium chloride. Such transformation is explained, step-by-step, in textbooks and laboratory manuals and the person skilled in the art will be able to achieve such transformation without any inventive effort and without the need for further explanation in this description.

The transformed bacterial cells will be subsequently placed in a culture, for the purpose of enabling expression of the relevant protein as indicated above, by adding a suitable inducer. The preparation of the culture medium for growth of the transformed bacterial cells is well-known to the person skilled in the art, who will be able to identify, without the need for further technical explanation in this description, the suitable medium on the basis of the transformed bacterial strain. It should be noted that ready-made bacterial culture media are also available on the market and can be used by the person skilled in the art without the need for any inventive step. The examples below illustrate exemplary, clearly non-limiting embodiments of the invention which provide the use of the Terrific Broth culture medium ([12 g/L tryptone, 24 g/L yeast extract, 0.4% glycerol, 17 mM $KH_2PO_4$ and 72 mM $K_2HPO_4$]) mixed with approximately 0.2% of glucose if the BL21 AI strain of *E. coli* is selected as a host bacterial strain.

On the other hand the selection of a temperature adapted to bacterial growth and to induction of expression of the recombinant collagenase in the host bacterial strain is an extremely delicate matter. The ideal temperature is ambiguous from the prior art, with some works indicating a temperature of 25° C. (Ducka et al. A universal strategy for high-yield production of soluble and functional clostridial collagenases in *E. coli*. 2009 Appl Microbiol Biotechnol 83:1055-65) in contrast with others which indicate an ideal temperature of 37° C. (patent application US 2008/0233614). Both works cited above emphasise that such temperatures have been identified on the basis of comparative studies in which various temperature ranges, comprising a temperature of approximately 30° C., have been considered and assessed in terms of maximum expression of recombinant collagenase.

In the present description the authors identify a temperature comprised within the range of 28-32° C., extremes included, as an ideal temperature for bacterial culture growth and for induction of recombinant collagenase on the basis of maximum expression of biologically active collagenase, quantifiable in terms of a yield greater than approximately 140 mg/l of bacterial culture. Such a growth and induction temperature is, in particular, a temperature comprised in the range of 28-32° C., extremes included, that is to say a temperature of approximately 28° C., of approximately 28.5° C., of approximately 29° C., of approximately 29.5° C., of approximately 30° C., of approximately 30.5° C., of approximately 31° C., of approximately 31.5° C. and of approximately 32° C.

Such a temperature range enables increased expression of biologically active, soluble collagenase.

In a specific embodiment the growth temperature of the bacterial culture and of induction of the recombinant collagenase is a temperature of approximately 30° C.

Induction of expression of the fusion protein which, in accordance with the present description, codes for one of the *C. histolyticum* collagenases and for a peptide/protein having, within the host cell, is obtained by the addition of a suitable inducer to the transformed bacterial culture. The process of heterologous induction of expression of a relevant protein within a host cell is an experimental procedure well known to the person skilled in the art. The person skilled in the art knows that the selection of the inducer is linked to the type of inducible expression vector selected and therefore, if commercial vectors are used, that the type of inducer and also the experimental conditions will be detailed in the manufacturer's instructions.

As already described above, in specific embodiments of the invention the inducible expression vectors are selected from the group of vectors comprising the pMAL, pRSET, pGEX, pTAC, pFLAG, pET and pT7 class of vectors. As described above, in accordance with said selected specific embodiments, the inducers that can be used will be selected from the group comprising: isopropyl β-D-1-thiogalactopyranoside (IPTG) for the pMAL, pGEX, pTAC and pFLAG class of vectors, and arabinose for the pRSET, pET and pT7 class of vectors in the BL21-AI strain.

The examples below illustrate exemplary, non-limiting embodiments of the invention such as induction by the addition of IPTG, at a final concentration of approximately 0.3 mM, to the culture medium if the pMAL-C2X vector is selected as the inducible expression vector, or by the addition of arabinose at a concentration of approximately 0.2% if the expression vector selected is the inducible vector pREST-A.

Induction of expression of the fusion protein leads to the accumulation thereof within the induced bacterial strain. Extraction of the fusion protein, obtained as described above, from the bacterial cell can be achieved by any extraction method known to the person skilled in the art. Detailed extraction protocols of proteins from bacterial cells are conventional methods reported in textbooks and laboratory manuals and therefore the person skilled in the art does not require any further teaching in order to carry out point f) of the method described herein.

In one embodiment extraction can be achieved by lysis of the bacterial strain induced by standard methods using a common bacterial lysis buffer.

Purification of the fusion protein from all the bacterial proteins can be achieved by conventional chromatographic methods or, more simply, by using a peptide/protein having specific binding functions as described above.

In the embodiment in which such peptide/protein having specific functions is a purification tag, for example, the purification method (or methods) by affinity column chromatography can be used which therefore enables purification of the fusion protein expressed from all the bacterial proteins produced.

Such a purification step can be carried out by utilizing, for example, specific molecular interactions existing between purification tags and specific molecules or proteins, such as: interaction of the MBP (indicated as a possible tag) with the maltose molecule, or the increased affinity of the biotin (other possible tag) with streptavidin, or else interaction of GST (further possible tag) with its glutathione substrate, etc.

Any purification method in which purification tags are utilized and the purification methods correlated therewith therefore can be considered as suitable for carrying out point g) of the method disclosed herein.

As already demonstrated, the method described herein for the production of *C. histolyticum* recombinant collagenases makes it possible to obtain the relevant collagenase in the respective higher molecular weight isoforms with a yield greater than 140 mg/l of bacterial culture of said collagenase in soluble and biologically active form, which is a yield significantly greater than any other method based on the recombinant DNA technology reported in the known prior art. This unexpected and surprising result obtained by the method which is described herein and was not previously deducible is achieved owing to the specific combination, indicated by the inventors, of experimental means and conditions including, for example, the selection of a specific expression system as described above, of a structure for expression as described above and the selection of a particularly effective growth and induction temperature range (although temperatures contained within such a range were clearly reported in the literature as being less effective compared to others). The specific production of such higher molecular weight isoforms, in the amount of at least approximately 140 mg/l of soluble and biologically active bacterial culture of said isoform, is made possible by the combination of various parameters indicated in the method disclosed herein, including the selection of a host bacterial strain defective in the expression of some endogenous proteases, the selected expression structures, the optimization of the sequences to be expressed and the selection of an optimal expression and induction temperature range as indicated herein. The selection of the host strain makes it possible to limit the digestion of the expressed protein and therefore makes it possible to minimize the presence of biologically active isoforms of a molecular weight lower than the *C. histolyticum* collagenases of interest expressed heterologously. The present invention therefore provides a method for the production of *C. histolyticum* recombinant collagenase ColG and of *C. histolyticum* recombinant collagenase ColH which makes it possible, on the one hand, to significantly limit the presence of contaminants exhibiting lytic activity, even compared to commercially available collagenase preparations (as is evident from the comparison of FIGS. 5 and 8), to eliminate the problem of contaminants which are potentially harmful to humans and animals, but with the provision of a yield of soluble and biologically active collagenase (that is to say exhibiting collagenase activity comparable to that of wild proteins) much higher than those described in the literature for heterologous systems.

Furthermore, the present invention also provides a method for the preparation of a MBP-Col (G or H) fusion protein exhibiting improved collagenase activity compared to *C. histolyticum* native and recombinant collagenase, the proteins thus obtained and the use thereof.

The solubility of the active enzyme and the ease of recovery thereof in the method of the present description also make it possible to quantify, with ease and accuracy, the concentration of biologically active collagenase produced and therefore enable efficient calibration of collagenase preparations for commercial use, with a consequent limitation to the variability between batches. The independent expression of the collagenases according to the method disclosed herein also makes it possible to mix, at different ratios, the various collagenases produced separately, in accordance with the specific applications and technical requirements.

The collagenase mixtures of the invention therefore can be mixtures with predetermined concentrations of recombinant ColG and ColH as described herein, therefore also of MPB-ColG and MPB-ColH or else of combinations of the two types of recombinant protein produced, with and without MPB fused to the N terminal.

Furthermore, the authors of the present description have found that the collagenases obtained as described above are characterized by a collagenase activity which reveals an ability to extract more living cells, in numerical terms, than commercially available collagenase preparations (FIG. 12). Such an assessment has been made by the inventors using the in vitro cellular extraction assay, as defined above in the glossary. In particular, in the embodiment in which *C. histolyticum* recombinant collagenase G and *C. histolyticum* recombinant collagenase H are used, produced by the method disclosed herein, it will be possible to obtain an extractive yield of at least approximately $7.4 \times 10^5$ cells/ml and $8.2 \times 10^5$ cells/ml respectively compared to an extractive yield of approximately $5.2 \times 10^5$ cells/ml obtained with New Liberase (Roche) and an extractive yield of approximately $4.4 \times 10^5$ cells/ml obtained with collagenase P (Roche). This surprising result is also accompanied by the, likewise unexpected, observation that these cells preserve their differentiated phenotype, that is to say the ability to form, in vitro, stable cell-cell contacts and to form a differentiated pseudo-epithelium. In contrast, the cells treated with Liberase (Roche) and with collagenase P (Roche) appear to have a mesenchymal phenotype and, in this instance, the cells do not form contacts therebetween and have a morphology characteristic of cells in migration. The collagenases thus obtained therefore ensure that the differentiated phenotype of the extracted cells is maintained, which is extremely important in pancreatic islets, since if the cells comprising the islets lose cell-cell contact then they are no longer able to produce insulin. This capability translates practically into greater success of medical procedures aimed at the transplant of extracted cells, which procedures use the collagenases produced by the method disclosed herein.

In the present description the authors report, as seen also in the examples, that the *C. histolyticum* recombinant collagenases obtained using the method disclosed herein are not only produced in biologically active form, but also with a greater level of purity compared to current commercially available preparations (as already described above). This level of purity is not expressed merely in terms of absence of enzymatically active components, but also in terms of absence of toxic contaminants that are potentially harmful to the health of humans. In particular, this method being based on recombinant DNA technology and on the use of *E. coli* as a productive bacterium, it does not provide the use of culture media supplemented with bovine brain homogenates and therefore ensures that a product will be obtained which is free from contamination, for example is free from prion proteins. This characteristic of the collagenases obtainable by the method described herein therefore makes the use thereof particularly advantageous in terms of safety in applications within the medical field.

The present description therefore also relates to *C. histolyticum* recombinant collagenases characterized by the fact that the cells extracted from said collagenases maintain the differentiated phenotype and therefore are able to form cell-cell contacts, even in vitro, and *C. histolyticum* collagenases fused to the N terminal by the maltose binding protein MBP (MBP-Col), for example, coded by the pMAL vector. Such collagenases are obtainable by the method described above. In some embodiments the *C. histolyticum* recombinant collagenases are the *C. histolyticum* collagenase G and/or the *C. histolyticum* collagenase H and, in particular, their higher molecular weight isoforms, that is to say *C. histolyticum* ColG with a molecular weight of approximately 116 kDa and *C. histolyticum* ColH collagenase with a molecular weight of approximately 116 kDa. However, when fused to the MBP protein at the N terminal they have a molecular weight of approximately 140 kDa, as already indicated above.

The differentiated phenotype maintained by the extracted cells, obtained following extraction with the collagenases described herein and obtainable by the method of the invention is similar to that normally presented by the same type of cell in histological and in vivo preparations. That is to say the cells extracted with the collagenases described herein or with a mixture thereof or composition comprising them by standard extraction methods known to the person skilled in the art also maintain, in vitro, the phenotype normally presented by the same type of cells in vivo, i.e. the same morphological cellular characteristics and the same cell-cell interaction capabilities encountered in the tissue from which they originate.

Furthermore, the present description also relates to a composition comprising *C. histolyticum* recombinant collagenases as disclosed herein and, in one embodiment, a composition in which said *C. histolyticum* recombinant collagenases Col are *C. histolyticum* collagenase ColG and/or collagenase ColH.

Furthermore, the invention also relates to *C. histolyticum* recombinant collagenases in the form of MBP-Col H and MBP-Col G fusion proteins as described herein (see the examples and figures), wherein said proteins are extremely soluble and therefore provide an optimal production yield of soluble, enzymatically active recombinant enzyme, that is to say exhibiting collagenase activity, and are surprisingly more active, exhibiting much more activity in terms of time in comparative tests compared to *C. histolyticum* recombinant and non-recombinant collagenases Col H and Col G.

The present description therefore also relates to compositions comprising the *C. histolyticum* MBP-Col fusion proteins (collagenase G and/or collagenase H fused to the MBP protein at the N terminal) and to a kit comprising said proteins or said compositions.

The compositions of the invention can also comprise a mixture of known composition of one or more of the *C. histolyticum* recombinant collagenases described herein, for example ColG, ColH, MBP-ColG and MBP-ColH in any combination comprising two or more of said recombinant collagenases and a suitable excipient which may be, for example, a sterile saline solution (for example of calcium chloride or of sodium chloride) with a pH between approximately 6 and 9. The composition according to the invention can contain other additives, for example including glycerol and other substances commonly used for the preservation of compositions comprising enzymes.

As already mentioned, C. histolyticum collagenases are enzymes which are widely used in clinical practice as a result of their ability to efficiently digest collagen fibres and to thus enable isolation of somatic and/or stem cells. As already highlighted, the C. histolyticum recombinant collagenases produced by the method disclosed herein are characterized by an extractive yield which is higher, in terms of the number of living cells extracted, than that obtainable using the currently commercially available collagenase preparations. This characteristic of the C. histolyticum recombinant collagenases produced by the method described above renders said enzymes particularly suitable for use within the medical field. Taking into account what is already known in the known prior art in relation to the use of C. histolyticum collagenases, the use within the medical field can be, for example, in procedures for the extraction of vital stem and/or somatic cells from tissues. As demonstrated by the assays reported in the present description, the C. histolyticum recombinant collagenases also in the form of fusion proteins according to the present description make it possible, in contrast with commercially available C. histolyticum collagenases, for the cells extracted therewith to maintain the differentiated phenotype, primarily for the ability to form cell-cell contacts, even in vitro. In one embodiment this procedure consists in the isolation of vital islets of Langerhans from the pancreas. In this specific embodiment maintenance of the differentiated phenotype in the extracted cells and the consequent maintenance of the ability to form cell-cell contacts is essential in order to maintain the ability of said cells to form insulin.

The present description also relates to a kit for the extraction of stem and/or somatic living cells from tissues comprising one or more aliquots of a C. histolyticum recombinant collagenase composition of approximately 116 kDa ColG and/or ColH or in the form of MBP-ColH and/or MBP-ColG fusion proteins or mixtures thereof, as defined above. Said kit can also contain one or more aliquots of reagents useful for the extraction procedure used, including for example neutral and/or thermolysin proteases.

Islets of Langerhans are generally resuspended in physiological solution (0.9% NaCl saline solution).

Examples are shown below which aim to better illustrate the methods described in the present description, although these examples are in no way to be considered as a limitation of the description above and of the subsequent claims.

EXAMPLES

1. Design of the Synthetic Gene Sequences

An algorithm for optimization of the *Clostridium histolyticum* ColG and ColG gene codons called an optimizer (Puigbò P et al. OPTIMIZER: a web server for optimizing the codon usage of DNA sequences. Nucleic Acids Res. 2007 July; 35) was used to generate nucleotide sequences. The optimizer analyses any coding sequence and suggests alternative codons, taking as reference the codons most frequently used in the highly expressed genes (HEG) of numerous prokaryotic organisms.

The prokaryotic organism *Escherichia coli* and in particular the K12 strain was selected for the optimization process.

The optimization process generates two new genes corresponding to SEQ ID Nos 1 and 3 coding respectively for *C. histolyticum* collagenase G and H. The relative amino acid sequences, i.e. SEQ ID Nos 2 and 4, correspond to those present in Genbank with the codes D87215.1 and D29981.1 published respectively by Matsushita et al. (for Col G) and by Yoshihara et al. (for Col H).

2. Synthesis and Cloning of Synthetic ColG and ColH Genes

The optimized synthetic genes coding for ColG and ColH were artificially synthesized and inserted respectively in the pUCminusMCS vector (ColG) and in the pBluescript plasmid (ColH). The unique sites for the BamHI (5' end) and HindIII (3' end) restriction enzymes were inserted in both genes so as to allow cloning in the expression vectors.

The plasmid DNA of the pUCminusMCS vectors containing the optimized ColG sequence and the plasmid DNA of the pBluescript plasmid containing the optimized ColH sequence was subjected to digestion by the Bam HI and Hind III enzymes so as to separate the DNA fragment corresponding to the synthetic gene. The synthetic genes were inserted in the pMAL-C2X and pRSET-A plasmids by ligation reaction (FIGS. 1 and 2).

Both the collagenases are deprived of the original amino terminal end (signal peptide) and have two different sequences as a function of the selected expression vector. In the vectors of the pMAL-C2X series the sequence is substituted by the mal E gene sequence coding for the maltose binding protein (MBP) and by the recognition site for the factor Xa protease. A sequence containing a peptide formed of 6 histidines (his-tag) followed by the leader portion of gene 10 of the T7 bacteriophage are present in succession in the vectors of the pRSET-A series. In either case the fragments fused in the correct reading frame in the portion to the 5' of the gene ensure high levels of transcription and translation. Furthermore, the resultant peptides have better solubility and folding characteristics compared to the native proteins. The peptides in the terminal amino portion are separated from the ColG or ColH sequence by a recognition site of the factor Xa protease or enterokinase.

The expression vectors were verified by digestion with restriction enzymes (including the sites used for cloning) and by direct sequencing of the 5' end of the gene.

3. Induction of the Recombinant Collagenases

The bacterial colonies were grown in Terrific Broth ([12 g/L tryptone, 24 g/L yeast extract, 0.4% glycerol, 17 mM $KH_2PO_4$ and 72 mM $K_2HPO_4$]) mixed with ampicillin (100 g/ml) and glucose (0.2% or 0.1% respectively for the bacterial strains containing the expression vectors derived from pMAL-C2X or pRSET-A) in Erlenmeyer flasks placed in an orbital oscillator at a temperature of 30° C. and at 260 rpm. Once the culture had reached the optical density $OD^{600}$ of 0.6, expression of the recombinant proteins was begun by adding IPTG to the culture medium at a final concentration of 0.3 mM (for the bacterial strains containing expression vectors derived from pMAL-C2X) or with arabinose at a concentration of 0.2% (for bacterial strains containing expression vectors derived from pRSET-A). The cultures are kept at a temperature of 30° C. with stirring (260 rpm) for 3 hours.

4. Extraction and Purification of the Recombinant Proteins

After the induction phase the cells were collected by centrifugation (3500 g×10 min). The cellular pellet was resuspended in 5 ml of column buffer per 100 ml of culture medium. The suspension was subjected to 6×20 sec sonication cycles at 0° C. (40% duty cycle, output control 5) in a Branson Sonifier 250 using a microtip.

The suspension was therefore centrifuged at 9000 g×20 min at 4° C. The supernatant was collected and the concentration of the proteins was determined using column buffer= (tris HCl 20 mM, NaCl 200 mM, EDTA 1 mM, pH 7.4).

5. Synthesis of Collagenase G and H, Amount Produced From 1 Liter of Bacterial Culture, Assessment of Enzyme Activity Using Gelatine Zymography.

After extraction from the productive bacteria the class I and II recombinant collagenases (pMAL-ColG and pMAL-ColH) were analyzed both quantitatively (synthesis) and qualitatively (proteolytic activity and ability to extract cells from a three-dimensional type-I collagen matrix). Total extracts from productive bacteria were assessed by SDS-PAGE and zymography. A first assessment regarding the amount of synthesized pMAL-ColG and pMAL-ColH was established from this first analysis. FIG. 3 shows the SDS-PAGE relative to the production of pMAL-ColG and pMAL-ColH; Bredford protein analysis of the samples and densitometric analysis of the electrophoretic bands made it possible to establish that approximately 160 mg of pMAL-ColG or pMAL-ColH are obtained from 1 liter of bacterial culture induced for 3 hours at 30° C. by the addition of IPTG at a final concentration of approximately 0.3 mM.

The enzymes obtained were assayed by the method of gelatine zymography with regard to their ability to 'digest' this substrate; these experiments were carried out both with unpurified synthesis products (crude extracts from productive bacteria), and with purified proteins formed by the pMAL-ColG or pMAL-ColH structure which carry the maltose binding protein (MBP) in bound form (FIG. 3). The latter were purified by amylose column affinity chromatography (Biolabs) (FIG. 4) and examined after elution using a maltose solution [10 mM] both by SDS-PAGE and by zymography. Both the forms with bound MBP and those in which the maltose binding protein had been removed by enzyme digestion carried out with factor Xa were studied (FIG. 5).

The purified pMAL-ColG and pMAL-ColH, by affinity chromatography, were examined by size exclusion chromatography with Superdex 200 FPLC; the elution profiles obtained are shown in FIG. 6 and reveal a rather limited number of contaminants. In any case these contaminants did not demonstrate any effects of cellular toxicity in experiments in which cells were released from a type-I collagen matrix by using the recombinant collagenases produced.

6. Analysis by Gelatine Zymography

The recombinant collagenases obtained after having been extracted from the productive bacteria were mixed in an electrophoretic buffer devoid of reducing agents (2β-mercaptoethanol or the like); the samples also are not subjected to boiling in order to avoid the loss of enzyme activity. The samples thus prepared were stratified in polyacrylamide gel containing gelatine at a concentration of 3 mg/ml. After the electrophoretic run at 100 volts for 45 minutes the gels were washed with a 2% TRITO X-100 solution in $H_2O$ containing 0.02% $NaN_3$ (3 times×20? for each wash). They were then incubated overnight at 37° C. and then dyed with a $H_2O$-acetic acid-methanol solution in the ratios 5:1:5 containing 0.8% Coomassie Brilliant Blue for 3 hours with stirring. The excess dye was removed using a 5% $CH_3COOH$ solution.

7. Analysis of the Densitometric Profiles of the Lytic Activity Demonstrated by Gelatine Substrate Zymography The recombinant collagenases G and H produced and the collagenases produced by Roche and Serva, more specifically: Liberase HP (first generation collagenases G and H, Roche), collagenase P (less pure mix of collagenases G and H, Roche) and NB1 (collagenases G and H, Serva) were separated using gelatine zymography by loading between 1.25 and 10 mg/well. The various collagenases were resuspended in PBS at a concentration of 1 μg/μl and incubated at various temperatures (−20° C., +4° C. and at room temperature) for various numbers of days (1, 4, 7 and 18 days); any type of collagenase scarcely resuspended (from the lyophilized form) at a concentration of 1 μg/μl in PBS was used as a control. After the electrophoretic run the gels were dyed as described above and the profiles of the lytic bands of the various collagenases obtained at various incubation times at various incubation temperatures were compared using Image 1.42 software from NIH in order to show the variability of the peaks and the pore disappearance over time. Based on these two parameters it is possible to determine greater or lesser stability of a sample compared to the others.

8. Culture of the Cells Within a Three-Dimensional Gel and Analysis of the Phenotype Using Confocal Microscopy The epithelial cells ECV 304 were cultivated in three-dimensional type-one collagen fibril gel (rat tail BD Bioscience 3.9 mg/ml in 0.02 M acetic acid). For this purpose they were resuspended in 500 μl of 2× medium (containing a double concentration of 10% bovine foetal serum+2 mM glutamine+50 μg/ml streptavidin and 50 μg/ml penicillin) containing 50 mM of sodium carbonate and mixed in a ratio of 1:1 with the collagen; the cells were then introduced into wells and cultivated in 96-well plates (100 μl per well). After polymerization obtained at 37° C., 150 ml of complete medium were added and the cells were incubated at 37° C. in $CO_2$ at 5%. The day after, the cells were treated with the enzymes col G and col H at a concentration of 0.3 mg/ml. After complete digestion of the collagen and complete release of the cells (approximately 2 hours), the cells were fixed with 4.7% formaldehyde in PBS for 15 minutes at 37° C. and observed by confocal microscopy (Olympus) in order to assess their morphology.

9. Digestion of 3D Collagen Gel Containing Endothelial Cells; Analysis of Cellular Morphology and of Cellular Vitality.

Since zymography merely indicated the enzyme activity exhibited by the enzymes on the 'linearized' but not 'spatial' sequences (quaternary structure of the substrate), an extraction assay was carried out of $ECV_{304}$ endothelial cells grown in a three-dimensional type-I collagen gel (3D Coll type-I) similar to that prepared as indicated above. The $ECV_{304}$ cells have the ability to form, within this 3D substrate, pseudo-differentiated structures similar to vessels. The 3D Coll type-I gels containing the $ECV_{304}$ were treated with various concentrations both of the enzymes produced by us and with some commercial enzymes (mixtures of collagenases G and H (Liberase HP, Roches; NB1, Serva), thermolysin and neutral protease) currently used for extraction of islets of Langerhans. Spectrophotometric assays were used to establish the kinetics of digestion of the 3D Coll type-I gels as a function of the concentration of the enzymes produced by us and relative to the digestive ability of the various commercial enzymes used, the ability to release the $ECV_{304}$ contained in the 3D collagen matrix and their effects relative to cellular morphology (ability to form stable cell-cell contacts) and relative to their vitality (ratio of living cells to dead cells) (FIG. 7).

In extraction experiments from 3D Coll type-I gels the extractive abilities of some commercial enzymes and their ability to release islets of Langerhans obtained from the pancreas of donors and contained in this matrix are compared after analysis by electrophoresis and by zymography with regard to their protein and proteolytic composition (FIG. 8). On the one hand the extractive ability was established as the number of islets extracted, and on the other the effects of the extractive process on the vitality of the cells forming the islets themselves was established as the ratio of living cells/dead cells (FIGS. 9 and 10). As is shown in FIG. 9, Liberase (mixture of collagenases G and H produced by Roche) was examined at various concentrations, and more specifically: a concentration double that normally used in extractive processes in accordance with the Edmonton protocol, the concentration normally used and therefore ⅒, 1/100 and 1/1000 of that normally used in terms of extractive ability. The results obtained show that, with regard to the release of islets of Langerhans from 3D ColI type-I gel, better results are obtained using a concentration one tenth of that currently used and that, furthermore, more of the cells thus extracted are living. Similar experiments have been carried out using $ECV_{304}$ cells which have confirmed, at the concentration identified, an improved extractive yield with the lowest level of toxicity. The analysis of various commercial enzymes at the concentration documented in the protocols currently used to purify islets of Langerhans to be transplanted in patients suffering with type-1 diabetes has shown (FIG. 10) that all the enzymes used and analyzed killed approximately 25% of the cells forming the islets of Langerhans and even 75% in the case of neutral protease. This behaviour was also observed relative to the extraction of $ECV_{304}$ cells; with regard to the latter the collagenases produced as described above were also assayed and demonstrated an extractive ability similar, but without modification to the phenotype level.

10. Stability of the Enzymes Synthesized by Us Relative to Some Commercial Enzymes.

A series of assays relating to the stability of the collagenases produced were carried out and in particular the zymographic profiles of various commercial enzymes and of pMAL-ColG and pMAL-ColH are compared.

For each sample separated using gelatine zymography the densitometric profile was established using the Image 1.42 program, and the profiles obtained from control samples (enzyme from the lyophilized batch) were compared to the corresponding samples which, after being regenerated in a suitable buffer (activating the enzymes to be analyzed), were incubated respectively for 1, 4, 7 or 18 days at −20° C., 4° C. or at room temperature (r.t.), see FIG. 14. This type of analysis demonstrated much greater stability of the pMAL-ColG produced by the method described herein compared to all the other molecules analyzed; inter alia at room temperature also, this behaviour can be attributed to the high level of purification of the molecule and to the absence of endogenous enzymes which may induce the degradation thereof.

11. Catalytic Activity of the Collagenases Synthesized by Us, Assessed on the Synthetic Substrate Suc-Gly-Pro-Leu-Gly-Pro-AMC.

The collagenases and MPB collagenases produced in accordance with the present description were assayed on the synthetic substrate Suc-Gly-Pro-Leu-Gly-Pro-AMC which, as demonstrated by Kojima et al. 1979, is a substrate specific to collagenase. The enzyme activity was established by an indirect method; various concentrations of the synthetic substrate (Suc-Gly-Pro-Leu-Gly-Pro-AMC) were subjected to the action of the collagenase G and H produced by us. The action of the enzymes analyzed consists in the splitting of the synthetic peptide without activation of the fluorochrome AMC, but with the release of the substrate Gly-Pro-AMC (still reactive). The latter is specifically recognized by the enzyme dipeptidyl peptidase 4, an endopeptidase able to split the peptide bond at the amine end where the penultimate amino acid is a proline preceded by glycine or alanine, and with less affinity to other amino acids; the cut on the Gly-Pro-AMC dipeptide induces activation of the fluorochrome. The analysis carried out (see FIG. 15 'ColI G and ColI H Kinetics') reveals the digestive ability of the two enzymes, which show comparable kinetic digestion curves, when assayed at various concentrations of the synthetic substrate and using a known concentration of the dipeptidyl peptidase 4 enzyme. The maximum mean rate calculated from the enzyme kinematics for the two enzymes were respectively 0.063 units per sec for ColI G and 0.080 units per sec for ColI H; with an efficiency of activity on the synthetic substrate of ColI H greater by approximately 2.4% compared to ColI G.

12 Analysis of Stability of the Collagenases According to the Present Description.

It was demonstrated that, in the fusion proteins produced, the MBP does not interfere with the enzyme activity of the enzymes according to the present description and, moreover, confers greater solubility during the purification process. In fact, when the collagenases G and H according to the invention, which carry MBP in bound form, are purified by amylose resin affinity chromatography, eluted by competition with free amylose and, after elution, are dialyzed against a suitable buffer, no problem is observed in the solubilisation of the enzymes. Otherwise, after purification by probond resin affinity chromatography and after dialysis against a suitable buffer, both the enzymes precipitate when using the products of the synthetic genes for the two collagenases which do not carry MBP, but instead the His-tag.

We therefore believe that the collagenases carrying MBP in bound form afford advantages both in terms of stability and solubility.

13. 'Ex vivo' Extraction of Islets of Langerhans From Murine Pancreases.

In experiments carried out on mice killed by cervical dislocation following sedation with ethyl ether, the extractive ability of the islets of Langerhans was analyzed with regard to the collagenases according to the present description. In particular, a mixture in the ratio of 1:1 of ColI G [0.5 mg/ml] and ColI H [0.5 mg/ml] and MBP ColI G and H in the same ratio was used, to which thermolysine was added of which the optimal concentration was determined to be 10 μg/ml.

The extractive ability of the enzyme mix indicated above was compared to that of the Roche Liberase at the same concentrations [0.5 mg/ml] using a total of 7 ml of solution, 3 of which were used for perfusion of the organ and the remaining 4 ml were added to the removed pancreas. The results obtained show that the mix of collagenases according to the present description, devoid of contaminants, extracts islets which exhibit improved morphology (with cells that maintain their differentiated phenotype) compared to those obtained with the digestion of Liberase, which exhibit a more 'lax' morphology, i.e. less stable cell-cell contacts under the same experimental conditions. Furthermore, when comparing the amounts of enzymes used in the present experiment compared to the protocols used by Serva, for example the collagenase NB 8 Broad Range (cat. no. 1756), it is noted that in this procedure the collagenases are used in a solution at a concentration of [2.5 mg/ml] for a total of 7 ml and therefore of 17.5 mg total enzymes; against a total of 3.5 mg total recombinant collagenases G and H used herein for the same procedure.

Specific Activity of the MBP G and H Collagenases

In order to determine the specific activity of the recombinant collagenases G and H produced by us, we also used the 'Collagenase Substrate Kit (for quantitative collagenase determination) code 27672/27670 from Sigma'(*) in which 1 μmol of Gly-Pro-Ala from the peptide Z-Gly-Pro-Gly-Gly-Pro-Ala (Fluka 27673) is released within one minute at pH 6.3 at a temperature of 37° C.

The following results were obtained from the comparative analysis of the mix of recombinant collagenase G and H MBP produced according to the present description, in the ratio of 1:1) and Liberase (Roche, containing collagenases G and H in a ratio of 1:1)
  mix of recombinant ColG:ColH (1:1)=0.68 units/mg of protein
  Liberase (Roche)—0.40 units/mg of protein
This indicates that the enzymes produced in accordance with the present description with the associated MBP exhibit a digestive efficiency of 42.2% more than the Liberase produced by Roche.

Furthermore, comparing the activity of the recombinant collagenases G and H with and without the MBP it was possible to observe that whilst, after 15 minutes of activity, the amount of substrate digested by the collagenase forms G and H is the same, both with and without MBP, after 90 minutes:
  there are no specific differences between the two enzyme forms for col H both with and without MBP;
  whereas the MPB-Col G form is 14.8% more effective in digestion of the substrate than the form without MBP, suggesting functional stability for the former.

The fact that the forms which carry MBP in bound form are more stable than those which do not has already been demonstrated in the stability experiments in which the molecules synthesized according to the present description were assessed compared to commercial molecules, see point 10 of the examples (FIG. 14).

(*) W. Grassmann, A. Nordwing, Z. Physiol. Chemie 322, 267 (1960).

BIBLIOGRAPHY

Balamurugan et al., Harmful Delayed Effects of Exogenous Isolation Enzymes on Isolated Human Islets: Relevance to Clinical Transplantation. American Journal of Transplantation 2005; 5: 2671-2681

Ducka et al. A universal strategy for high-yield production of soluble and functional clostridial collagenases in *E. coli*. Appl Microbiol Biotechnol 2009 83:1055-65

Gao, et al. Application of a web-based DNA codon optimization algorithm. Biotechnol. Prog., 2004 20, 443-448

Grote et al. JCAT: a novel tool to adapt codon usage of a target gene to its potential expression host. Nucleic Acids Res., 2005 33, W526-W531, Johnson et al. Collagenase and human islet isolation. Cell Transplant. 1996; 5:437-52

Kin et al. Enhancing the Success of Human Islet Isolation through Optimization and Characterization of Pancreas Dissociation Enzyme. American Journal of Transplantation 2007; 7: 1233-1241

Kin et al. Detrimental effect of excessive collagenase class II on human islet isolation outcome. Transplantation international 2008 1059-1065

Matsushita et al. Gene Duplication and Multiplicity of Collagenases in *Clostridium histolyticum*. Journal of bacteriology 1999, p. 923-933

Puigbò et al. OPTIMIZER: a web server for optimizing the codon usage of DNA sequences. Nucleic Acids Res. 2007; 35

Vargas et al. Engraftment of islets obtained by collagenase and Liberase in diabetic rats: a comparative study. Pancreas. 2001; 23:406-13

Yoshihara et al. Cloning and Nucleotide Sequence Analysis of the colH Gene from *Clostridium histolyticum* Encoding a Collagenase and a Gelatinase. Journal of bacteriology 1994 p. 6489-6496

US200800233614: PRODUCTION OF RECOMBINANT COLLAGENASES COLG AND COLH IN *ESCHERICHIA COLI*

The invention claimed is:

1. A method for production of a recombinant *C. histolyticum* collagenase comprising:
   a) designing an optimized nucleotide sequence for expression of said recombinant *C. histolyticum* collagenase, wherein said optimized nucleotide sequence is SEQ ID NO: 1 or SEQ ID NO: 3;
   b) introducing, in an inducible expression vector, a nucleotide sequence coding for a fusion protein, wherein said nucleotide sequence comprises said optimized sequence fused to a purification tag coding sequence and a soluble polypeptide coding sequence, and wherein said nucleotide sequence is operatively linked to an inducible promoter sequence, a transcription start sequence, and a termination sequence;
   c) transforming a bacterial strain defective in expression of endogenous proteases with said expression vector;
   d) culturing said transformed bacterial strain at a temperature in a range from 28° C. to 32° C.;
   e) inducing expression of said fusion protein by adding a suitable inductor in said bacterial strain;
   f) extracting the fusion protein from the induced bacterial strain; and
   g) purifying said fusion protein;
   wherein said method provides a yield higher than 140 mg/l of culture of said recombinant *C. histolyticum* collagenase in soluble and enzymatically active form.

2. The method according to claim 1, wherein said temperature is about 30° C.

3. The method according to claim 1, wherein said optimized sequence is fused to said soluble polypeptide coding sequence through a binding sequence coding for at least one cleavage site for a suitable proteolytic enzyme and further comprising:
   h) obtaining said recombinant *C. histolyticum* collagenase by enzymatically cleaving said at least one cleavage site.

4. The method according to claim 1, wherein said recombinant *C. histolyticum* collagenase is a fusion protein MBP-*C. histolyticum* ColG or MBP-*C. histolyticum* ColH.

5. The method according to claim 3, wherein said recombinant *C. histolyticum* collagenases is *C. histolyticum* ColG collagenase or *C. histolyticum* ColH collagenase.

6. The method according to claim 1, wherein said expression vector is selected from the group consisting of the vector classes: pMAL, pRSET, pTAC, pFLAG, pET, and pT7.

7. The method according to claim 6, wherein said expression vector of the pMAL class is vector pMAL-c2X and said expression vector of the pRSET class is vector pRSET-A.

8. The method according to claim 1, wherein said vector further comprises one or more control sequences operatively linked to said fusion protein selected from the group consisting of an enhancer sequence, a ribosome binding site, a sequence coding for a repressor, an operator sequence, a polyadenylation sequence, and a replication origin.

9. The method according to claim 1, wherein said "purification tag" is selected from the group consisting of: poly/hexahistidine tag, glutathione-S-transferase (GST), maltose binding protein (MBP), thioredoxin, protein A fragment of *Staphylococcus aureus* (ZZ), peptide with affinity for streptavidin (Strep-tag), and flag peptide.

10. The method according to claim 1, wherein said bacterial strain is selected from the group consisting of lysogen *Escherichia coli* strains from D3 series, *Escherichia coli* strains with a Ion and/or ompT and/or dnaJ genotype, and BL21, BL21 AI, C600, CJ236, GC5, GM48, HB101, JM83, JM101, JM103, JM105, JM107, JM109, JM110, K802, LE392, MC1061, MM294, NM477, NM522, NM554, NM621, RR1, χ1776, Rosetta(DE3)pLysS, DH5α, DH10B, ER2566, CAG597, CAG629, ER2508, UT5600, CAG626, PR1031, KS1000, ER2507, and TB1 *Escherichia coli* strains.

11. The method according to claim 1, wherein said inductor is (i) isopropyl β-D-1-thiogalactopyranoside (IPTG) for an expression vector of pMAL, pGEX, pTAC or pFLAG class, or (ii) arabinose for an expression vector of pRSET, pET or pT7 class in the BL21-AI strain.

12. A recombinant *C. histolyticum* collagenase, characterised in that cells extracted with said recombinant *C. histolyticum* collagenase maintain a differentiated phenotype; wherein said recombinant *C. histolyticum* collagenase is produced by a method comprising:
a) designing a nucleotide optimized sequence for expression of said recombinant *C. histolyticum* collagenase, wherein said optimized nucleotide sequence is SEQ ID NO: 1 or SEQ ID NO: 3,
b) introducing, in an inducible expression vector, a nucleotide sequence coding for a fusion protein, wherein said nucleotide sequence comprises said optimized sequence fused to a soluble polypeptide coding sequence through a binding sequence coding for at least one cleavage site for a suitable proteolytic enzyme and wherein said nucleotide sequence is operatively linked to an inducible promoter sequence, a transcription start sequence, and a termination sequence;
c) transforming a bacterial strain defective in expression of endogenous proteases with said expression vector,
d) culturing said transformed bacterial strain at a temperature in a range from 28° C. to 32° C.,
e) inducing expression of said fusion protein by adding a suitable inductor in said bacterial strain,
f) extracting the fusion protein from the induced bacterial strain,
g) purifying said fusion protein, and
h) obtaining said recombinant *C. histolyticum* collagenase by enzymatically cleaving said at least one cleavage site; wherein said method provides a yield higher than 140 mg/l of culture of said recombinant *C. histolyticum* collagenase is soluble and enzymatically active form.

13. The recombinant *C. histolyticum* collagenase according to claim 12, wherein said recombinant *C. histolyticum* collagenase is *C. histolyticum* ColG collagenase or *C. histolyticum* ColH collagenase.

14. A recombinant *C. histolyticum* collagenase encoded by the nucleotide sequence as set forth in SEQ ID NO: 1 or SEQ ID NO: 3, wherein said collagenase is in the form of an MBP-Col fusion protein having a yield higher than 140 mg/l of culture of said recombinant *C. histolyticum* collagenase in soluble and enzymatically active form.

15. The recombinant *C. histolyticum* collagenase according to claim 14, wherein said fusion protein MBP-*C. histolyticum* ColG or MBP-*C. histolyticum* ColH.

16. A recombinant *C. histolyticum* collagenase in the form of an MBP-Col fusion protein having a yield higher than 140 mg/l of culture of said recombinant *C. histolyticum* collagenase in soluble and enzymatically active form which is obtained by the method according to claim 1.

17. A composition comprising one or more recombinant *C. histolyticum* collagenases according to claim 12 and a suitable excipient.

18. A kit for extraction of stem and/or somatic living cells from tissues comprising one or more aliquots of the recombinant *C. histolyticum* collagenase according to claim 12 and one or more aliquots of reagents for extraction of said cells.

19. The kit according to claim 18, wherein said reagents suitable for the extraction comprise neutral proteases and/or thermolysin.

20. A method of using a composition comprising one or more recombinant *C. histolyticum* collagenases according to claim 12, the method comprising extracting stem and/or somatic living cells from a tissue with said collagenase or said composition.

21. The method according to claim 20, wherein said extraction results in isolation of living islets of Langherans from pancreas.

22. The recombinant *C. histolyticum* collagenase according to claim 13, wherein the number of living cells with normal phenotype extracted with recombinant *C. histolyticum* ColG collagenase is at least of about $7.4 \times 10^5$ cells/ml and the number of living cells with normal phenotype extracted with recombinant *C. histolyticum* ColH collagenase is at least of about $8.2 \times 10^5$ cells/ml in the in vitro extraction assay.

* * * * *